US010906881B2

(12) United States Patent
Konradi et al.

(10) Patent No.: US 10,906,881 B2
(45) Date of Patent: Feb. 2, 2021

(54) INHIBITORS OF ARGININE GINGIPAIN

(71) Applicant: Cortexyme, Inc., South San Francisco, CA (US)

(72) Inventors: Andrei Konradi, Burlingame, CA (US); Stephen S. Dominy, Novato, CA (US); Casey C. Lynch, San Francisco, CA (US); Craig Coburn, San Rafael, CA (US); Joseph Vacca, Philadelphia, PA (US)

(73) Assignee: CORTEXYME, INC., San Francisco, CA (US)

( * ) Notice: Subject to any disclaimer, the term of this patent is extended or adjusted under 35 U.S.C. 154(b) by 0 days.

(21) Appl. No.: 15/975,490

(22) Filed: May 9, 2018

(65) Prior Publication Data

US 2018/0334440 A1 Nov. 22, 2018

Related U.S. Application Data

(63) Continuation of application No. PCT/US2016/061197, filed on Nov. 9, 2016.

(60) Provisional application No. 62/338,924, filed on May 19, 2016, provisional application No. 62/253,039, filed on Nov. 9, 2015.

(51) Int. Cl.
| C07C 279/12 | (2006.01) |
| A61P 31/04 | (2006.01) |
| C07D 277/64 | (2006.01) |
| C07D 417/12 | (2006.01) |

(52) U.S. Cl.
CPC ............ *C07D 277/64* (2013.01); *A61P 31/04* (2018.01); *C07C 279/12* (2013.01); *C07D 417/12* (2013.01); *C07C 2601/08* (2017.05); *C07C 2601/16* (2017.05)

(58) Field of Classification Search
None
See application file for complete search history.

(56) References Cited

U.S. PATENT DOCUMENTS

| 5,451,410 | A | 9/1995 | Milstein et al. |
| 5,523,308 | A | 6/1996 | Costanzo et al. |
| 5,827,866 | A | 10/1998 | Costanzo et al. |
| 6,323,219 | B1 | 11/2001 | Costanzo |
| 7,183,260 | B2 | 2/2007 | Karanewsky et al. |
| 9,758,473 | B2 | 9/2017 | Konradi et al. |
| 9,988,375 | B2 | 6/2018 | Konradi et al. |
| 10,301,301 | B2 | 5/2019 | Konradi et al. |
| 2003/0008829 | A1 | 1/2003 | Costanzo et al. |
| 2003/0166680 | A1 | 9/2003 | Greco et al. |
| 2005/0020504 | A1 | 1/2005 | Karanewsky et al. |
| 2005/0059607 | A1 | 3/2005 | Breslav et al. |
| 2006/0084613 | A1 | 4/2006 | Ternansky et al. |
| 2011/0092510 | A1 | 4/2011 | Klein et al. |
| 2014/0378372 | A1 | 12/2014 | Mogelsvang et al. |
| 2016/0096830 | A1 | 4/2016 | Konradi et al. |
| 2017/0014468 | A1 | 1/2017 | Dominy et al. |

FOREIGN PATENT DOCUMENTS

| AU | 2005334458 A1 | 3/2007 |
| EP | 0195212 | 9/1986 |
| EP | 0 272 671 A2 | 6/1988 |
| EP | 530167 A1 | 3/1993 |
| JP | 01-163162 A | 6/1989 |
| WO | 92/04371 A1 | 3/1992 |
| WO | 93/00926 A1 | 1/1993 |
| WO | 94/04172 A1 | 3/1994 |
| WO | 96/19483 A1 | 6/1996 |
| WO | 96/30035 A1 | 10/1996 |
| WO | 96/30396 A1 | 10/1996 |
| WO | 96/37497 A1 | 11/1996 |
| WO | 96/40741 A1 | 12/1996 |
| WO | 96/40742 A1 | 12/1996 |
| WO | 97/17363 A1 | 5/1997 |
| WO | 98/05333 A1 | 2/1998 |
| WO | 98/09987 A1 | 3/1998 |
| WO | 99/26925 A1 | 6/1999 |
| WO | 99/41276 A1 | 8/1999 |
| WO | 00/44733 A1 | 8/2000 |
| WO | 00/55124 A2 | 9/2000 |
| WO | 2007137080 | 11/2007 |
| WO | 2014/145257 A2 | 9/2014 |
| WO | 2014/145986 A2 | 9/2014 |
| WO | 2016/057413 A2 | 4/2016 |
| WO | 2017/083433 A1 | 5/2017 |

OTHER PUBLICATIONS

Adang et al., "Unique Overlap in the Prerequisites for Thrombin Inhibition and Oral Bioavailability Resulting in Potent Oral Antithrombotics," J. Med. Chem., 2002, vol. 45, pp. 4419-4432.
Berg et al., "Design and evaluation of *Trypanosoma brucei* metacaspase inhibitors," Bioorg. Med. Chem. Lett., Mar. 15, 2010; 20(6): 2001-2006.
Bialas et al., "Exploring the Sn Binding Pockets in Gingipains by Newly Developed Inhibitors: Structure-Based Design, Chemistry, and Activity," Journal of Medicinal Chemistry, 2006, vol. 49, No. 5, pp. 1744-1753.
Bland et al., "Reductive Cleavage of Acyl-guanidines to Amines," Chemical Communications, 1971, 17, pp. 1024-1025.
CAS Registry Entry for Registry No. 190903-94-7, which entered STN on Jul. 9, 1997.

(Continued)

*Primary Examiner* — Joseph R Kosack
(74) *Attorney, Agent, or Firm* — Kilpatrick Townsend & Stockton LLP

(57) ABSTRACT

The present invention relates generally to therapeutics targeting the bacterium *Porphyromonas gingivalis*, including its proteases arginine gingipain A/B (Rgp), and their use for the treatment of disorders associated with *P. gingivalis* infection, including brain disorders such as Alzheimer's disease. In certain embodiments, the invention provides compounds according to Formula I, as described herein, and pharmaceutically acceptable salts thereof.

17 Claims, 6 Drawing Sheets

Specification includes a Sequence Listing.

(56) References Cited

OTHER PUBLICATIONS

CAS Registry Entry for Registry No. 190904-52-0, which entered STN on Jul. 9, 1997.

CAS Registry Entry for Registry No. 607393-00-0, which entered STN on Oct. 21, 2003.

Chauhan, Satendra S., "Enantioselective synthesis of (L)-Fmoc-α-Me-Lys(Boc)-OH via diastereoselective alkylation of oxazinone as a chiral auxiliary," Tetrahedron Letters, 2009, vol. 50, pp. 6913-6915.

Costanzo et al., "In-Depth Study of Tri peptide-Based a-Ketoheterocycles as Inhibitors of Thrombin. Effective Utilization of the S1 Subsite and Its Implications to Structure-Based Drug Design," J. Med. Chem., 2005, 48 (6), pp. 1984-2008, Abstract.

Curtis et al., "Attenuation of the Virulence of *Porphyromonas gingivalis* by Using a Specific Synthetic Kgp Protease Inhibitor," Infection and Immunity, Dec. 2002, vol. 70., No. 12, pp. 6968-6975.

Duchene et al., "Analysis of Subpocket Selectivity and Identification of Potent Selective Inhibitors for Matriptase and Matriptasli-2," J. Med. Chem., vol. 57, Nov. 11, 2014, pp. 10198-10204.

Kataoka et al., "A Novel, Potent Dual Inhibitor of ARG-Gingipains and LYS-Gingipain As a Promising Agent for Periodontal Disease Therapy," FASEB J, 2014, vol. 28, 3564-3578.

McGrath et al., "Structure-Guided Design of Peptide-Based Tryptase Inhibitors," Biochemistry, 2006, vol. 45, No. 19, pp. 5964-5973.

Mogami et al., "Effect of Thrombin on Human Amnion Mesenchymal Cells, Mouse Fetal Membranes, and Preterm Birth," Journal of Biological Chemistry, May 9, 2014, vol. 289, No. 19, pp. 13295-13307.

PCT/US2016/061197, "International Search Report" dated Jan. 25, 2017, 5 pages.

Sengupta et al., "Synthesis and biological evaluation of novel oxalamido derivatives as caspase-3 inhibitors," Indian J. Chem. Sec B, vol. 50B, Jul. 2011, pp. 901-905.

Teno et al., "Development of Active Center-Directed Inhibitors against Plasmin[1]," Chem. Pharm. Bull., 1991, vol. 39(9), pp. 2340-2346.

Kadowaki et al., "Suppression of Pathogenicity of *Porphyromonas gingivalis* by Newly Developed Gingipain inhibitors," Mol Pharmacol, Dec. 2004, vol. 66, No. 6, pp. 1599-1606.

Compound 14

Vehicle

*P. gingivalis*

*P. Gingivalis* + Compound 13

INHIBITORS OF ARGININE GINGIPAIN

CROSS REFERENCES TO RELATED APPLICATIONS

The present application is a continuation of International Patent Application No. PCT/US2016/061197 filed Nov. 9, 2016, which claims the benefit of and priority to U.S. Provisional Pat. Appl. No. 62/253,039, filed Nov. 9, 2015, and U.S. Provisional Pat. Appl. No. 62/338,924, filed May 19, 2016, which applications are incorporated herein by reference in their entirety for all purposes.

REFERENCE TO A SEQUENCE LISTING

The Sequence Listing written in file SequenceListing_098460-000410US-1086520.txt created on Aug. 6, 2018, 934 bytes, machine format IBM-PC, MS-Windows operating system, is hereby incorporated by reference in its entirety for all purposes.

BACKGROUND OF THE INVENTION

Infection with the bacteria *Porphyromonas gingivalis* has been linked to the development of periodontal disease, Alzheimer's and other brain disorders, cardiovascular disease, diabetes, cancer, liver disease, kidney disease, preterm birth, arthritis, pneumonia and other disorders. *P. gingivalis* is an anaerobic asaccharolytic gram-negative rod bacterium that is known to infect the oral cavity and translocate systemically into coronary arteries, aorta, placental tissue, the brain, the kidneys, and the liver. The bacterium has also been identified in cancerous tissues and a mechanism has been proposed by which gingipains can trigger immortalization and metastasis. See: Gandhimadhi, et al. *Journal of Indian Society of Periodontology.* 2010; 14(2):114-120; Liao, et al., *MedHypotheses,* 2009. 72(6): 732-5; Byrne, et al., *Oral Microbiol Immunol,* 2009. 24(6): 469-77; Mahendra, et al., *J Maxillofac Oral Surg,* 2009. 8(2): 108-13; Stelzel, et al., *J Periodontol,* 2002. 73(8): 868-70; Katz, et al., *Journal of Dental Research,* 2009. 88(6): 575-578; Poole, et al., *J Alzheimers Dis,* 2015, 43(1): 67-80; Ishikawa, et al., *Biochim Biophys Acta,* 2013. 1832(12): 2035-2043; Inaba, et al., *Cellular Microbiology,* 2014. 16(1): 131-145.

*P. gingivalis* produces proteases called gingipains, including Arginine Gingipain A (RgpA), Arginine Gingipain B (RgpB) and Lysine Gingipain (Kgp). Gingipains contribute to many functions of the organism including its survival and virulence. Gingipains can be secreted, transported to outer membrane surfaces of *P. gingivalis*, or released in outer membrane vesicles by the bacterium. Gingipains degrade a broad range of proteins (e.g., immunoglobulins, proteinase inhibitors, actin, and collagen) which can lead to cytoskeleton collapse and apoptosis in many types of cells. Recent research has demonstrated that inhibitors of gingipains can prevent *P. gingivalis*-induced cell death. See: Travis, et al., *Adv Exp MedBiol,* 2000. 477: 455-65; Sheets, et al., *Infect Immun,* 2005. 73(3): 1543-52; Sheets, et al., *Infect Immun,* 2006. 74(10): 5667-78; Stathopoulou, et al., *BMC Microbiol,* 2009. 9: 107. New compounds for the inhibition of gingipain activity and the treatment of diseases associated with gingipain activity and *P. gingivalis* infection are needed. The present invention addresses this and other needs.

BRIEF SUMMARY OF THE INVENTION

In one aspect, the invention provides a compound according to Formula I:

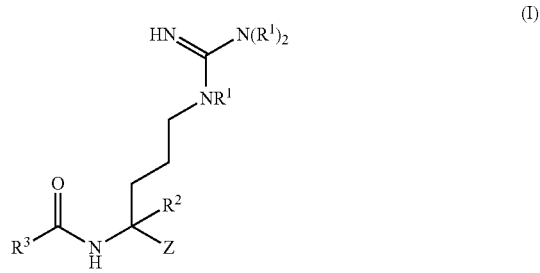

or a pharmaceutically acceptable salt thereof, wherein:

Z is selected from aryloxymethyl-carbonyl, benzothiazol-2-yl-carbonyl, thiazol-2-yl-carbonyl, oxazol-2-yl-carbonyl, benzooxazol-2-yl-carbonyl, pyridin-2-yl-carbonyl, pyrimidin-4-yl-carbonyl, pyrimidin-2-yl-carbonyl, isoxazol-5-yl-carbonyl, isoxazol-3-yl-carbonyl, 1,2,4-oxadiazol-3-yl-carbonyl, 1,2,4-oxadiazol-5-yl-carbonyl, cyano, ethynyl, fluoromethyl-carbonyl, acyloxymethyl-carbonyl, alkylsulfonyl-vinyl, and arylsulfonyl-vinyl; wherein Z is optionally substituted with one or more substituents selected from halogen, $C_{1-4}$ alkyl, $C_{1-4}$ alkoxy, $C_{1-4}$ haloalkyl, $C_{1-4}$ haloalkoxy, and $—N_3$;

each $R^1$ is independently selected from hydrogen, $C_{1-4}$ alkyl, and an amine protecting group;

$R^2$ is selected from hydrogen and $C_{1-4}$ alkyl;

$R^3$ is selected from $C_{3-8}$ alkyl, $C_{3-8}$ cycloalkyl, $C_{6-10}$ aryl, 5-to-12 membered heteroaryl, and 5-to-12 membered heterocyclyl, wherein $R^3$ is optionally substituted with one or more $R^4$ substituents independently selected from halo, —CN, —$NO_2$, —$N_3$, —OH, $R^a$, —$OR^b$, —$N(R^d)_2$, —$(CH_2)_kC(O)R^c$, —$NR^d(CH_2)_uC(O)R^c$, —$O(CH_2)_uC(O)R^c$, —$(CH_2)_kCON(R^d)_2$, —$(CH_2)_kNR^dC(O)R^c$, —$NR^d(CH_2)_uCON(R^d)_2$, —$NR^d(CH_2)_uNR^dC(O)R^c$, —$O(CH_2)_uCON(R^d)_2$, and —$O(CH_2)_uNR^dC(O)R^c$;

each $R^a$, $R^b$, and $R^c$ is independently selected from $C_{1-4}$ alkyl and $C_{1-4}$ haloalkyl, each $R^d$ is independently selected from hydrogen and $C_{1-8}$ alkyl, each subscript k is independently selected from 0, 1, 2, 3, 4, 5, and 6, and each subscript u is independently selected from 1, 2, 3, 4, 5, and 6;

provided that when Z is phenyoxymethylcarbonyl or substituted phenoxymethylcarbonyl, $R^3$ and the carbonyl to which it is bonded form a moiety other than prolinyl, substituted prolinyl, argininyl, substituted argininyl, phenylalaninyl, substituted phenylalaninyl, tert-butylaminocarbonyl, or tert-butyloxycarbonyl; and provided that when Z is benzothiazol-2-yl-carbonyl, $R^3$ is selected from phenyl, trifluromethylphenyl, piperidin-3-yl, pyrrolidin-3-yl, 3-aminocyclopentyl, n-propyl, 3-aminopropyl, and (1-acetamido)propyl.

In some embodiments, the compound has a structure according to Formula Ib:

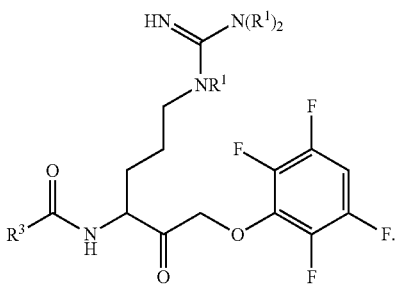

or a pharmaceutically acceptable salt thereof.

In some embodiments, the compound has a structure according to Formula Ic:

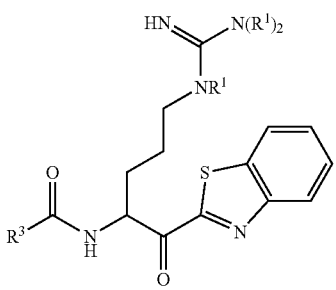

or a pharmaceutically acceptable salt thereof, wherein $R^3$ is selected from phenyl, trifluromethylphenyl, piperidin-3-yl, pyrrolidin-3-yl, 3-aminocyclopentyl, n-propyl, 3-aminopropyl, and (1-acetamido)propyl.

In another aspect, the invention provides a pharmaceutical composition comprising a compound according to Formula I and a pharmaceutically acceptable excipient.

In another aspect, the invention provides a method of treating a disease or condition associated with *P. gingivalis* infection. The method includes administering to a subject an effective amount of a compound according to Formula II:

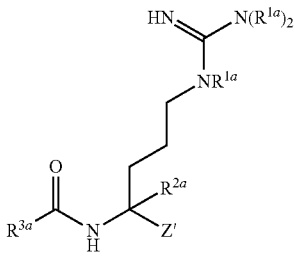

or a pharmaceutically acceptable salt thereof, wherein:

Z' is selected from aryloxymethyl-carbonyl, benzothiazol-2-yl-carbonyl, thiazol-2-yl-carbonyl, oxazol-2-yl-carbonyl, benzooxazol-2-yl-carbonyl, pyridin-2-yl-carbonyl, pyrimidin-4-yl-carbonyl, pyrimidin-2-yl-carbonyl, isoxazol-5-yl-carbonyl, isoxazol-3-yl-carbonyl, 1,2,4-oxadiazol-3-yl-carbonyl, 1,2,4-oxadiazol-5-yl-carbonyl, cyano, ethynyl, fluoromethyl-carbonyl, acyloxymethyl-carbonyl, alkylsulfonyl-vinyl, and arylsulfonyl-vinyl;

wherein Z' is optionally substituted with one or more substituents selected from halogen, $C_{1-4}$ alkyl, $C_{1-4}$ alkoxy, $C_{1-4}$ haloalkyl, $C_{1-4}$ haloalkoxy, and $-N_3$;

each $R^{1a}$ is independently selected from hydrogen, $C_{1-4}$ alkyl, and an amine protecting group;

$R^{2a}$ is selected from hydrogen and $C_{1-4}$ alkyl;

$R^{3a}$ is selected from $C_{3-8}$ cycloalkyl, $C_{3-8}$ alkyl, $C_{6-10}$ aryl, 5-to-12 membered heteroaryl, and 5-to-12 membered heterocyclyl, wherein $R^{3a}$ is optionally substituted with one or more $R^{4a}$ substituents independently selected from halo, $-CN$, $-NO_2$, $-N_3$, $-OH$, $R^a$, $-OR^b$, $-N(R^d)_2$, $-(CH_2)_kC(O)R^c$, $-NR^d(CH_2)_uC(O)R^c$, $-O(CH_2)_uC(O)R^c$, $-(CH_2)_kCON(R^d)_2$, $-(CH_2)_kNR^dC(O)R^c$, $-NR^d(CH_2)_uCON(R^d)_2$, $-NR^d(CH_2)_uNR^dC(O)R^c$, $-O(CH_2)_uCON(R^d)_2$, and $-O(CH_2)_uNR^dC(O)R^c$;

each $R^a$, $R^b$, and $R^c$ is independently selected from $C_{1-4}$ alkyl and $C_{1-4}$ haloalkyl, each $R^d$ is independently selected from hydrogen and $C_{1-8}$ alkyl, each subscript k is independently selected from 0, 1, 2, 3, 4, 5, and 6, and each subscript u is independently selected from 1, 2, 3, 4, 5, and 6.

In some embodiments, the disease or condition associated with *P. gingivalis* infection is a brain disorder selected from Alzheimer's disease, Down's syndrome, epilepsy, autism, Parkinson's disease, essential tremor, fronto-temporal dementia, progressive supranuclear palsy, amyotrophic lateral sclerosis, Huntington's disease, multiple sclerosis, mild cognitive impairment, age associated memory impairment, chronic traumatic encephalopathy, stroke, cerebrovascular disease, Lewy Body disease, multiple system atrophy, schizophrenia, and depression. In some embodiments, the disease or condition associated with *P. gingivalis* infection is Alzheimer's disease.

BRIEF DESCRIPTION OF THE DRAWINGS

In FIG. 4, R represents a radionuclide or a radionuclide-substituted moiety (e.g., R=$^{18}$F-alkylene).

DETAILED DESCRIPTION OF THE INVENTION

I. General

Figure 1:
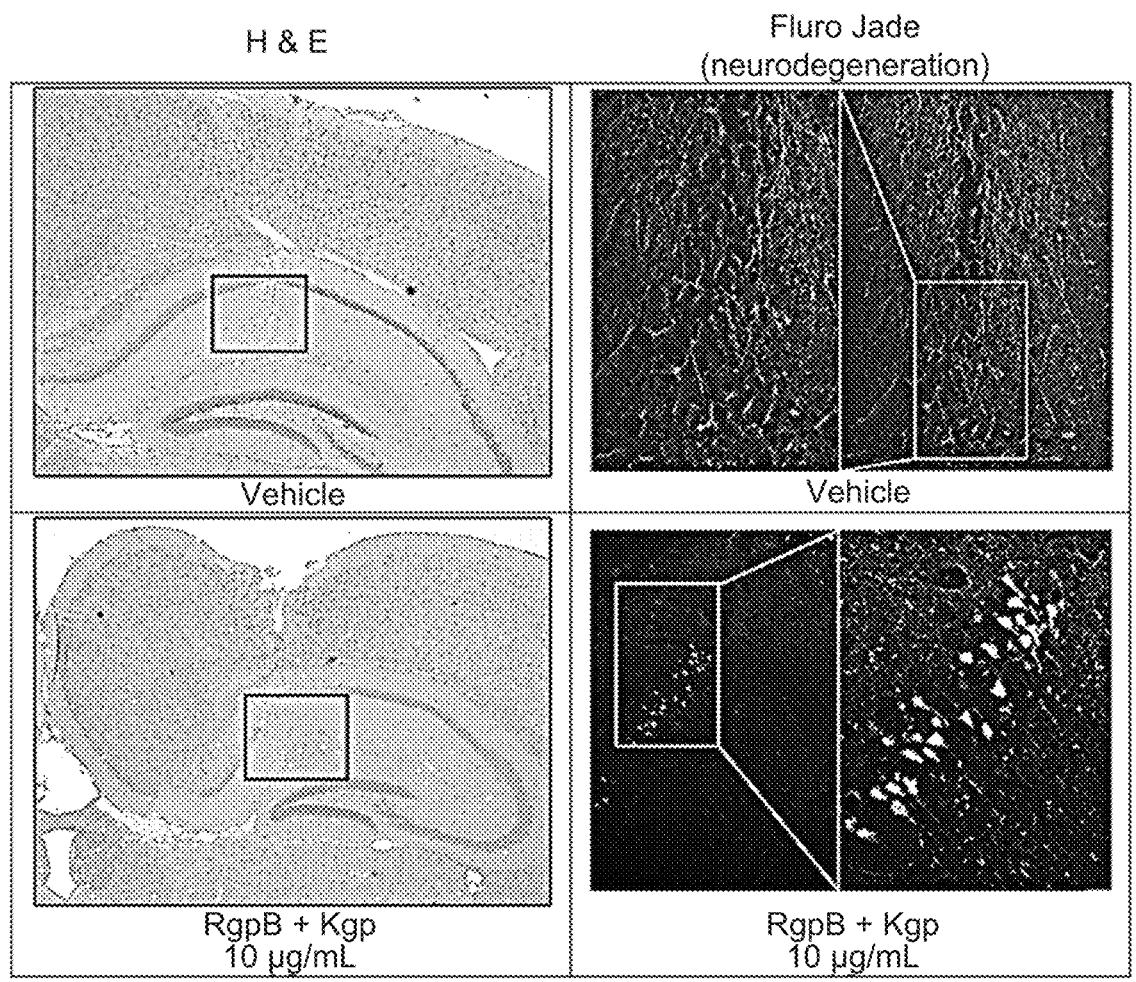
FIG. 1 shows that intrahippocampal injection of gingipains into mouse brain causes neurodegeneration after 7 days.

Inhibition of gingipains has been shown to protect cells, prevent bacterial growth, increase immune system surveillance of the bacteria, and protect against reinfection. The present invention provides potent and selective nonpeptidic compounds for inhibition of arginine gingipains. The compounds can be used to prevent cell death, inflammation, and other pathology in a variety of diseases associated with P. gingivalis infection, including aging-related conditions such as Alzheimer's disease.

II. Definitions

As used herein, the term "alkyl," by itself or as part of another substituent, refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted. "Substituted alkyl" groups can be substituted with one or more groups selected from halo, hydroxy, amino, alkylamino, amido, acyl, nitro, cyano, and alkoxy.

As used herein, the term "alkoxy," by itself or as part of another substituent, refers to a group having the formula —OR, wherein R is alkyl. The term "lower alkoxyl" refers to an alkoxy radical having from one to seven carbons, e.g., methoxyl, ethoxyl, propoxyl, butoxyl, pentoxyl, hexoxyl, or heptoxyl radical.

As used herein, the term "cycloalkyl," by itself or as part of another substituent, refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbomadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl groups can be substituted or unsubstituted. "Substituted cycloalkyl" groups can be substituted with one or more groups selected from halo, hydroxy, amino, alkylamino, amido, acyl, nitro, cyano, and alkoxy. The term "lower cycloalkyl" refers to a cycloalkyl radical having from three to seven carbons including, for example, cyclopropyl, cyclobutyl, cyclopentyl, cyclohexyl, and cycloheptyl.

As used herein, the term "alkylene" refers to an alkyl group, as defined above, linking at least two other groups (i.e., a divalent alkyl radical). The two moieties linked to the alkylene group can be linked to the same carbon atom or different carbon atoms of the alkylene group.

As used herein, the term "heteroalkyl," by itself or as part of another substituent, refers to an alkyl group of any suitable length and having from 1 to 3 heteroatoms such as N, O and S. For example, heteroalkyl can include ethers, thioethers and alkyl-amines. Additional heteroatoms can also be useful, including, but not limited to, B, Al, Si and P. The heteroatoms can be oxidized to form moieties such as, but not limited to, —S(O)— and —S(O)$_2$—. The heteroatom portion of the heteroalkyl can replace a hydrogen of the alkyl group to form a hydroxy, thio or amino group. Alternatively, the heteroatom portion can be the connecting atom, or be inserted between two carbon atoms.

As used herein, the term "heteroalkylene" refers to a heteroalkyl group, as defined above, linking at least two other groups (i.e., a divalent heteroalkyl radical). The two moieties linked to the heteroalkylene group can be linked to the same atom or different atoms of the heteroalkylene group.

As used herein, the terms "halo" and "halogen," by themselves or as part of another substituent, refer to a fluorine, chlorine, bromine, or iodine atom.

As used herein, the term "haloalkyl," by itself or as part of another substituent, refers to an alkyl group where some or all of the hydrogen atoms are replaced with halogen atoms. As for alkyl groups, haloalkyl groups can have any suitable number of carbon atoms, such as $C_{1-6}$. For example, haloalkyl includes trifluoromethyl, fluoromethyl, etc. In some instances, the term "perfluoro" can be used to define a compound or radical where all the hydrogens are replaced with fluorine. For example, perfluoromethyl refers to 1,1,1-trifluoromethyl.

As used herein, the term "haloalkoxy," by itself or as part of another substituent, refers to an alkoxy group where some or all of the hydrogen atoms are replaced with halogen atoms.

As used herein, the term "halocycloalkyl," by itself or as part of another substituent, refers to a cycloalkyl group where some or all of the hydrogen atoms are replaced with halogen atoms.

As used herein, the term "aryl," by itself or as part of another substituent, refers to an aromatic ring system having any suitable number of ring atoms and any suitable number of rings. Aryl groups can include any suitable number of ring atoms, such as 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic (e.g., benzocyclohexyl) or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted. "Substituted aryl" groups can be substituted with one or more groups selected from halo, hydroxy, amino, alkylamino, amido, acyl, nitro, cyano, and alkoxy.

As used herein, the term "heteroaryl," by itself or as part of another substituent, refers to a monocyclic or fused bicyclic or tricyclic aromatic ring assembly containing 5 to 16 ring atoms, where from 1 to 5 of the ring atoms are a heteroatom such as N, O or S. Additional heteroatoms can also be useful, including, but not limited to, B, Al, Si and P. The heteroatoms can be oxidized to form moieties such as, but not limited to, —S(O)— and —S(O)$_2$—. Heteroaryl groups can include any number of ring atoms, such as 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted. "Substituted heteroaryl" groups can be substituted with one or more groups selected from halo, hydroxy, amino, alkylamino, amido, acyl, nitro, cyano, and alkoxy.

The heteroaryl groups can be linked via any position on the ring. For example, pyrrole includes 1-, 2- and 3-pyrrole, pyridine includes 2-, 3- and 4-pyridine, imidazole includes 1-, 2-, 4- and 5-imidazole, pyrazole includes 1-, 3-, 4- and 5-pyrazole, triazole includes 1-, 4- and 5-triazole, tetrazole includes 1- and 5-tetrazole, pyrimidine includes 2-, 4-, 5- and 6-pyrimidine, pyridazine includes 3- and 4-pyridazine, 1,2,3-triazine includes 4- and 5-triazine, 1,2,4-triazine includes 3-, 5- and 6-triazine, 1,3,5-triazine includes 2-triazine, thiophene includes 2- and 3-thiophene, furan includes 2- and 3-furan, thiazole includes 2-, 4- and 5-thiazole, isothiazole includes 3-, 4- and 5-isothiazole, oxazole includes 2-, 4- and 5-oxazole, isoxazole includes 3-, 4- and 5-isoxazole, indole includes 1-, 2- and 3-indole, isoindole includes 1- and 2-isoindole, quinoline includes 2-, 3- and 4-quinoline, isoquinoline includes 1-, 3- and 4-isoquinoline, quinazoline includes 2- and 4-quinoazoline, cinnoline includes 3- and 4-cinnoline, benzothiophene includes 2- and 3-benzothiophene, and benzofuran includes 2- and 3-benzofuran.

Some heteroaryl groups include those having from 5 to 10 ring members and from 1 to 3 ring atoms including N, O or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring atoms including N, O or S, such as pyrrole, pyridine, imidazole, pyrazole, pyrazine, pyrimidine, pyridazine, thiophene, furan, thiazole, isothiazole, oxazole, and isoxazole.

Some heteroaryl groups include from 5 to 10 ring members and only nitrogen heteroatoms, such as pyrrole, pyridine, imidazole, pyrazole, triazole, pyrazine, pyrimidine, pyridazine, triazine (1,2,3-, 1,2,4- and 1,3,5-isomers), indole, isoindole, quinoline, isoquinoline, quinoxaline, quinazoline, phthalazine, and cinnoline. Other heteroaryl groups include from 5 to 10 ring members and only oxygen heteroatoms, such as furan and benzofuran. Some other heteroaryl groups include from 5 to 10 ring members and only sulfur heteroatoms, such as thiophene and benzothiophene. Still other heteroaryl groups include from 5 to 10 ring members and at least two heteroatoms, such as imidazole, pyrazole, triazole, pyrazine, pyrimidine, pyridazine, triazine (1,2,3-, 1,2,4- and 1,3,5-isomers), thiazole, isothiazole, oxazole, isoxazole, quinoxaline, quinazoline, phthalazine, and cinnoline.

As used herein the term "heterocyclyl," by itself or as part of another substituent, refers to a saturated ring system having from 3 to 12 ring members and from 1 to 4 heteroatoms of N, O and S. Additional heteroatoms can also be useful, including, but not limited to, B, Al, Si and P. The heteroatoms can be oxidized to form moieties such as, but not limited to, —S(O)— and —S(O)$_2$—. Heterocyclyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocyclyl groups, such as 1, 2, 3, or 4, or 1 to 2, 1 to 3, 1 to 4, 2 to 3, 2 to 4, or 3 to 4. The heterocyclyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocyclyl groups can also be fused to aromatic or non-aromatic ring systems to form members including, but not limited to, indoline. Heterocyclic groups can be saturated (e.g., azetidinyl, pyrrolidinyl, piperidinyl, morpholine, oxetanyl, tetrahydrofuranyl, or tetrahydropyranyl) or unsaturated (e.g., 2,3-dihydrofuranyl, 2,5-dihydrofuranyl, 3,4-dihydropyranyl, 3,6-dihydropyranyl, or 1,4-dihydropyridinyl). Heterocyclyl groups can be unsubstituted or substituted. "Substituted heterocyclyl"

groups can be substituted with one or more groups selected from halo, hydroxy, amino, oxo (=O), alkylamino, amido, acyl, nitro, cyano, and alkoxy.

The heterocyclyl groups can be linked via any position on the ring. For example, aziridine can be 1- or 2-aziridine, azetidine can be 1- or 2-azetidine, pyrrolidine can be 1-, 2- or 3-pyrrolidine, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, tetrahydrofuran can be 1- or 2-tetrahydrofuran, oxazolidine can be 2-, 3-, 4- or 5-oxazolidine, isoxazolidine can be 2-, 3-, 4- or 5-isoxazolidine, thiazolidine can be 2-, 3-, 4- or 5-thiazolidine, isothiazolidine can be 2-, 3-, 4- or 5-isothiazolidine, and morpholine can be 2-, 3- or 4-morpholine.

When heterocyclyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxazolidine, thiazolidine, isothiazolidine, morpholine, thiomorpholine, dioxane and dithiane. Heterocyclyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

As used herein, the term "amine protecting group" refers to a chemical moiety that renders an amino group unreactive, but is also removable so as to restore the amino group. Examples of amine protecting groups include, but are not limited to, benzyloxycarbonyl; 9-fluorenylmethyloxycarbonyl (Fmoc); tert-butyloxycarbonyl (Boc); allyloxycarbonyl (Alloc); p-toluene sulfonyl (Tos); 2,2,5,7,8-pentamethylchroman-6-sulfonyl (Pmc); 2,2,4,6,7-pentamethyl-2,3-dihydrobenzofuran-5-sulfonyl (Pbf); mesityl-2-sulfonyl (Mts); 4-methoxy-2,3,6-trimethylphenylsulfonyl (Mtr); acetamido; phthalimido; and the like. Other amine protecting groups are known to those of skill in the art including, for example, those described by Green and Wuts (*Protective Groups in Organic Synthesis*, 4$^{th}$ Ed. 2007, Wiley-Interscience, New York).

As used herein, the term "amino acid residue" refers to a moiety having the structure:

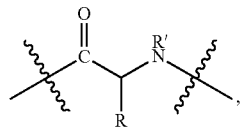

wherein R represents the side chain of a naturally occurring amino acid (e.g., alanine, arginine, asparagine, aspartic acid, cysteine, glutamine, glutamic acid, glycine, histidine, isoleucine, leucine, lysine, methionine, phenylalanine, proline, selenocysteine, serine, threonine, tryptophan, tyrosine, valine) or a non-naturally occurring amino acid (e.g., azidohomoalanine, propargylglycine, p-acetylphenylalanine, and the like); R' is hydrogen, $C_{1-4}$ alkyl, or an amine protecting group as described herein; and the wavy lines represent the points of connection from the amino acid residue to the other groups in the molecule having the amino acid residue. One of skill in the art will appreciate that for peptidic compounds having more than one amino acid residue linked together, the points of connection between amino acid residues are amide (i.e., peptide) bonds. The "N-terminal" amino acid residue will be bonded to a molecule at the carbonyl moiety (C=O) in the N-terminal amino acid residue, and that the amino moiety (NR') in the N-terminal amino acid residue will be bonded to a hydrogen atom. Similarly, a "C-terminal" amino acid residue will be bonded to a molecule at the amino moiety (NR') in the C-terminal amino acid residue, and the carbonyl moiety (C=O) in the C-terminal amino acid residue will be bonded to a hydroxyl group.

As used herein, the term "carbonyl," by itself or as part of another substituent, refers to —C(O)—, i.e., a carbon atom double-bonded to oxygen and bound to two other groups in the moiety having the carbonyl.

As used herein, the term "amino" refers to a moiety —NR$_3$, wherein each R group is H or alkyl. An amino moiety can be ionized to form the corresponding ammonium cation.

As used herein, the term "hydroxy" refers to the moiety —OH.

As used herein, the term "cyano" refers to a carbon atom triple-bonded to a nitrogen atom (i.e., the moiety —C≡N).

As used herein, the term "carboxy" refers to the moiety —C(O)OH. A carboxy moiety can be ionized to form the corresponding carboxylate anion.

As used herein, the term "amido" refers to a moiety —NRC(O)R or —C(O)NR$_2$, wherein each R group is H or alkyl.

As used herein, the term "nitro" refers to the moiety —NO$_2$.

As used herein, the term "oxo" refers to an oxygen atom that is double-bonded to a compound (i.e., O=).

As used herein the term "prolinyl" refers to a moiety having the structure

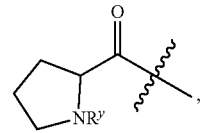

wherein R$^y$ is selected from hydrogen, $C_{1-4}$ alkyl, amido, acyl, an amine protecting group, an amino acid residue, a peptide residue, or a polypeptide residue; and wherein the wavy line marks the point of connection to the remainder of the molecule. For "unsubstituted prolinyl," R$^y$ is hydrogen. For "substituted prolinyl," R$^y$ is $C_{1-4}$ alkyl, amido, acyl, an amine protecting group, an amino acid residue, a peptide residue, or a polypeptide residue; and the prolinyl group can be further substituted with one or more groups selected from halo, hydroxy, amino, oxo (=O), alkylamino, amido, acyl, nitro, cyano, and alkoxy.

As used herein, the term "argininyl" refers to a moiety having the structure

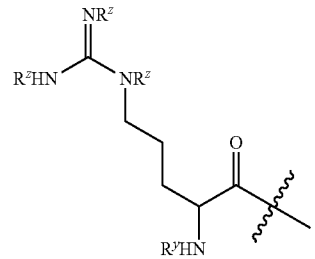

wherein $R^y$ is selected from hydrogen, $C_{1-4}$ alkyl, amido, acyl, an amine protecting group, an amino acid residue, a peptide residue, or a polypeptide residue; wherein each $R^z$ is independently selected from hydrogen, $C_{1-4}$ alkyl, and an amine protecting group; and wherein the wavy line marks the point of connection to the remainder of the molecule. For "unsubstituted argininyl," $R^y$ is hydrogen. For "substituted argininyl," $R^y$ is $C_{1-4}$ alkyl, amido, acyl, an amine protecting group, an amino acid residue, a peptide residue, or a polypeptide residue; and the argininyl group can be further substituted with one or more groups selected from halo, hydroxy, amino, oxo (=O), alkylamino, amido, acyl, nitro, cyano, and alkoxy.

As used herein, the term "phenylalaninyl" refers to a moiety having the structure

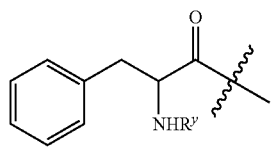

wherein $R^y$ is selected from hydrogen $C_{1-4}$ alkyl, amido, acyl, an amine protecting group, an amino acid residue, a peptide residue, or a polypeptide residue; and wherein the wavy line marks the point of connection to the remainder of the molecule. For "unsubstituted phenylalaninyl," $R^y$ is hydrogen. For "substituted phenylalaninyl," $R^y$ is $C_{1-4}$ alkyl, amido, acyl, an amine protecting group, an amino acid residue, a peptide residue, or a polypeptide residue; and the phenylalaninyl group can be further substituted with one or more groups selected from halo, hydroxy, amino, oxo (=O), alkylamino, amido, acyl, nitro, cyano, and alkoxy As used herein, the term "pharmaceutically acceptable excipient" refers to a substance that aids the administration of an active agent to a subject. By "pharmaceutically acceptable," it is meant that the excipient is compatible with the other ingredients of the formulation and is not deleterious to the recipient thereof. Pharmaceutical excipients useful in the present invention include, but are not limited to, binders, fillers, disintegrants, lubricants, glidants, coatings, sweeteners, flavors and colors.

As used herein, the term "salt" refers to acid or base salts of the compounds of the invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic.

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

As used herein, the terms "*Porphyromonas gingivalis*" and "*P. gingivalis*" refer to the gram-negative asaccharolytic bacterium that is recognized as a key causative microbe in the pathogenesis of periodontitis and related conditions. "*P. gingivalis* infection" refers to the invasion and colonization of *P. gingivalis* in a bodily tissue such as the gums or the brain. *P. gingivalis* infection is frequently characterized by subsequent tissue injury and disease.

As used herein, the term "gingipain" refers to cysteine proteases expressed by *P. gingivalis* having trypsin-like specificity (i.e., Lys-Xaa and Arg-Xaa). Gingipains are recognized as the major virulence factors of *P. gingivalis* and contribute to bacterial attachment and colonization, nutrient acquisition, evasion of host defenses, and tissue invasion. The terms "arginine gingipain" and "Rgp" are used interchangeably to refer to the *P. gingivalis* arginine-specific gingipains RgpA and RgpB, classified under EC number EC 3.4.22.37. The rgpA and rgpB gene-translation products, RgpA and RgpB, share a caspase-like protease domain (specific for Arg-Xaa peptide bonds) and an immunoglobulin-like domain. In RgpA, the protease and immunoglobulin-like domains are followed by a large C-terminal extension containing hemagglutinin-adhesin domains.

As used herein, the terms "treat," "treatment," and "treating" refer to any indicia of success in the treatment or amelioration of an injury, pathology, condition, or symptom (e.g., cognitive impairment), including any objective or subjective parameter such as abatement; remission; diminishing of symptoms or making the symptom, injury, pathology or condition more tolerable to the patient; reduction in the rate of symptom progression; decreasing the frequency or duration of the symptom or condition; or, in some situations, preventing the onset of the symptom. The treatment or amelioration of symptoms can be based on any objective or subjective parameter; including, e.g., the result of a physical examination.

As used herein the terms "effective amount" and "therapeutically effective amount" refer to a dose of a compound such as an Rgp inhibitor that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); Goodman & Gilman's *The Pharmacological Basis of Therapeutics*, 11th Edition, 2006, Brunton, Ed., McGraw-Hill; and *Remington: The Science and Practice of Pharmacy*, 21st Edition, 2005, Hendrickson, Ed., Lippincott, Williams & Wilkins).

As used herein, the term "Alzheimer's disease" refers to a progressive disease of the central nervous system in humans and other mammals. It is manifested by dementia (especially in the elderly); disorientation; loss of memory; difficulty with language, calculation, or visual-spatial skills; and psychiatric manifestations. Alzheimer's disease is associated with progressive neurodegeneration and characteristic pathology, namely beta amyloid plaques and tau tangles.

As used herein, the term "osteoarthritis" refers to a chronic degenerative joint disease that results from breakdown of joint cartilage, synovial tissue, and underlying bone.

As used herein, the term "subject" refers to animals such as mammals, including, but not limited to, primates (e.g., humans), cows, sheep, goats, horses, dogs, cats, rabbits, rats, mice and the like.

The term "about," as used herein to modify a numerical value, indicate a close range surrounding that explicit value. If "X" were the value, "about X" would indicate a value from 0.9X to 1.1X, e.g., a value from 0.95X to 1.05X, or a value from 0.98X to 1.02X. Any reference to "about X" specifically indicates at least the values X, 0.95X, 0.96X, 0.97X, 0.98X, 0.99X, 1.01X, 1.02X, 1.03X, 1.04X, and 1.05X. Thus, "about X" is intended to teach and provide written description support for a claim limitation of, e.g., "0.98X."

III. Inhibitors of Arginine Gingipain

In one aspect, the invention provides a compound according to Formula I:

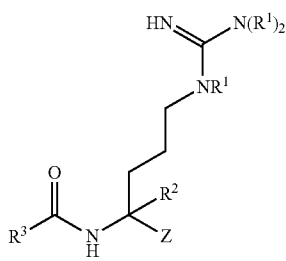

(I)

or a pharmaceutically acceptable salt thereof, wherein:

Z is selected from aryloxymethyl-carbonyl, benzothiazol-2-yl-carbonyl, thiazol-2-yl-carbonyl, oxazol-2-yl-carbonyl, benzooxazol-2-yl-carbonyl, pyridin-2-yl-carbonyl, pyrimidin-4-yl-carbonyl, pyrimidin-2-yl-carbonyl, isoxazol-5-yl-carbonyl, isoxazol-3-yl-carbonyl, 1,2,4-oxadiazol-3-yl-carbonyl, 1,2,4-oxadiazol-5-yl-carbonyl, cyano, ethynyl, fluoromethyl-carbonyl, acyloxymethyl-carbonyl, alkylsulfonyl-vinyl, and arylsulfonyl-vinyl;

wherein Z is optionally substituted with one or more substituents selected from halogen, $C_{1-4}$ alkyl, $C_{1-4}$ alkoxy, $C_{1-4}$ haloalkyl, $C_{1-4}$ haloalkoxy, and —$N_3$;

each $R^1$ is independently selected from hydrogen, $C_{1-4}$ alkyl, and an amine protecting group;

$R^2$ is selected from hydrogen and $C_{1-4}$ alkyl;

$R^3$ is selected from $C_{3-8}$ alkyl, $C_{3-8}$ cycloalkyl, $C_{6-10}$ aryl, 5-to-12 membered heteroaryl, and 5-to-12 membered heterocyclyl, wherein $R^3$ is optionally substituted with one or more $R^4$ substituents independently selected from halo, —CN, —$NO_2$, —$N_3$, —OH, $R^a$, —$OR^b$, —$N(R^d)_2$, —$(CH_2)_kC(O)R^c$, —$NR^d(CH_2)_uC(O)R^c$, —$O(CH_2)_uC(O)R^c$, —$(CH_2)_kCON(R^d)_2$, —$(CH_2)_kNR^dC(O)R$, —$NR^d(CH_2)_uCON(R^d)_2$, —$NR^d(CH_2)_uNR^dC(O)R^c$, —$O(CH_2)_uCON(R^d)_2$, and —$O(CH_2)_uNR^dC(O)R^c$;

each $R^a$, $R^b$, and $R^c$ is independently selected from $C_{1-4}$ alkyl and $C_{1-4}$ haloalkyl, each $R^d$ is independently selected from hydrogen and $C_{1-8}$ alkyl, each subscript k is independently selected from 0, 1, 2, 3, 4, 5, and 6, and each subscript u is independently selected from 1, 2, 3, 4, 5, and 6;

provided that when Z is phenyoxymethylcarbonyl or substituted phenoxymethylcarbonyl, $R^3$ and the carbonyl to which it is bonded form a moiety other than prolinyl, substituted prolinyl, argininyl, substituted argininyl, phenylalaninyl, substituted phenylalaninyl, tert-butylaminocarbonyl, or tert-butyloxycarbonyl; and provided that when Z is benzothiazol-2-yl-carbonyl, $R^3$ is selected from phenyl, trifluromethylphenyl, piperidin-3-yl, pyrrolidin-3-yl, 3-aminocyclopentyl, n-propyl, 3-aminopropyl, and (1-acetamido)propyl.

In some embodiments, the compound of Formula I has a structure according to Formula Ia:

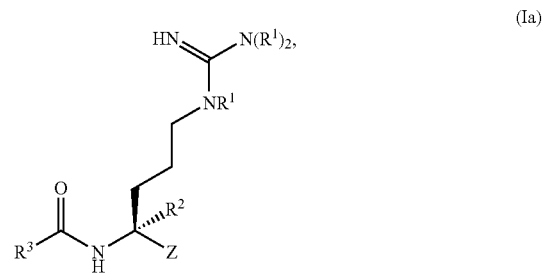

(Ia)

or a pharmaceutically acceptable salt thereof.

In some embodiments, the invention provides compounds of Formula I or Formula Ia, and pharmaceutically acceptable salts thereof, wherein $R^2$ is hydrogen.

In some embodiments, the invention provides compounds of Formula I or Formula Ia, and pharmaceutically acceptable salts thereof, wherein Z is selected from halogen-substituted aryloxymethyl-carbonyl, benzothiazol-2-yl-carbonyl, pyridine-2-yl-carbonyl, and thiazol-2-yl-carbonyl.

In some embodiments, the invention provides compounds of Formula I or Formula Ia, and pharmaceutically acceptable salts thereof, wherein Z is selected from halogen-substituted aryloxymethyl-carbonyl, benzothiazol-2-yl-carbonyl, pyridine-2-yl-carbonyl, and thiazol-2-yl-carbonyl; and wherein $R^2$ is hydrogen. In some embodiments, the invention provides compounds of Formula I or Formula Ia, and pharmaceutically acceptable salts thereof, wherein Z is selected from halogen-substituted aryloxymethyl-carbonyl, benzothiazol-2-yl-carbonyl, pyridine-2-yl-carbonyl, and thiazol-2-yl-carbonyl; and wherein $R^2$ is methyl.

In some embodiments, the invention provides compounds of Formula I or Formula Ia, and pharmaceutically acceptable salts thereof, wherein Z is (2,3,5,6-tetrafluorophenoxymethyl)carbonyl. In some such embodiments, $R^2$ is hydrogen or methyl. In some such embodiments, $R^2$ is hydrogen.

In some embodiments, the compound of Formula I has a structure according to Formula Ib:

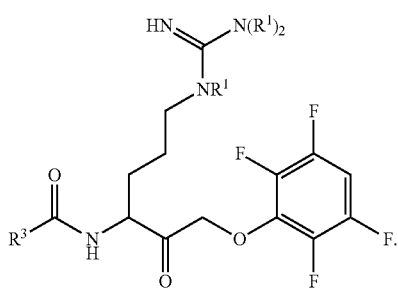

(Ib)

In some embodiments, the invention provides compounds of Formula Ib and pharmaceutically acceptable salts thereof wherein $R^3$ is selected from $C_{3-8}$ cycloalkyl, $C_{6-10}$ aryl, 5-to-12 membered heteroaryl, and 5-to-12 membered heterocyclyl, each of which is optionally substituted with one or more $R^4$ substituents. In some such embodiments, $R^3$ is 5-to-12 membered saturated heterocyclyl. In some such embodiments, $R^3$ is selected from $C_{3-8}$ cycloalkyl and $C_{6-10}$ aryl, each of which is optionally substituted with one or more $R^4$ substituents. In some such embodiments, $R^3$ is selected from cyclopentyl, phenyl, and azidophenyl.

In some embodiments, the invention provides compounds of Formula Ib and pharmaceutically acceptable salts thereof wherein each $R^1$ is an amine protecting group, and $R^3$ is selected from $C_{3-8}$ cycloalkyl, $C_{6-10}$ aryl, 5-to-12 membered heteroaryl, and 5-to-12 membered heterocyclyl, wherein $R^3$ is optionally substituted with one or more $R^4$ substituents. In some such embodiments, $R^3$ is 5-to-12 membered saturated heterocyclyl. In some embodiments, each $R^1$ is an amine protecting group and $R^3$ is selected from $C_{3-8}$ cycloalkyl and $C_{6-10}$ aryl, wherein $R^3$ is optionally substituted with one or more $R^4$ substituents. In some embodiments, each $R^1$ is an amine protecting group and $R^3$ is selected from cyclopentyl, phenyl, and azidophenyl.

In some embodiments, the invention provides compounds of Formula Ib and pharmaceutically acceptable salts thereof wherein each $R^1$ is hydrogen, and $R^3$ is selected from $C_{3-8}$ cycloalkyl, $C_{6-10}$ aryl, 5-to-12 membered heteroaryl, and 5-to-12 membered heterocyclyl, wherein $R^3$ is optionally substituted with one or more $R^4$ substituents. In some such embodiments, $R^3$ is 5-to-12 membered saturated heterocyclyl. In some embodiments, each $R^1$ is hydrogen and $R^3$ is selected from $C_{3-8}$ cycloalkyl and $C_{6-10}$ aryl, wherein $R^3$ is optionally substituted with one or more $R^4$ substituents. In some embodiments, each $R^1$ is hydrogen and $R^3$ is selected from cyclopentyl, phenyl, and azidophenyl.

In some embodiments, the compound of Formula Ib is selected from:

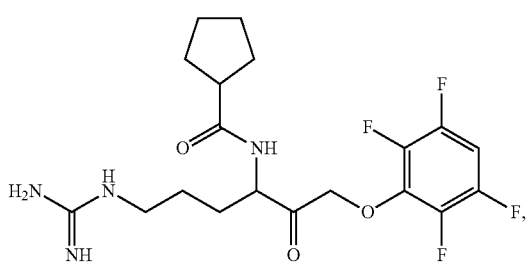

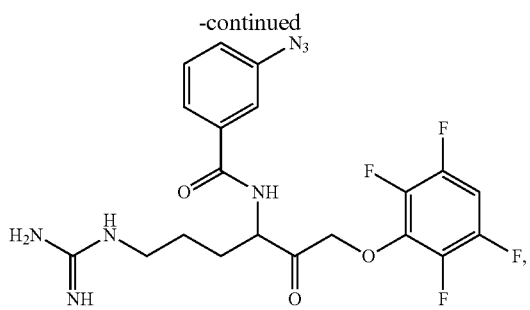

and pharmaceutically acceptable salts thereof.

In some embodiments, the compound of Formula Ib is selected from:

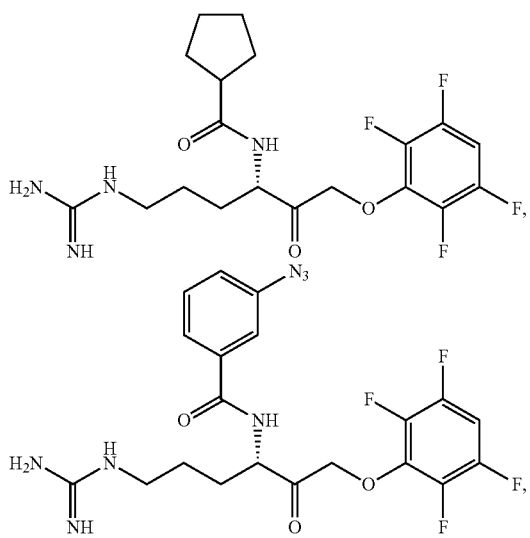

and pharmaceutically acceptable salts thereof.

In some embodiments, the compound of Formula Ib is

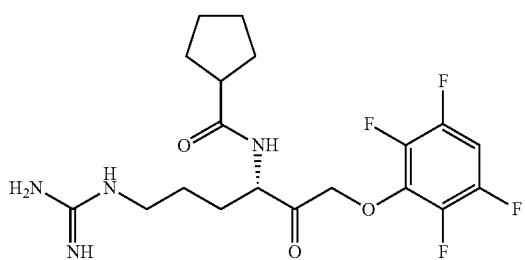 [SMILES: N=C(N)NCCC[C@H](NC(=O)C1CCCC1)C(=O)COc1c(F)c(F)cc(F)c1F]

or a pharmaceutically acceptable salt thereof.

In some embodiments, the invention provides compounds of Formula I or Formula Ia, and pharmaceutically acceptable salts thereof, wherein Z is selected from thiazol-2-yl-carbonyl, oxazol-2-yl-carbonyl, benzooxazol-2-yl-carbonyl, pyridin-2-yl-carbonyl, pyrimidin-4-yl-carbonyl, pyrimidin-2-yl-carbonyl, isoxazol-5-yl-carbonyl, isoxazol-3-yl-carbonyl, 1,2,4-oxadiazol-3-yl-carbonyl, 1,2,4-oxadiazol-5-yl-carbonyl, maleimidyl, pyridinyldisulfanyl (including pyridin-2-yldisulfanyl), cyano, ethynyl, fluoromethyl-carbonyl, acyloxymethyl-carbonyl, aryloxymethyl-carbonyl, alkylsulfonyl-vinyl, and arylsulfonyl-vinyl. In some such embodiments, $R^2$ is hydrogen or methyl. In some such embodiments, $R^2$ is hydrogen.

In some embodiments, the invention provides a compound having a structure according to Formula Ic:

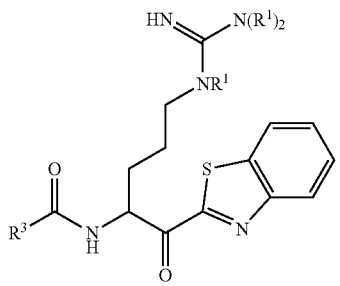
(Ic)

or a pharmaceutically acceptable salt thereof, wherein $R^3$ is selected from phenyl, trifluromethylphenyl, piperidin-3-yl, pyrrolidin-3-yl, 3-aminocyclopentyl, n-propyl, 3-aminopropyl, and (1-acetamido)propyl.

In some embodiments, the invention provides compounds wherein each $R^1$ is an amine protecting group, and wherein $R^3$ is selected from phenyl, trifluromethylphenyl, piperidin-3-yl, pyrrolidin-3-yl, 3-aminocyclopentyl, n-propyl, 3-aminopropyl, and (1-acetamido)propyl. In some embodiments, the invention provides compounds wherein each $R^1$ is hydrogen, and wherein $R^3$ is selected from phenyl, trifluromethylphenyl, piperidin-3-yl, pyrrolidin-3-yl, 3-aminocyclopentyl, n-propyl, 3-aminopropyl, and (1-acetamido)propyl.

In some embodiments, the compound of Formula Ic is selected from

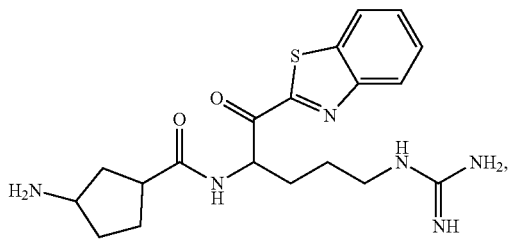

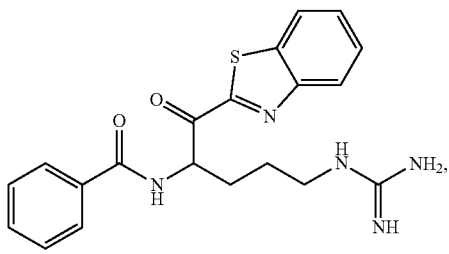

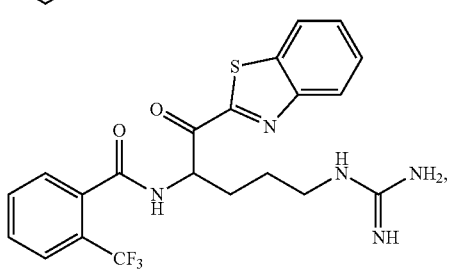

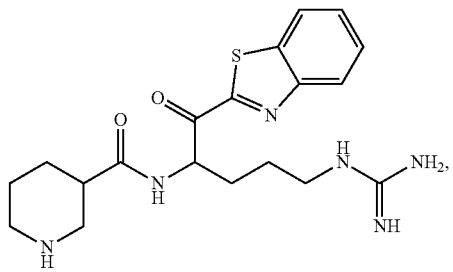

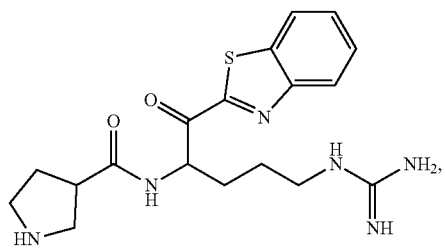

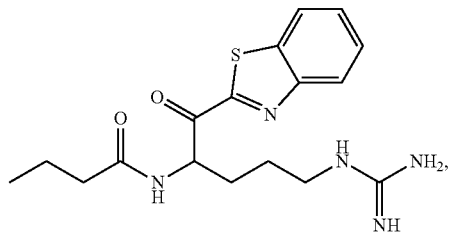

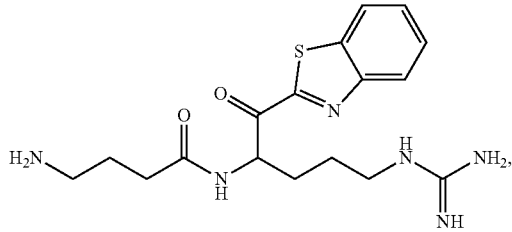

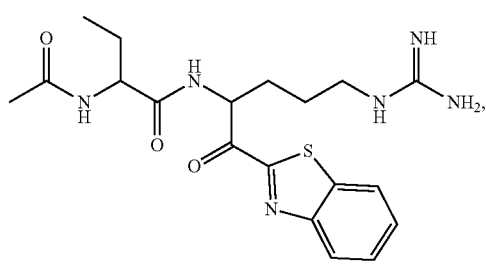 [SMILES: CCC(NC(C)=O)C(=O)NC(CCCNC(=N)N)C(=O)c1nc2ccccc2s1]

and pharmaceutically acceptable salts thereof.

In some embodiments, the compound of Formula Ic is selected from

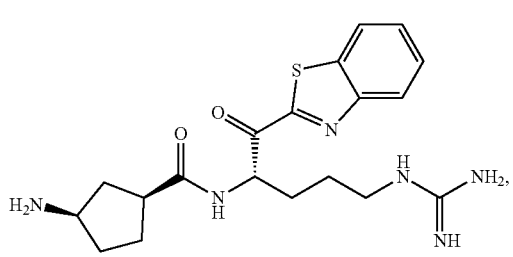

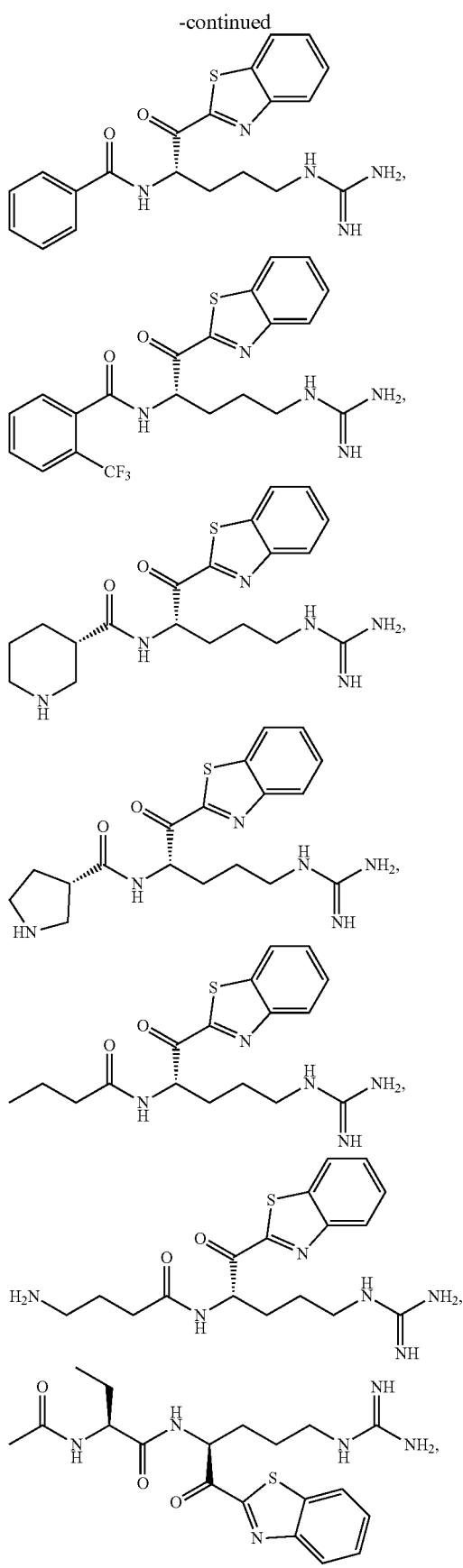

In some embodiments, the invention provides compounds of Formula I, Formula Ia, or Formula Ib wherein Z is selected from thiazol-2-yl-carbonyl, pyridin-2-yl-carbonyl, cyano, ethynyl, and fluoromethylcarbonyl, including compounds according to Formula IIIa, Formula IIIb, Formula IIIc, Formula IIId, and Formula IIIe.

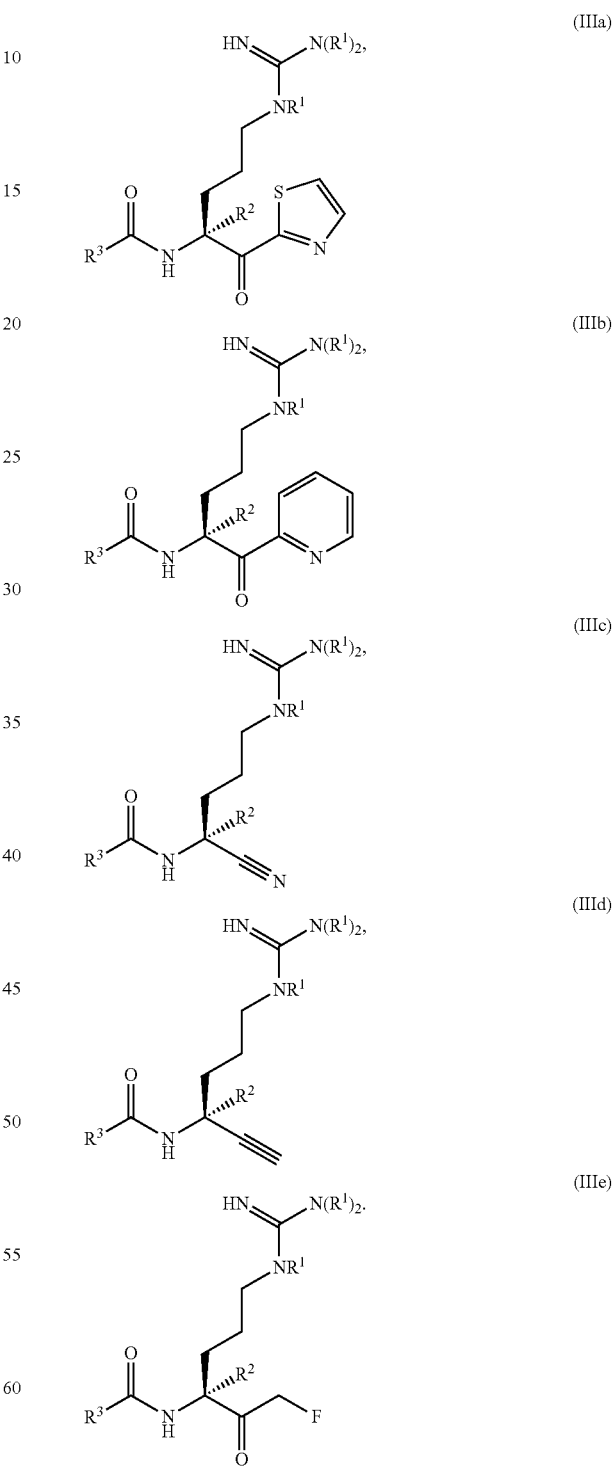

The compounds described herein and methods of using them encompass the preparation and use of therapeutically active enantiomers or diastereomers of the described compounds. All such enantiomers and diastereomers of these compounds are included in the scope of the invention. Such compounds can be used as mixtures (e.g., racemic mixtures) or as isolated enantiomers or diastereomers. When a stereochemical depiction is shown, it is meant to refer the compound in which one of the isomers is present and substantially free of the other isomer. "Substantially free of" another isomer indicates at least a 60/40 ratio of the two isomers (e.g., 65/35, 70/30, 75/25, 80/20, 85/75, 90/10, or 95/5, or a larger ratio). In some embodiments, one of the isomers will be present in an amount of at least 99%.

Compounds of the invention can be prepared so as to include radionuclides for use in diagnostic imaging application such as positron emission tomography (PET) and single-photon emission computed tomography (SPECT). For example, Rgp inhibitors as described herein can be prepared so as to include one or more radionuclides selected from oxygen-15 ($^{15}O$), nitrogen-13 ($^{13}N$), carbon-11 ($^{11}C$), iodine-131 ($^{131}I$), and fluorine-18 ($^{18}F$). Such radiolabeled compounds can be used for PET imagining. Compounds of the invention can also be prepared in deuterated form (i.e., having one or more deuterium atoms, $^2H$, in place of one more hydrogen atoms), tritiated form (i.e., having one or more tritium atoms, $^3H$, in place of one more hydrogen atoms), or $^{14}C$-labeled form (i.e., having one or more $^{14}C$ atoms in place of one more carbon atoms).

In general, when Z is phenyoxymethylcarbonyl or substituted phenoxymethyl-carbonyl in compounds according to Formula I, $R^3$ and the carbonyl to which it is bonded form a moiety other than prolinyl, substituted prolinyl, argininyl, substituted argininyl, phenylalaninyl, substituted phenylalaninyl, tert-butylaminocarbonyl, or tert-butyloxycarbonyl. Accordingly, the invention provides compounds of Formula I which are not compounds of Formula Ip, Iq, Ir, Is, or It:

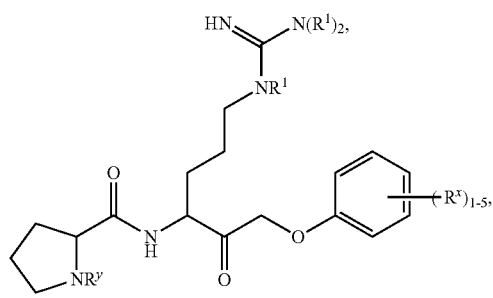

(Ip)

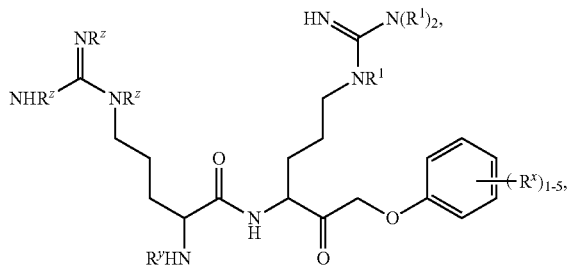

(Iq)

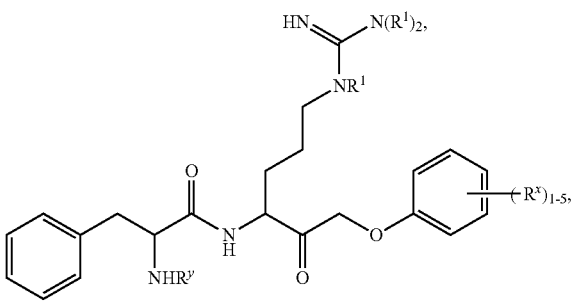

(Ir)

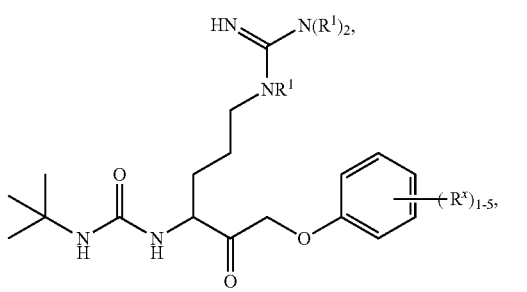

(Is)

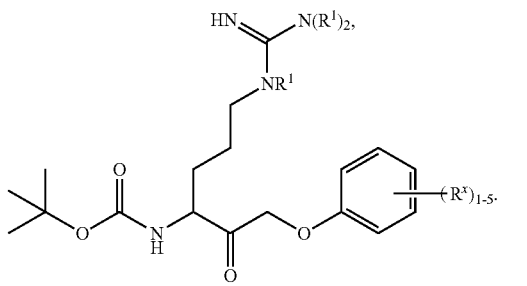

(It)

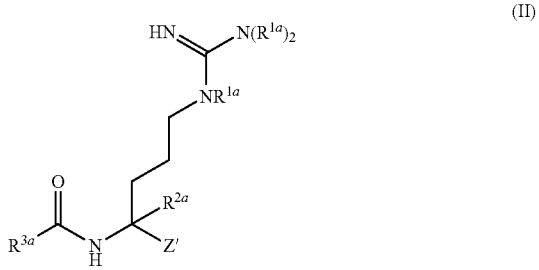

In compounds of Formula Ip, Iq, Ir, Is, and It, each $R^1$ is independently selected from hydrogen, $C_{1-4}$ alkyl, and an amine protecting group; each $R^x$ is independently selected from $C_{1-4}$ alkyl, $C_{1-4}$ alkoxy, $C_{1-4}$ haloalkyl, $C_{1-4}$ haloalkoxy, and halogen; $R^y$ is selected from hydrogen, $C_{1-4}$ alkyl, amido, acyl, an amine protecting group, and an amino acid residue; and each $R^z$ is independently selected from hydrogen, $C_{1-4}$ alkyl, and an amine protecting group.

In further embodiments, the invention provides compounds according to Formula II:

(II)

or a pharmaceutically acceptable salt thereof, wherein:
Z' is selected from aryloxymethyl-carbonyl, benzothiazol-2-yl-carbonyl, thiazol-2-yl-carbonyl, oxazol-2-yl-carbonyl, benzooxazol-2-yl-carbonyl, pyridin-2-yl-carbonyl, pyrimidin-4-yl-carbonyl, pyrimidin-2-yl-carbonyl, isoxazol-5-yl-carbonyl, isoxazol-3-yl-carbonyl, 1,2,4-oxadiazol-3-yl-carbonyl, 1,2,4-oxadiazol-5-yl-carbonyl, cyano, ethynyl, fluoromethyl-carbonyl, acyloxymethyl-carbonyl, alkylsulfonyl-vinyl, and arylsulfonyl-vinyl;

wherein Z' is optionally substituted with one or more substituents selected from halogen, $C_{1-4}$ alkyl, $C_{1-4}$ alkoxy, $C_{1-4}$ haloalkyl, $C_{1-4}$ haloalkoxy, and —$N_3$;

each $R^{1a}$ is independently selected from hydrogen, $C_{1-4}$ alkyl, and an amine protecting group;

$R^{2a}$ is selected from hydrogen and $C_{1-4}$ alkyl;

$R^{3a}$ is selected from $C_{3-8}$ cycloalkyl, $C_{3-8}$ alkyl, $C_{6-10}$ aryl, 5-to-12 membered heteroaryl, and 5-to-12 membered heterocyclyl, wherein $R^{3a}$ is optionally substituted with one or more $R^{4a}$ substituents independently selected from halo, —CN, —$NO_2$, —$N_3$, —OH, $R^a$, —$OR^b$, —$N(R^d)_2$, —$(CH_2)_kC(O)R^c$, —$NR^d(CH_2)_uC(O)R^c$, —$O(CH_2)_uC(O)R^c$, —$(CH_2)_kCON(R^d)_2$, —$(CH_2)_kNR^dC(O)R^c$, —$NR^d(CH_2)_uCON(R^d)_2$, —$NR^d(CH_2)_uNR^dC(O)R^c$, —$O(CH_2)_uCON(R^d)_2$, and —$O(CH_2)_uNR^dC(O)R^c$;

each $R^a$, $R^b$, and $R^c$ is independently selected from $C_{1-4}$ alkyl and $C_{1-4}$ haloalkyl, each $R^d$ is independently selected from hydrogen and $C_{1-8}$ alkyl, each subscript k is independently selected from 0, 1, 2, 3, 4, 5, and 6, and each subscript u is independently selected from 1, 2, 3, 4, 5, and 6.

In some embodiments, the compound of Formula II is a compound having a structure according to Formula IIa:

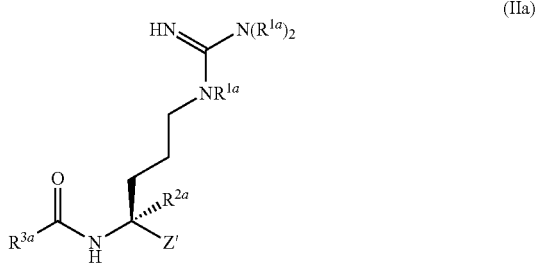

(IIa)

or a pharmaceutically acceptable salt thereof. In some such embodiments, $R^{2a}$ is selected from hydrogen and methyl. In some such embodiments, $R^{2a}$ is hydrogen.

The compounds of the invention are highly active Rgp inhibitors, typically exhibiting Rgp Ki values and Rgp $IC_{50}$ values well below 1 μM.

The term "Ki" refers to inhibition constant. The Ki value for a particular test compound can be measured as follows. Fifty microliters (μL) of an enzyme such as RgpA or RgpB (1 nM in 50 mM bis-Tris propane [pH 8.0] containing 1% [vol/vol] Triton X-100 and 5 mM 2-mercaptoethanol) is added to columns 1 to 11 of a 96-well plate, and 100 μL is added to column 12. Two μL of the test compound (100 μL in 100% DMSO) is added to column 12, and the sample is mixed three times by pipetting. Then, a doubling dilution is prepared across the plate by serial transfer into adjacent wells. 50 μL of Z-Arg-7-amido-4-methylcoumarin ("Z-Arg-AMC;" 40 μM in buffer) is added to all wells, and the contents are mixed. The reaction is monitored for AMC fluorescence for 15 min at 25° C., and the progress curves are automatically converted to rates by the Fluoroskan Ascent software.

The method can be used to assay enzymes including Kgp, RgpB, RgpA, trypsin, and cathepsin B. For Kgp, the substrate can be succinyl-Ala-Phe-Lys-AMC. For trypsin, the buffer can contain 10 mM Tris and 10 mM $CaCl_2$) (pH 8.0), and the substrate can be Z-Gly-Gly-Arg-AMC. For cathepsin B, the buffer can contain 50 mM sodium phosphate, 1 mM EDTA, and 10 mM 2-mercaptoethanol (pH 6.25), and the substrate can be Z-Arg-Arg-AMC.

The inhibition constants can then be calculated by using the following equation, with an assumption that inhibition is fully competitive:

$$V_i=(V_{max}[S])/([S]+K_m(1+[I]/K_i)$$

where $V_i$ is the observed residual activity, [S] is the substrate concentration used in the assay, $V_{max}$ is the maximal velocity at an inhibitor concentration of zero, $K_i$ is the inhibitor dissociation constant, and [I] is the inhibitor concentration. Curves can then be fitted by nonlinear regression analysis by using fixed values for the substrate concentration and the value of the Michaelis constant ($K_m$). Data analysis can be carried out by using Prism v 2.01 (GraphPad, San Diego, Calif.).

The term "$IC_{50}$" indicates how much of a compound is needed to inhibit a given biological process (or component of a process, e.g., an enzyme, cell, cell receptor, or microorganism) by one half (50%). The $IC_{50}$ of a compound can be determined by constructing a dose-response curve and examining the effect of different concentrations of the compound on reversing the activity of the enzyme. From the dose-response curve, $IC_{50}$ values can be calculated for a given compound by determining the concentration needed to inhibit half of the maximum biological response of the enzyme.

In general, the Rgp Ki value for compounds of the invention ranges from about 0.001 nM to about 500 nM. The Rgp Ki value for a compound of the invention can range, for example, from about 1 nM to about 20 nM, or from about 20 nM to about 40 nM, or from about 40 nM to about 60 nM, or from about 60 nM to about 80 nM, or from about 80 nM to about 100 nM, or from about 100 nM to about 150 nM, or from about 150 nM to about 200 nM, or from about 200 nM to about 250 nM, or from about 250 nM to about 300 nM, or from about 300 nM to about 350 nM, or from about 350 nM to about 400 nM, or from about 400 nM to about 450 nM, or from about 450 nM to about 500 nM. The Rgp Ki value for a compound of the invention can range from about 0.001 nM to about 0.025 nM, or from about 0.025 nM to about 0.050 nM, or from about 0.050 nM to about 0.075 nM, or from about 0.075 nM to about 0.100 nM, or from about 0.100 nM to about 0.250 nM, or from about 0.250 nM to about 0.500 nM, or from about 0.500 nM to about 0.750 nM, or from about 0.750 nM to about 1 nM.

In general, the Rgp $IC_{50}$ value for compounds of the invention ranges from about 0.001 nM to about 500 nM. The Rgp IC50 value for a compound of the invention can range, for example, from about 1 nM to about 20 nM, or from about 20 nM to about 40 nM, or from about 40 nM to about 60 nM, or from about 60 nM to about 80 nM, or from about 80 nM to about 100 nM, or from about 100 nM to about 150 nM, or from about 150 nM to about 200 nM, or from about 200 nM to about 250 nM, or from about 250 nM to about 300 nM, or from about 300 nM to about 350 nM, or from about 350 nM to about 400 nM, or from about 400 nM to about 450 nM, or from about 450 nM to about 500 nM. The Rgp IC50 value for a compound of the invention can range from about 0.001 nM to about 0.025 nM, or from about 0.025 nM to about 0.050 nM, or from about 0.050 nM to about 0.075 nM, or from about 0.075 nM to about 0.100 nM, or from about 0.100 nM to about 0.250 nM, or from about 0.250 nM to about 0.500 nM, or from about 0.500 nM to about 0.750 nM, or from about 0.750 nM to about 1 nM.

In some embodiments, an Rgp inhibitor according to the invention has an RgpB Ki of 100 nM or less. In some embodiments, the Rgp inhibitor has an RgpB Ki of 50 nM or less.

In some embodiments, an Rgp inhibitor according to the invention has an RgpB $IC_{50}$ of 50 nM or less. In some embodiments, the Rgp inhibitor has an RgpB $IC_{50}$ of 15 nM or less. In some embodiments, the Rgp inhibitor has an RgpB $IC_{50}$ of 100 pM or less. In some embodiments, the Rgp inhibitor has an RgpB $IC_{50}$ of 20 pM or less.

Compounds having Rgp Ki values of 15 nM or less can be particularly useful for systemic administration. For example, such compounds can have Rgp Ki values ranging from about 1 picomolar (pM) to about 15 nanomolar (nM), from about 10 pM to about 12 nM, from about 100 pM to about 11 nM, or from about 100 pM to about 10 nM. Such compounds can have Rgp Ki values of less than 10 nanomolar (nM), less than 8 nM, less than 6 nM, or less than 4 nM.

Compounds having Rgp Ki values of 45 nM or less can be particularly useful for topical administration. For example, such compounds can have Rgp Ki values ranging from about 1 picomolar (pM) to about 40 nanomolar (nM), from about 10 pM to about 35 nM, from about 100 pM to about 30 nM, or from about 100 pM to about 25 nM.

In certain embodiments, Rgp inhibitors according to the invention are selective for Rgp. As used herein, a "selective" Rgp inhibitor is a compound that does not substantially affect the activity of proteases other than RgpA and RgpB when administered at a therapeutically effective dose for treating a disease or condition associated with *P. gingivalis* infection. Typically, a protease that is not substantially affected by a particular compound exhibits at least 90% of its normal enzymatic activity in the presence of the compound under physiological conditions. Selective Rgp inhibitors include those compounds that do not affect the activity of proteases other than Rgp when administered at a therapeutically effective dose for treating a brain disorder, periodontal disease, diabetes, a cardiovascular disease, arthritis, rheumatoid arthritis, osteoarthritis, infectious arthritis, psoriatic arthritis, preterm birth, pneumonia, cancer, a kidney disease, a liver disease, a retinal disorder, or glaucoma associated with *P. gingivalis* infection. Preferably, selective Rgp inhibitors do not adversely affect the coagulation cascade when administered at therapeutically effective levels.

In some embodiments, the invention provides an Rgp inhibitor having an RgpB Ki of less than 50 nM. In some such embodiments, the trypsin Ki is greater than 60 nM. In the some embodiments, the Rgp inhibitor has a Ki for RgpB of less than 15 nM, and a (trypsin Ki)/(RgpB Ki) ratio of greater than 100.

In some embodiments, the invention provides compounds that are at least 30 times more selective for Rgp than for trypsin or cathepsin B. For some such compounds, the RgpB Ki is less than 1 nM, and the trypsin Ki and/or the cathepsin B Ki are 30 nM or more. In some embodiments, the RgpB Ki is less than 1 nM, and the trypsin Ki and/or the cathepsin B Ki are 115 µM or more. For some such compounds, the RgpB $IC_{50}$ is 15 nM or less and the trypsin $IC_{50}$ trypsin is 1 µM or more.

IV. Methods for Preparing Rgp Inhibitors

Certain examples of compounds of Formula I can be prepared starting with certain arginine derivatives IVa and IVb, which are described below and are commercially available or can be prepared according to known procedures.

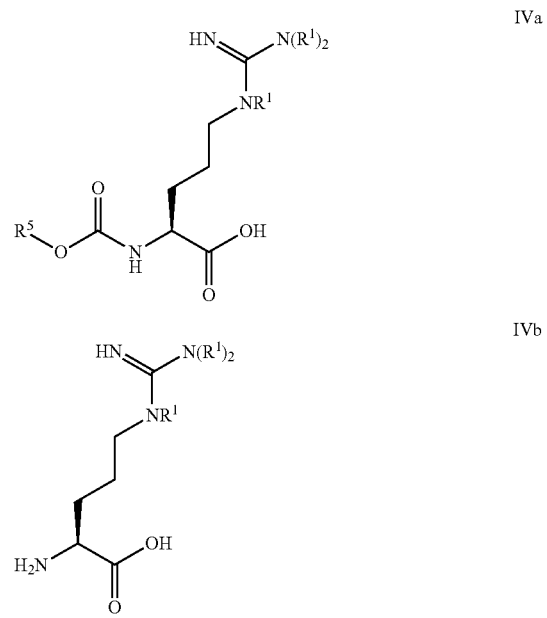

IVa

IVb

In IVa, $R^5$ and $R^1$ each can be removed by chemical conditions that do not remove the other. For example, $R^5$=benzyl can be removed by hydrogen and a palladium-carbon catalyst, but $R^5$ is not affected by trifluoroacetic acid, whereas $R^1$=t-butyl can be removed by trifluoroacetic acid, but $R^1$ is not affected by hydrogen and a palladium-carbon catalyst. Alternatively, $R^5$=Boc can be removed using hydrochloric acid without removing $R^1$=Pbf. Other appropriate, complimentary combinations of $R^5$ and $R^1$ are known to those of skill in the art. Similarly, in IVb, several appropriate combinations of complimentary, removable $R^1$ and $R^6$ group are known.

Certain compounds according to Formula VIII can be prepared by a sequence of transformations from IVa to V to VI to VII to VIII. See, Scheme 1.

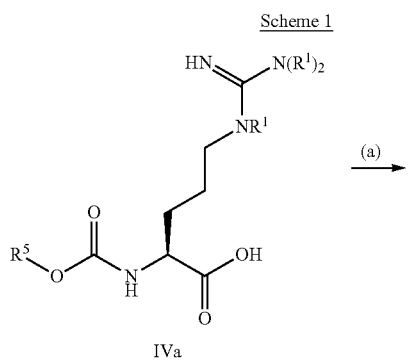

Scheme 1

IVa

-continued

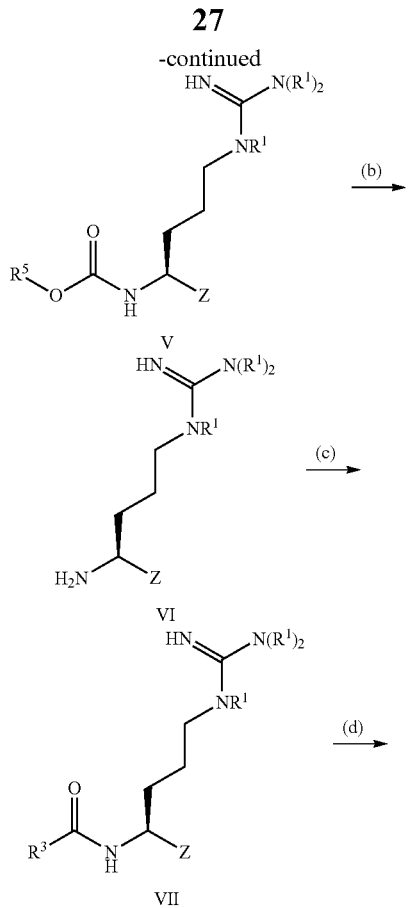

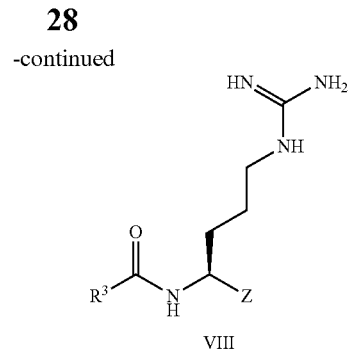

In most instances, the transformation of IVa to V will involve more than one chemical reaction. Various conditions can be applied to transform IVa to V. IVa can be converted to Va-1 by treatment with N-methyl-O-methylhydroxylamine hydrochloride, an organic base (for example Et3N), a racemization inhibitor (for example HOBt), and a dehydrating agent (for example EDAC), in an organic solvent (for example DMF). See, Scheme 2, step (a). Va-1 can be converted to Va by treatment with a lithiated heterocycle (for example 2-lithiobenzothiazole, 2-lithiothiazole, or 2-lithiopyridine), in an organic solvent (for example THF), to install the corresponding $R^7$ (2-benzothiazolyl, 2-thiazolyl, or 2-pyridyl). See, Scheme 2, step (b).

Scheme 2

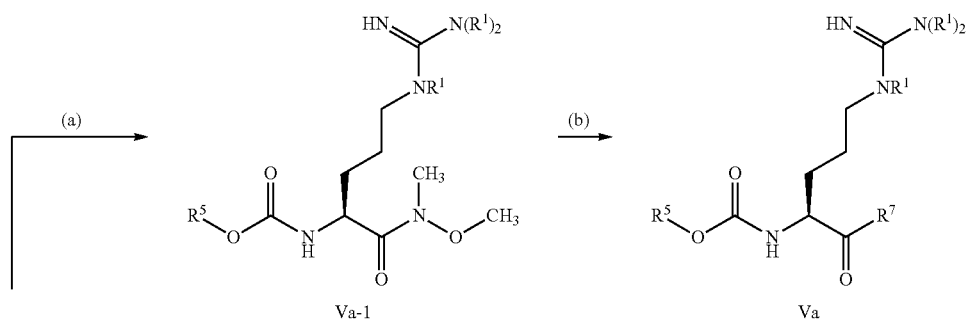

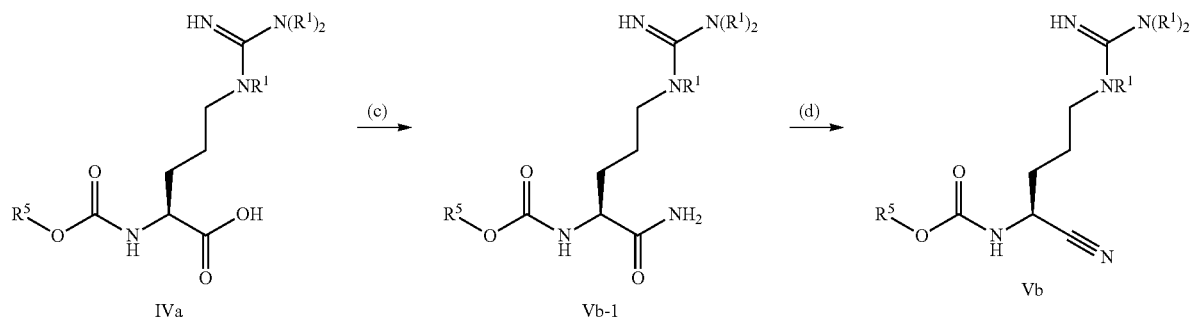

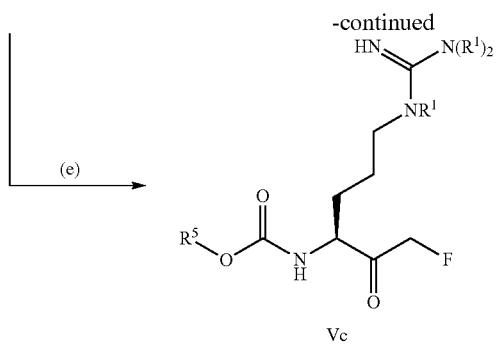

IVa can be converted to Vb-1 by treatment with ammonium hydrochloride, an organic base (for example Et3N), a racemization inhibitor (for example HOBt), and a dehydrating agent (for example EDAC), in an organic solvent (for example DMF). See, Scheme 2, step (c). Vb-1 can be converted to Vb by treatment with an organic base (for example Et₃N), and a strong dehydrating agent (for example pyridine-sulfur trioxide complex), in an organic solvent (for example CH₂Cl₂). See, Scheme 2, step (d).

IVa can be converted to Vc by treatment with fluoroacetic anhydride, an organic base (for example Et3N), and DMAP in an organic solvent (for example DMF). See, Scheme 2, step (e).

IVa can be converted to Vd-2 by treatment with borane-dimethylsulfide complex in an organic solvent (for example THF). See, Scheme 3, step (a). Vd-2 can be converted to Vd-1 by treatment with an organic base (for example Et3N), a strong dehydrating agent (for example oxalyl chloride), and dimethylsulfoxide, in an organic solvent (for example CH₂Cl₂). See, Scheme 3, step (b). Vd-1 can be converted to Vd by treatment with trimethyl diazo phosphonacetate and K₂CO₃ in an alcohol solvent (for example methanol). See, Scheme 3, step (c).

Scheme 3

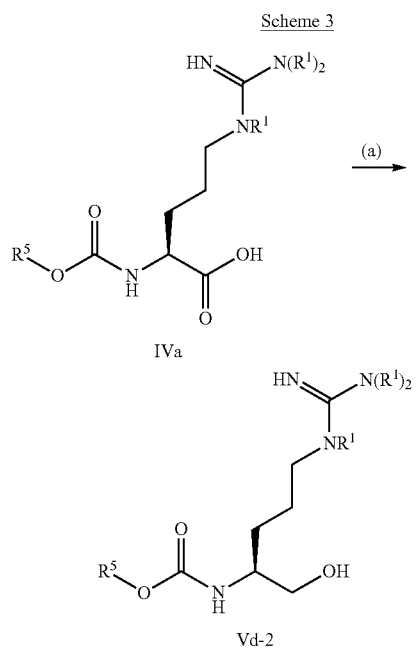

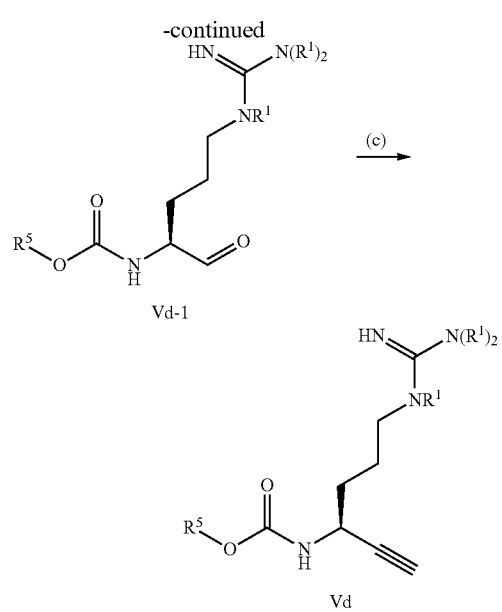

IVa can be converted to Ve-2 by treatment with an organic base (for example Et3N), a chloroformate (for example EtO₂CCl), and diazomethane in an organic solvent (for example diethyl ether). See, Scheme 4, step (a). Ve-2 can be converted to Ve-1 by treatment with HBr and acetic acid in an organic solvent (for example THF). See, Scheme 4, step (b). Ve-1 can be converted to Ve by treatment with an alcohol HOR[8] (for example 2,3,5,6-tetrafluorophenol) and KF in an organic solvent (for example DMF), to install the corresponding —OR[8] (for example 2,3,5,6-tetrafluorophenoxy). See, Scheme 4, step (c).

Scheme 4

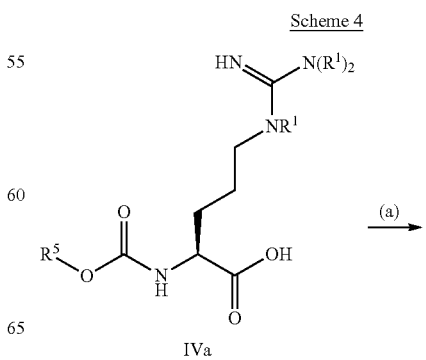

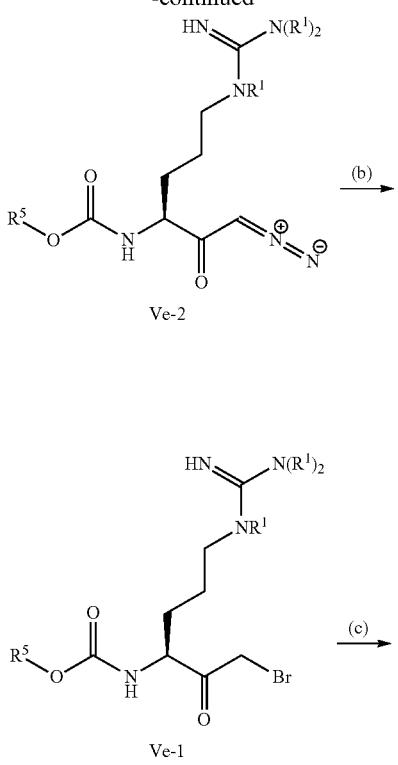

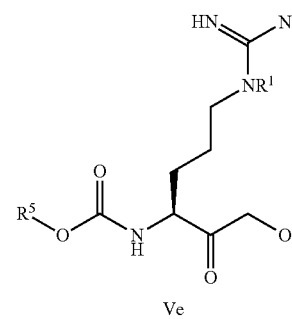

Scheme 5

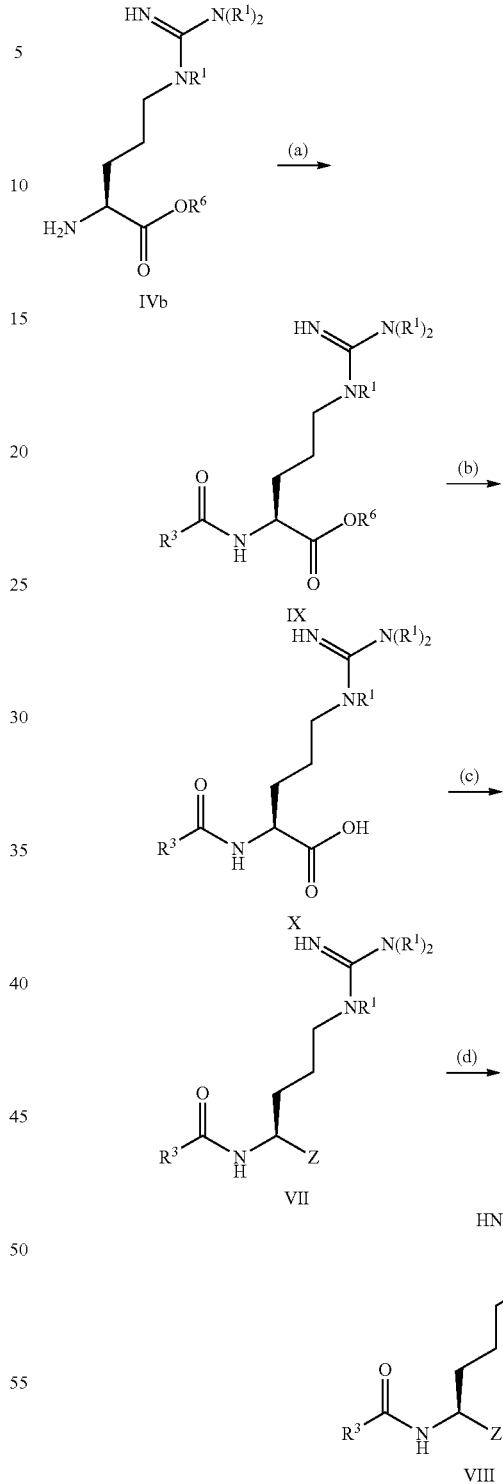

After transformation of IVa to V (e.g., to Va, Vb, Vc, Vd, or Ve), $R^5$ can be removed by appropriate chemical conditions, generating VI after spontaneous decarboxylation. VI or a salt of VI (e.g., the hydrochloride salt of VI) can be used in further synthetic steps. VI can be treated with a carboxylic acid $R^3CO_2H$, and a racemization inhibitor (for example HOBt), and a dehydrating agent (for example EDAC), in an organic solvent (for example DMF), generating VII. Alternatively, VI can be treated with $R^3COR'$, wherein R' is a leaving group (for example chloride), and an organic base (for example Et3N), in an organic solvent (for example $CH_2Cl_2$), generating VII. A wide variety of applicable $R^3CO_2H$ and $R^3COR'$ compounds are commercially available, or can be prepared by known methods. $R^1$ groups can be removed from VII by appropriate chemical conditions, generating VIII.

Other compounds according to Formula VIII can be prepared by a sequence of transformations from IVb to IX to X to VII to VIII. See, Scheme 5.

IVb can be treated with a carboxylic acid $R^3CO_2H$, and a racemization inhibitor (for example HOBt), and a dehydrating agent (for example EDAC), in an organic solvent (for example DMF), generating IX. See, Scheme 5, step (a). Alternatively, IVb can be treated with $R^3COR'$, wherein R' is a leaving group (for example chloride), and an organic base (for example Et3N), in an organic solvent (for example

33

CH$_2$Cl$_2$), generating IX. A wide variety of applicable R$^3$CO$_2$H and R$^3$COR' compounds are commercially available, or can be prepared by known methods. R$^6$ can be removed from IX by appropriate chemical conditions generating X. See, Scheme 5, step (b).

X can be transformed to VII by sequences of reactions similar to those described for transformation of IVa to Va, Vb, Vc, Vd, or Ve. See, Scheme 5, step (c). In some embodiments, X is transformed to VIIe as shown in Scheme 6, steps (a)-(c). In some embodiments, —OR$^8$ in VIIe and VIIIe is 2,3,5,6-tetrafluorophenoxy.

Scheme 6

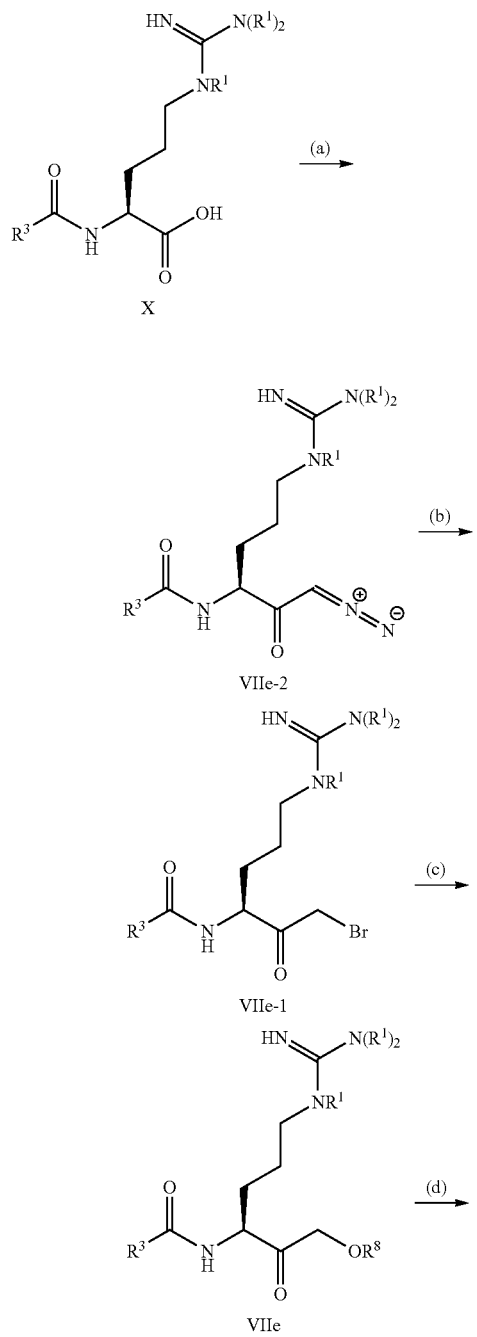

34

-continued

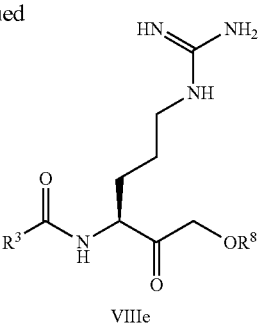

VIIIe

Following the alternative sequences to VII, R$^1$ can be removed by appropriate chemical conditions, generating VIII. See, Scheme 5 and Scheme 6, step (d).

V. Pharmaceutical Compositions and Administration of Arginine Gingipain Inhibitors In a related aspect, the invention provides a pharmaceutical composition comprising a compound of Formula I and a pharmaceutically acceptable excipient.

The pharmaceutical compositions can be prepared by any of the methods well known in the art of pharmacy and drug delivery. In general, methods of preparing the compositions include the step of bringing the active ingredient into association with a carrier containing one or more accessory ingredients. The pharmaceutical compositions are typically prepared by uniformly and intimately bringing the active ingredient into association with a liquid carrier or a finely divided solid carrier or both, and then, if necessary, shaping the product into the desired formulation. The compositions can be conveniently prepared and/or packaged in unit dosage form.

Pharmaceutical compositions containing compounds of the invention can be formulated for oral use. Suitable compositions for oral administration include, but are not limited to, tablets, troches, lozenges, aqueous or oily suspensions, dispersible powders or granules, emulsions, hard or soft capsules, syrups, elixirs, solutions, buccal patches, oral gels, chewing gums, chewable tablets, effervescent powders, and effervescent tablets. Compositions for oral administration can be formulated according to any method known to those of skill in the art. Such compositions can contain one or more agents selected from sweetening agents, flavoring agents, coloring agents, antioxidants, and preserving agents in order to provide pharmaceutically elegant and palatable preparations.

Tablets generally contain the active ingredient in admixture with non-toxic pharmaceutically acceptable excipients, including: inert diluents, such as cellulose, silicon dioxide, aluminum oxide, calcium carbonate, sodium carbonate, glucose, mannitol, sorbitol, lactose, calcium phosphate, and sodium phosphate; granulating and disintegrating agents, such as corn starch and alginic acid; binding agents, such as polyvinylpyrrolidone (PVP), cellulose, polyethylene glycol (PEG), starch, gelatin, and acacia; and lubricating agents such as magnesium stearate, stearic acid, and talc. The tablets can be uncoated or coated, enterically or otherwise, by known techniques to delay disintegration and absorption in the gastrointestinal tract and thereby provide a sustained action over a longer period. For example, a time delay material such as glyceryl monostearate or glyceryl distearate can be employed. Tablets can also be coated with a semipermeable membrane and optional polymeric osmogents according to known techniques to form osmotic pump compositions for controlled release.

Compositions for oral administration can be formulated as hard gelatin capsules wherein the active ingredient is mixed with an inert solid diluent (such as calcium carbonate, calcium phosphate, or kaolin), or as soft gelatin capsules wherein the active ingredient is mixed with water or an oil medium (such as peanut oil, liquid paraffin, or olive oil).

Rgp inhibitors can also be administered topically as a solution, ointment, cream, gel, or suspension, as well as in mouth washes, eye-drops, and the like. Still further, transdermal delivery of Rgp inhibitors can be accomplished by means of iontophoretic patches and the like.

Pharmaceutical compositions containing Rgp inhibitors can also be in the form of a sterile injectable aqueous or oleaginous solutions and suspensions. Sterile injectable preparations can be formulated using non-toxic parenterally-acceptable vehicles including water, Ringer's solution, and isotonic sodium chloride solution, and acceptable solvents such as 1,3-butane diol. In addition, sterile, fixed oils can be used as a solvent or suspending medium. For this purpose any bland fixed oil can be employed including synthetic monoglycerides, diglycerides, or triglycerides.

Figure 8:
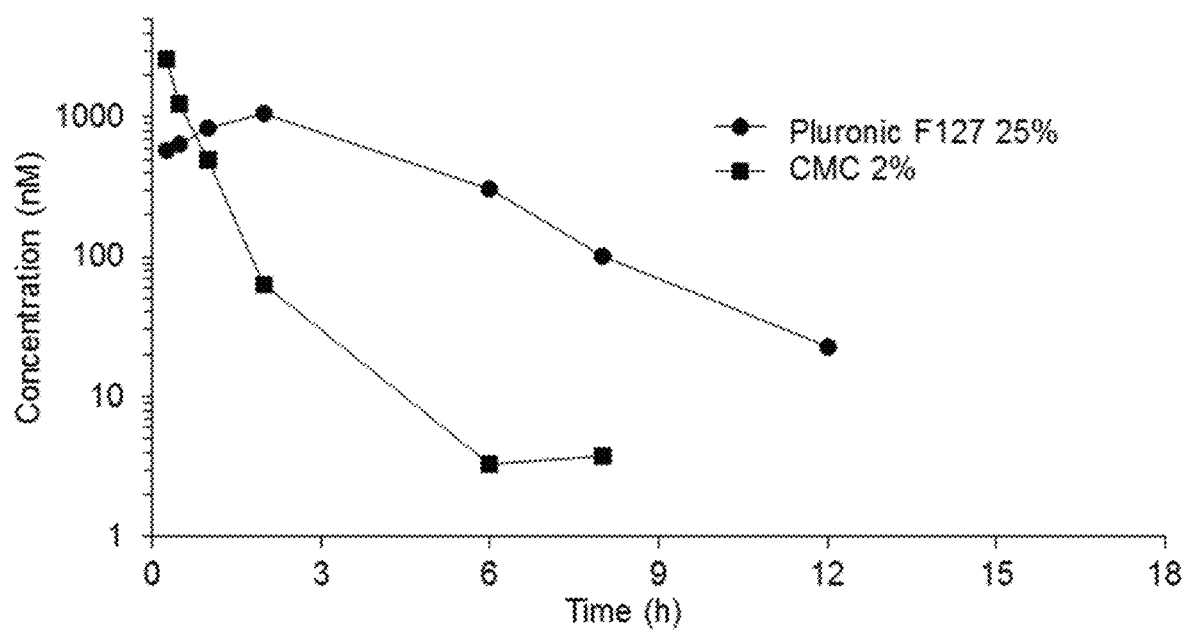
FIG. 8 shows the plasma concentration resulting from subcutaneous administration of Compound 13 (10 mg/kg) to mice in 2% carboxymethylcellulose (closed squares) or 25% Pluronic F127 (closed circles).

In some embodiments, an Rgp inhibitor can be formulated with a polymer such as Pluronic F127 and delivered subcutaneously. Pluronic is a hydrogel that solidifies at body temperature and provided extended drug delivery over periods of time lasting from days to weeks. FIG. 8 shows that the AUC(0-last) of Compound 13 extends from 687 ng·h/mL when delivered in 2% carboxymethylcellulose to 2119 ng·h/mL when delivered in 25% Pluronic F127.

Aqueous suspensions can contain one or more Rgp inhibitors in admixture with excipients including, but not limited to: suspending agents such as sodium carboxymethylcellulose, methylcellulose, oleagino-propylmethylcellulose, sodium alginate, polyvinyl-pyrrolidone, gum tragacanth and gum acacia; dispersing or wetting agents such as lecithin, polyoxyethylene stearate, and polyethylene sorbitan monooleate; and preservatives such as ethyl, n-propyl, and p-hydroxybenzoate. Dispersible powders and granules (suitable for preparation of an aqueous suspension by the addition of water) can contain one or more Rgp inhibitors in admixture with a dispersing agent, wetting agent, suspending agent, or combinations thereof. Oily suspensions can be formulated by suspending an Rgp inhibitor in a vegetable oil (e.g., *arachis* oil, olive oil, sesame oil or coconut oil), or in a mineral oil (e.g., liquid paraffin). Oily suspensions can contain one or more thickening agents, for example beeswax, hard paraffin, or cetyl alcohol. These compositions can be preserved by the addition of an anti-oxidant such as ascorbic acid.

The pharmaceutical compositions of the invention can also be in the form of oil-in-water emulsions. The oily phase can be a vegetable oil, for example olive oil or *arachis* oil, or a mineral oil, for example liquid paraffin or mixtures of these. Suitable emulsifying agents can be naturally-occurring gums, such as gum acacia or gum tragacanth; naturally-occurring phospholipids, such as soy lecithin; esters or partial esters derived from fatty acids and hexitol anhydrides, such as sorbitan monooleate; and condensation products of said partial esters with ethylene oxide, such as polyoxyethylene sorbitan monooleate.

Additionally, the present invention encompasses various administration modes by which the compounds can be delivered to increase bioavailability or blood brain barrier penetration, including but not limited to, intravenous, intranasal, intrathecal, subcutaneous, intracranial and oral. Time release technology can be used to increase bioavailability including formulations for sustained-release (SR), sustained-action (SA), extended-release (ER, XR, XL) timed-release (TR), controlled-release (CR), modified release (MR), continuous-release, osmotic release and slow release implants.

The use of hybrid molecules to promote active transport or nanoparticles can be used in certain embodiments to increase blood brain barrier transport. For example liposomes, proteins, engineered peptide compounds or antibodies that bind to the receptors that transport proteins across the blood brain barrier including LPR-1 receptor, transferrin receptor, EGF-like growth factor or glutathione transporter can be used to increase penetration into the brain. Physical techniques including osmotic opening, ultrasound, lasers, sphenopalantine ganglion stimulation, direct intracranial, intrathecal, or intraventricular delivery via a pump can be used.

Pharmaceutical compositions according to the invention can also include one or more additional active agents useful in the treatment of conditions associated with *P. gingivalis* infection. In certain embodiments, the invention provides a pharmaceutical composition comprising one or more Rgp inhibitors as described herein in combination with one or more additional active agents for treatment of Alzheimer's disease. Several therapeutics are in development and in clinical use for treatment of Alzheimer's disease. Therapeutic strategies include lowering circulating levels of β-amyloid and tau (as described in more detail below), stabilizing microtubules, removing atherosclerotic plaques, modulating autophagy, modulating neurotransmitter levels, and inhibiting GABA(A) α5 receptors. Such therapeutics can maintain and/or restore cognitive function in subjects with Alzheimer's disease; slow the decline of cognitive function; and promote neuroplasticity and recovery of the brain.

Active agents that can be combined with Rgp inhibitors in pharmaceutical compositions include, but are not limited to, antibiotics (i.e., bacteriocidal compounds and bacteriostatic compounds), cholinesterase inhibitors, alpha-7 nicotinic receptor modulators, serotonin modulators, NMDA modulators, Aβ-targeted therapies, ApoE-targeted therapies, microglia-targeted therapies, blood/brain barrier-targeted therapies, tau-targeted therapies, complement-targeted therapies, and anti-inflammatories.

Any suitable antibiotic can be combined with one or more Rgp inhibitors in the pharmaceutical compositions of the invention. In certain embodiments, the invention provides a pharmaceutical composition containing one more Rgp inhibitors and an antibiotic having a *P. gingivalis* MIC$_{50}$ of less than 25 µg/ml. For example, the *P. gingivalis* MIC$_{50}$ of the antibiotic can be less than 20 µg/ml, less than 15 µg/ml, less than 10 µg/ml, less than 8 g/ml, less than 6 µg/ml, or less than 5 µg/ml. In some embodiments, the *P. gingivalis* MIC$_{50}$ of the antibiotic is less than 1 µg/ml. In some embodiments, the *P. gingivalis* MIC$_{50}$ of the antibiotic is less than 0.2 µg/ml.

Examples of bacteriocidal and bacteriostatic compounds include, but are not limited to: quinolones (e.g., moxifloxacin, gemifloxacin, ciprofloxacin, oflaxacin, trovafloxacin, sitafloxacin, and the like), pβ-lactams (e.g., penicillins such as amoxicillin, amoxacilin-clavulanate, piperacillin-tazobactam, penicillin G, and the like; and cephalosporins such as ceftriaxone and the like), macrolides (e.g., erythromycin, azithromycin, clarithromycin, and the like), carbapenems (e.g., doripenem, imipenem, meropinem, ertapenem, and the like), thiazolides (e.g., tizoxanidine, nitazoxanidine, RM 4807, RM 4809, and the like), tetracyclines (e.g., tetracycline, minocycline, doxycycline, eravacycline, and the like), clindamycin, metronidazole, and satranidazole. Bacteriocidal and bacteriostatic compounds also include agents that inhibit or otherwise interfere with formation of biofilms by anaerobic, gram-negative bacteria; such agents include oxantel, morantel, thiabendazole, and the like. Compositions of the invention can contain one or more Rgp inhibitors with one or more (e.g., two, three, four, five, six, or more) bacteriocidal/bacteriostatic compounds. Compositions containing bacteriocidal/bacteriostatic compounds can further contain a chlorhexidine (e.g., chlorhexidine digluconate) alone or in combination with a zinc compound (e.g., zinc acetate), can also be used in combination with the administered antibiotics.

In some embodiments, a combination of a penicillin (e.g., amoxicillin) and metronidazole or a combination of penicillin (e.g., amoxicillin), metronidazole and a tetracycline is used. In some embodiments, the antibiotic is selected from minocycline, doxycycline, metronidazole, amoxicillin, clindamycin, augmentin, satranidazole, and combinations thereof.

Examples of suitable cholinesterase inhibitors include, but are not limited to, donepezil, donepezil/memantine, galantamine, rivastigmine, and tacrine, as well as pharmaceutically acceptable salts thereof. Examples of suitable serotonin modulators include, but are not limited to, idalopirdine, RVT-101, citalopram, escitalopram, fluoxetine, fluvoxamine, paroxetine, and sertraline, as well as pharmaceutically acceptable salts thereof. Examples of suitable alpha-7 nicotinic receptor modulators include, but are not limited to, alpha-7 agonists such as encenicline and APN1125. Suitable NMDA modulators include, but are not limited to, NMDA receptor antagonists such as memantine and derivatives thereof.

Pharmaceutical compositions of the invention can also contain active agents that are directed to biomolecular targets associated with neurological diseases. Such targets include beta amyloid peptides (also referred to as beta amyloid, abeta, or Aβ), apolipoprotein E (also referred to as ApoE), and microtubule-associated tau (also referred to as tau proteins, or simply as tau).

Aβ-targeted therapies include inhibitors of Aβ production (such as beta-secretase inhibitors, gamma-secretase inhibitors, alpha-secretase activators), inhibitors of Aβ aggregation, inhibitors of Aβ oligomerization, and up-regulators of Aβ clearance, among others (see, e.g., Jia, et al. *BioMed Research International,* 2014. Article ID 837157, doi: 10.1155/2014/837157). Examples of Aβ-targeted therapies include but are not limited to, antibodies, pioglitazone, begacestat, atorvastatin, simvastatin, etazolate, and tramiprosate, as well as pharmaceutically acceptable salts thereof.

Examples of ApoE-targeted therapies include, but are not limited to retinoid X receptor agonists (see, Cramer, et al., *Science* 2012. 335(6075): 1503-1506) and others described by Liu et al. (*Nat Rev Neurol.* 2013. 9(2): 106-118). Tau-targeted therapies include, but are not limited to, methylthioninium, leuco-methylthioninium, antibodies and those described by Lee, et al. (*Cold Spring Harb Perspect Med* 2011; 1:a006437).

Pharmaceutical compositions of the invention can also contain complement-targeted therapies. Such therapies target components of the complement system involved in the innate immune response. Complement targeted therapies include, but are not limited to, those described by Ricklin and Lambris (*Nat. Biotechnology* 2007. 25(11): 1265-1275).

Examples of suitable anti-inflammatories include, but are not limited to, NSAIDs such as apazone, diclofenac, ibuprofen, indomethacin, ketoprofen, nabumetone, naproxen, piroxicam, and sulindac, as well as pharmaceutically acceptable salts thereof.

VI. Methods for Treating Conditions Associated with P. *Gingivalis* Infection As described above, infection with *P. gingivalis* and gingipain activity have been linked to the development of periodontal disease, Alzheimer's and other brain disorders, cardiovascular disease, diabetes, cancer, liver disease, kidney disease, preterm birth, arthritis, pneumonia and other disorders. See: Bostanci, et al. FEMS Microbiol Lett, 2012. 333(1): 1-9; Ghizoni, et al. *J Appl Oral Sci,* 2012. 20(1): 104-12; Gatz, et al. *Alzheimers Dement,* 2006. 2(2): 110-7; Stein, et al. *J Am Dent Assoc,* 2007. 138(10): 1314-22; quiz 1381-2; Noble, et al. *J Neurol Neurosurg Psychiatry,* 2009. 80(11): 1206-11; Sparks Stein, et al. *Alzheimers Dement,* 2012. 8(3): 196-203; Velsko, et al. *PLoS ONE,* 2014. 9(5): e97811; Demmer, et al. *J Dent Res,* 2015. 94(9S): 201-S-11S; Atanasova and Yilmaz. *Molecular Oral Microbiology,* 2014. 29(2): 55-66; Yoneda, et al. *BMC Gastroenterol,* 2012. 12: 16.

Extracellular proteases produced by *P. gingivalis*, including Arginine Gingipain A (RgpA), Arginine Gingipain B (RgpB), and Lysine Gingipain (Kgp), can also degrade a broad range of proteins in connective tissue and plasma (e.g., collagen, immunoglobulins, and proteinase inhibitors, etc.). Gingipains can enter systemic circulation and/or synoviocytes and chondrocytes, and they can also cause disruption to the kallikrein-kinin cascade, blood coagulation, and host defense systems. Patients with gingipains in their joints and circulatory system may be subject to gingipain-induced death of synovial cells and/or chondrocytes, contributing to osteoarthritis.

It has now been discovered that RgpB and Kgp can infiltrate human and dog joints, contributing to the development of osteoarthritis. It is believed that *P. gingivalis* and gingipains can infiltrate joint tissues via a number of routes, giving rise to these new observations. Gingipains can be secreted, transported to outer membrane surfaces of *P. gingivalis*, or released in outer membrane vesicles by the bacterium. *P. gingivalis* has previously been identified in periodontal tissues, coronary arteries, aorta, and recently, the liver-release of *P. gingivalis* and/or gingipains from any of these niches into the systemic circulation could result in translocation of *P. gingivalis* and/or gingipains to the joints. See: Travis, et al. *Adv Exp Med Biol,* 2000. 477: 455-65; Byrne, et al. *Oral Microbiol Immunol,* 2009. 24(6): 469-77; Mahendra, et al. *J Maxillofac Oral Surg,* 2009. 8(2): 108-13; Stelzel. *Periodontol,* 2002. 73(8): 868-70; Ishikawa, et al. *Biochim Biophys Acta,* 2013. 1832(12): 2035-2043.

*P. gingivalis* and/or gingipains may also enter joints by degrading the endothelial cells protecting the blood/joint barrier, or by a traumatic event to the joint, such as a meniscus injury, which permanently or transiently reduces the integrity of the joint tissues. Such a disruption in traumatic joint injury for example, may contribute to the infiltration of *P. gingivalis* and/or gingipains in infected individuals and subsequent development of chronic osteoarthritis. People who are at a high risk of traumatic joint injury, including athletes in contact sports like football, could be preventatively treated with gingipain inhibitors to reduce the risk of trauma-related osteoarthritis.

P. gingivalis and gingipains may also reach the joint through other mechanisms including active transport, passive transport or macrophage delivery. Osteoarthritis resulting from any of these mechanisms can be limited to a single joint or present in multiple joints.

Similar to humans, P. gingivalis infection and periodontal disease is one of the most common infectious diseases affecting adult dogs and cats. Using adult beagle dogs, researchers demonstrated the existence of Rgp in plaque samples taken from beagle dogs given a specific soft diet to increase plaque formation on tooth surfaces. (See, e.g.: Davis and Head, *Front Pharmacol*, 2014. 5: 47; Reichart, et al., *Journal of Periodontal Research*, 1984. 19(1): 67-75; Kataoka, S., et al., *FASEB J*, 2014 28(8): 3564-78.) Dogs and cats with P. gingivalis infection and gingipains in their joints and circulatory system may experience periodontal disease and osteoarthritis due to gingipain-induced cell death, which could be treated or prevented according to the methods of the invention.

Aged dogs spontaneously develop many features of osteoarthritis, including a common inflammatory knee arthritis associated with degeneration of the anterior cruciate ligament (ACL). A study by Muir et al. of dogs with inflammatory knee arthritis and ACL degeneration detected DNA from a range of bacterial species in 37% of knee joints from affected dogs. Muir et al. hypothesized that bacteria may be an important causative factor in the pathogenesis of inflammatory arthritis in dogs. In the Muir et al. study, DNA from P. gingivalis was not detected in the dog joints. See, Muir, et al. *Microb Pathog*, 2007. 42(2-3): 47-55. However, similar to humans, P. gingivalis is a common oral pathogen affecting adult dogs, and could potentially translocate from the oral cavity to joint tissues as a result of bacteremia. Using adult beagle dogs, researchers have demonstrated the existence of Arg-gingipain, a secreted cysteine protease virulence factor of *Porphyromonas gingivalis*, in oral plaque samples taken from beagle dogs given a specific soft diet to increase plaque formation on tooth surfaces. Arginine-gingipain has been identified as the main collagenase factor of P. gingivalis, and could lead to collagen breakdown in infected joint tissues of dogs. Additionally, P. gingivalis has been demonstrated to infect chondrocytes in vitro causing chondrocyte apoptosis, indicating a pathway for cartilage loss in osteoarthritis of both dogs and humans. See: Rohner, et al. *Calcif Tissue Int*, 2010. 87(4): p. 333-40; Houle, et al. *FEMS Microbiol Lett*, 2003. 221(2): p. 181-5; Kataoka, et al. *FASEB J*, 2014. 28: 3564-3578; Pischon, et al. *Ann Rheum Dis*, 2009. 68(12): p. 1902-7.

Rgp inhibitors can therefore be used to treat diseases and conditions, such as brain disorders, caused by or otherwise affected by P. gingivalis. Accordingly, another aspect of the invention provides a method of treating a disease or condition associated with P. gingivalis infection. The method includes administering to a subject an effective amount of a compound according to Formula II:

(II)

or a pharmaceutically acceptable salt thereof, thereby treating the disease or condition, wherein:

Z' is selected from aryloxymethyl-carbonyl, benzothiazol-2-yl-carbonyl, thiazol-2-yl-carbonyl, oxazol-2-yl-carbonyl, benzooxazol-2-yl-carbonyl, pyridin-2-yl-carbonyl, pyrimidin-4-yl-carbonyl, pyrimidin-2-yl-carbonyl, isoxazol-5-yl-carbonyl, isoxazol-3-yl-carbonyl, 1,2,4-oxadiazol-3-yl-carbonyl, 1,2,4-oxadiazol-5-yl-carbonyl, cyano, ethynyl, fluoromethyl-carbonyl, acyloxymethyl-carbonyl, alkylsulfonyl-vinyl, and arylsulfonyl-vinyl;

wherein Z' is optionally substituted with one or more substituents selected from halogen, $C_{1-4}$ alkyl, $C_{1-4}$ alkoxy, $C_{1-4}$ haloalkyl, $C_{1-4}$ haloalkoxy, and $-N_3$;

each $R^{1a}$ is independently selected from hydrogen, $C_{1-4}$ alkyl, and an amine protecting group;

$R^{2a}$ is selected from hydrogen and $C_{1-4}$ alkyl;

$R^{3a}$ is selected from $C_{3-8}$ cycloalkyl, $C_{3-8}$ alkyl, $C_{6-10}$ aryl, 5-to-12 membered heteroaryl, and 5-to-12 membered heterocyclyl, wherein $R^{3a}$ is optionally substituted with one or more $R^{4a}$ substituents independently selected from halo, $-CN$, $-NO_2$, $-N_3$, $-OH$, $R^a$, $-OR^b$, $-N(R^d)_2$, $-(CH_2)_kC(O)R^c$, $-NR^d(CH_2)_uC(O)R^c$, $-O(CH_2)_uC(O)R^c$, $-(CH_2)_kCON(R^d)_2$, $-(CH_2)_kNR^dC(O)R^c$, $-NR^d(CH_2)_uCON(R^d)_2$, $-NR^d(CH_2)_uNR^dC(O)R^c$, $-O(CH_2)_uCON(R^d)_2$, and $-O(CH_2)_uNR^dC(O)R^c$;

each $R^a$, $R^b$, and $R^c$ is independently selected from $C_{1-4}$ alkyl and $C_{1-4}$ haloalkyl, each $R^d$ is independently selected from hydrogen and $C_{1-8}$ alkyl, each subscript k is independently selected from 0, 1, 2, 3, 4, 5, and 6, and each subscript u is independently selected from 1, 2, 3, 4, 5, and 6.

In some embodiments, the method includes administering one or more compounds from Table 1 to a subject.

TABLE 1

Compounds for use in the treatment of conditions associated with *P. Gingivalis* infection.

| Compound No. | Compound Structure |
|---|---|
| 1 | 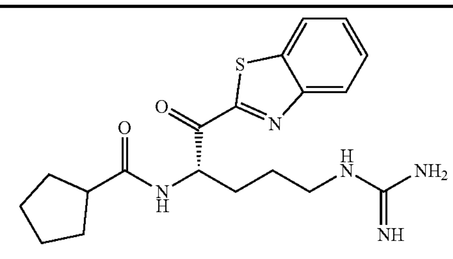 |
| 2 | 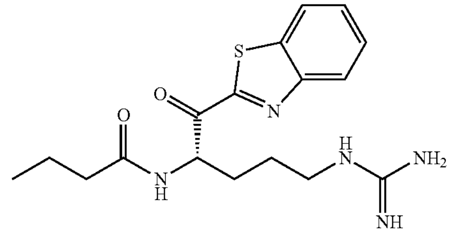 [SMILES: CCCC(=O)N[C@@H](CCCNC(=N)N)C(=O)c1nc2ccccc2s1] |

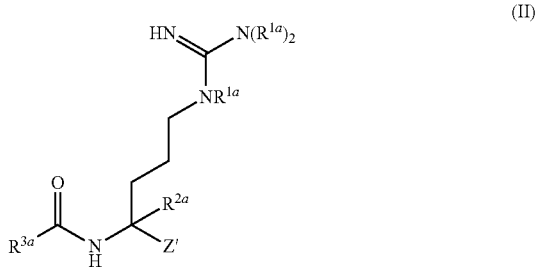

TABLE 1-continued

Compounds for use in the treatment of conditions associated with *P. Gingivalis* infection.

| Compound No. | Compound Structure |
|---|---|
| 3 | 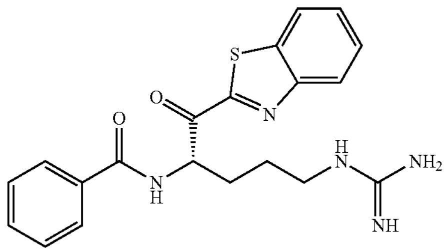 [SMILES: N=C(N)NCCC[C@H](NC(=O)c1ccccc1)C(=O)c1nc2ccccc2s1] |
| 4 | 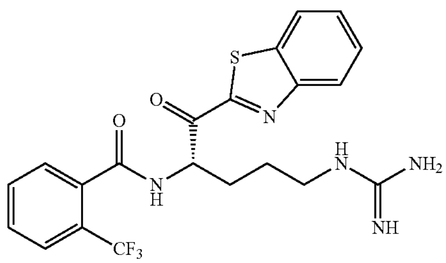 [SMILES: N=C(N)NCCC[C@H](NC(=O)c1ccccc1C(F)(F)F)C(=O)c1nc2ccccc2s1] |
| 5 | 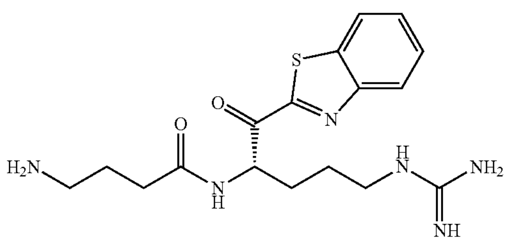 [SMILES: N=C(N)NCCC[C@H](NC(=O)CCCN)C(=O)c1nc2ccccc2s1] |
| 6 | 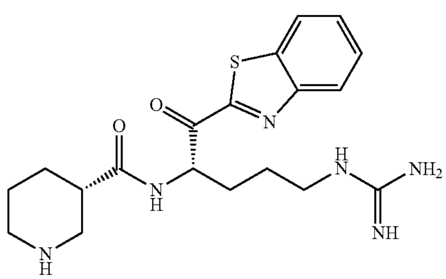 [SMILES: N=C(N)NCCC[C@H](NC(=O)[C@H]1CCCNC1)C(=O)c1nc2ccccc2s1] |
| 7 | 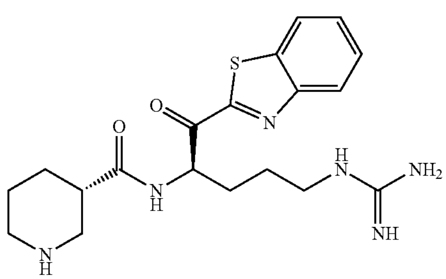 [SMILES: N=C(N)NCCC[C@@H](NC(=O)[C@H]1CCCNC1)C(=O)c1nc2ccccc2s1] |
| 8 | 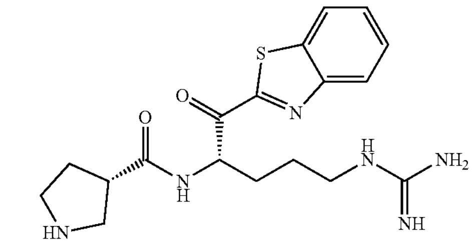 [SMILES: N=C(N)NCCC[C@H](NC(=O)[C@H]1CCNC1)C(=O)c1nc2ccccc2s1] |
| 9/10 | 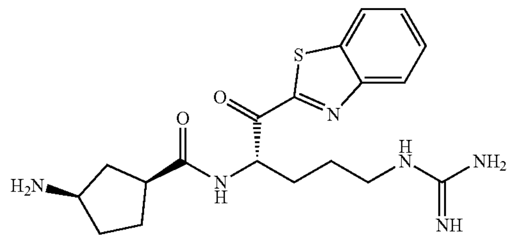 [SMILES: N=C(N)NCCC[C@H](NC(=O)[C@H]1CC[C@@H](N)C1)C(=O)c1nc2ccccc2s1] |
| 11/12 | 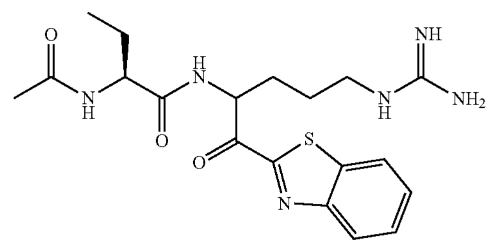 [SMILES: CC[C@H](NC(C)=O)C(=O)NC(CCCNC(=N)N)C(=O)c1nc2ccccc2s1] |
| 13 | 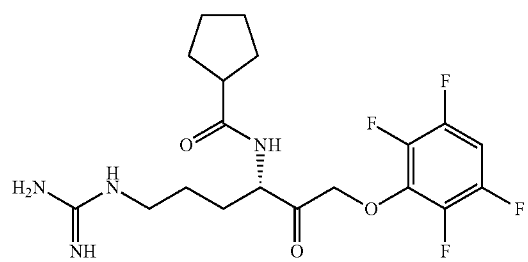 [SMILES: N=C(N)NCCC[C@H](NC(=O)C1CCCC1)C(=O)COc1c(F)c(F)cc(F)c1F] |
| 14 | 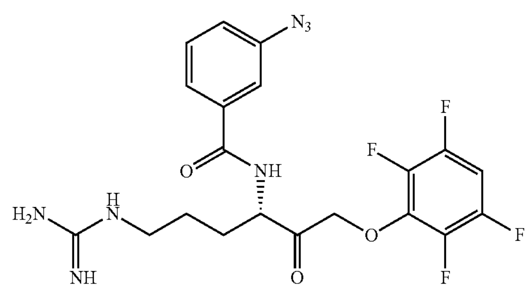 [SMILES: [N-]=[N+]=Nc1cccc(C(=O)N[C@@H](CCCNC(=N)N)C(=O)COc2c(F)c(F)cc(F)c2F)c1] |

In some embodiments, the invention provides a method of treating a disease or condition associated with *P. gingivalis* infection as described above, wherein the subject is a human or a canine.

In some embodiments, the invention provides a method of treating a disease or condition associated with *P. gingivalis* infection as described above, wherein the compound of Formula II is a compound having a structure according to Formula IIa:

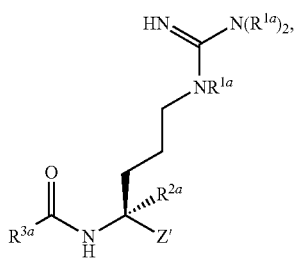

(IIa)

or a pharmaceutically acceptable salt thereof.

In some embodiments, the method includes administering a compound of Formula II wherein Z' is selected from benzothiazol-2-yl-carbonyl, halogen-substituted aryloxymethyl-carbonyl, pyridin-2-yl-carbonyl, and thiazol-2-yl-carbonyl. In some such embodiments, Z' is selected from aryloxymethyl-carbonyl and benzothiazol-2-yl-carbonyl. In some such embodiments, Z' is (2,3,5,6-tetraflurophenoxymethyl)carbonyl.

In some embodiments, the compound of Formula II administered in the method is a compound having a structure according to Formula IIb

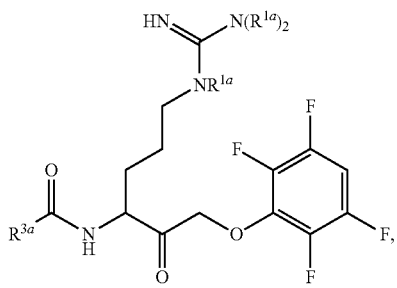

(IIb)

or a pharmaceutically acceptable salt thereof.

In some embodiments, the method includes administering a compound of formula IIb, or a pharmaceutically acceptable salt thereof, wherein $R^3$ is selected from $C_{3-8}$ cycloalkyl, $C_{6-10}$ aryl, 5-to-12 membered heteroaryl, and 5-to-12 membered heterocyclyl, each of which is optionally substituted with one or more $R^4$ substituents. In some such embodiments, $R^3$ is selected from cyclopentyl, phenyl, and azidophenyl.

In some embodiments, the method includes administering a compound selected from:

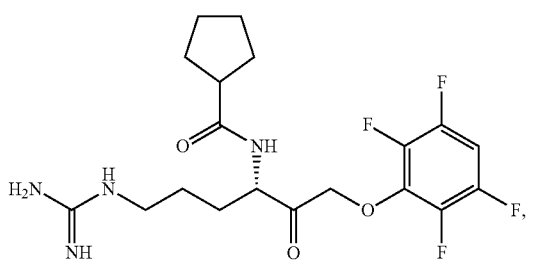

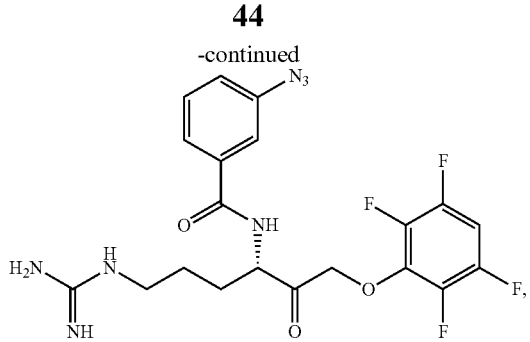

and pharmaceutically acceptable salts thereof.

In some embodiments, the method includes administering

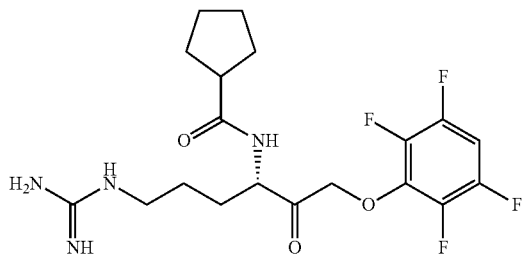 [SMILES: N=C(N)NCCC[C@H](NC(=O)C1CCCC1)C(=O)COc1c(F)c(F)cc(F)c1F]

or a pharmaceutically acceptable salt thereof.

In some embodiments, the compound of Formula II administered in the method is a compound having a structure according to Formula IIc:

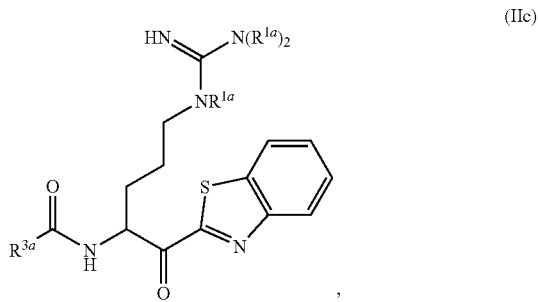

(IIc)

or a pharmaceutically acceptable salt thereof, wherein $R^{3a}$ is selected from phenyl, trifluromethylphenyl, piperidin-3-yl, pyrrolidin-3-yl, 3-aminocyclopentyl, n-propyl, 3-aminopropyl, and (1-acetamido)propyl.

In some embodiments, the method includes administering a compound selected from:

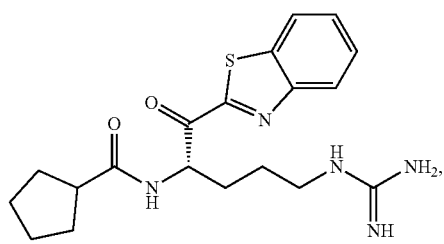

-continued

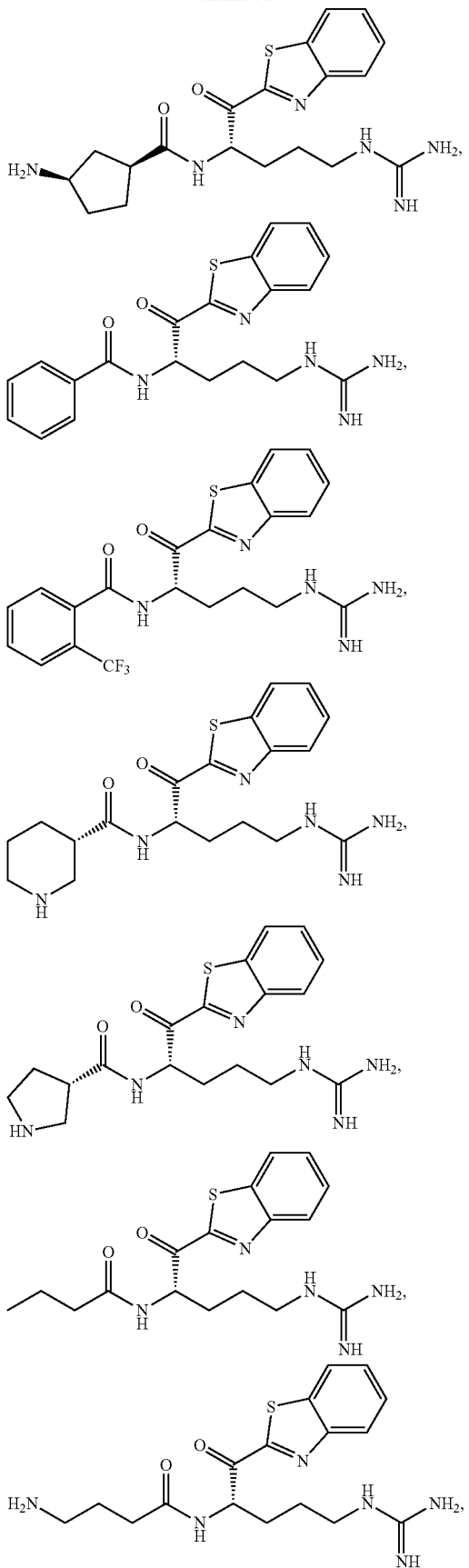

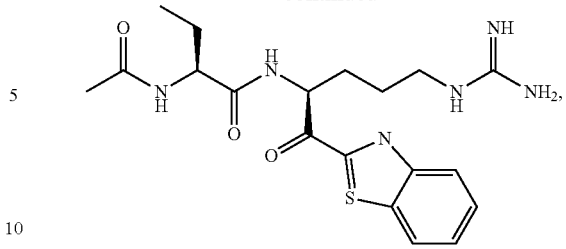

and pharmaceutically acceptable salts thereof.

In some embodiments, the method of the invention includes administering a compound according to Formula II as described above, provided that when Z is phenyoxymethylcarbonyl or substituted phenoxymethylcarbonyl, $R^3$ and the carbonyl to which it is bonded form a moiety other than prolinyl, substituted prolinyl, argininyl, substituted argininyl, phenylalaninyl, substituted phenylalaninyl, tert-butylaminocarbonyl, or tert-butyloxy-carbonyl.

In some embodiments, the method of the invention includes administering a compound according to Formula II as described above, provided that when Z is benzothiazol-2-yl-carbonyl, $R^3$ is selected from the group consisting of phenyl, trifluromethylphenyl, piperidin-3-yl, pyrrolidin-3-yl, 3-aminocyclopentyl, n-propyl, 3-aminopropyl, and (1-acetamido)propyl.

In certain embodiments, compounds of the invention inhibit active Rgp in the brain of a mammal, e.g., a human or an animal (e.g., a dog), and are cytoprotective or neuroprotective. By "neuroprotective," it is meant that the compounds prevent aberrant changes to neurons or death of neurons. Compounds of the invention are therefore useful, e.g., in treatment of a brain disorder (e.g., a neurodegenerative disease (e.g., Alzheimer's disease, Down's syndrome, epilepsy, autism, Parkinson's disease, essential tremor, fronto-temporal dementia, progressive supranuclear palsy, amyotrophic lateral sclerosis, Huntington's disease, multiple sclerosis, mild cognitive impairment, age associated memory impairment, chronic traumatic encephalopathy, stroke, cerebrovascular disease, Lewy Body disease, multiple system atrophy, schizophrenia and depression, etc.), diabetes, cardiovascular disease, arthritis, rheumatoid arthritis, osteoarthritis, infectious arthritis, psoriatic arthritis, retinal disorders (e.g., age related macular degeneration) and glaucoma.

In some embodiments, the disease or condition is selected from a brain disorder, periodontal disease, diabetes, a cardiovascular disease, arthritis, rheumatoid arthritis, osteoarthritis, preterm birth, pneumonia, cancer, a kidney disease, a liver disease, a retinal disorder, and glaucoma.

In some embodiments, the disease or condition is a brain disorder.

In some embodiments, the brain disorder is selected from Alzheimer's disease, Down's syndrome, epilepsy, autism, Parkinson's disease, essential tremor, fronto-temporal dementia, progressive supranuclear palsy, amyotrophic lateral sclerosis, Huntington's disease, multiple sclerosis, mild cognitive impairment, age associated memory impairment, chronic traumatic encephalopathy, stroke, cerebrovascular disease, Lewy Body disease, multiple system atrophy, schizophrenia, and depression.

In some embodiments, the brain disorder is Alzheimer's disease.

In some embodiments, the method further includes administering to the subject one or more active agents selected from a cholinesterase inhibitor, a serotonin modulator, an NMDA modulator, an Aβ targeted therapy, an ApoE targeted therapy, a microglia targeted therapy, a blood brain barrier targeted therapy, a tau targeted therapy, a complement targeted therapy, and an anti-inflammatory.

In some embodiments, the disease or condition is periodontal disease. In some embodiments, the disease or condition is a liver disease. In some embodiments, the liver disease is non-alcoholic steatohepatitis. In some embodiments, the disease or condition is a retinal disorder. In some embodiments, the retinal disorder is age-related macular degeneration.

In some embodiments, the disease or condition is cancer. In some embodiments, the cancer is breast cancer, oral cancer, pancreatic cancer, or glioblastoma multiforme.

Rgp inhibitors as described herein can be administered at any suitable dose in the methods of the invention. In general, an Rgp inhibitor is administered at a dose ranging from about 0.1 milligrams to about 1000 milligrams per kilogram of a subject's body weight (i.e., about 0.1-1000 mg/kg). The dose of Rgp inhibitor can be, for example, about 0.1-1000 mg/kg, or about 1-500 mg/kg, or about 25-250 mg/kg, or about 50-100 mg/kg. The dose of Rgp inhibitor can be about 1, 2, 3, 4, 5, 10, 15, 20, 25, 30, 35, 40, 45, 50, 55, 60, 65, 70, 75, 85, 90, 95, 100, 150, 200, 250, 300, 350, 400, 450, 500, 550, 600, 650, 700, 750, 800, 850, 900, 950 or 1000 mg/kg. The dosages can be varied depending upon the requirements of the patient, the severity of the disorder being treated, and the particular formulation being administered. The dose administered to a patient should be sufficient to result in a beneficial therapeutic response in the patient. The size of the dose will also be determined by the existence, nature, and extent of any adverse side-effects that accompany the administration of the drug in a particular patient. Determination of the proper dosage for a particular situation is within the skill of the typical practitioner. The total dosage can be divided and administered in portions over a period of time suitable to treat to the seizure disorder.

Rgp inhibitors can be administered for periods of time which will vary depending upon the nature of the particular disorder, its severity, and the overall condition of the subject to whom the Rgp inhibitor is administered. Administration can be conducted, for example, hourly, every 2 hours, three hours, four hours, six hours, eight hours, or twice daily including every 12 hours, or any intervening interval thereof. Administration can be conducted once daily, or once every 36 hours or 48 hours, or once every month or several months. Following treatment, a subject can be monitored for changes in his or her condition and for alleviation of the symptoms of the disorder. The dosage of the Rgp inhibitor can either be increased in the event the subject does not respond significantly to a particular dosage level, or the dose can be decreased if an alleviation of the symptoms of the disorder is observed, or if the disorder has been remedied, or if unacceptable side effects are seen with a particular dosage.

A therapeutically effective amount of an Rgp inhibitor can be administered to the subject in a treatment regimen comprising intervals of at least 1 hour, or 6 hours, or 12 hours, or 24 hours, or 36 hours, or 48 hours between dosages. Administration can be conducted at intervals of at least 72, 96, 120, 144, 168, 192, 216, or 240 hours (i.e., 3, 4, 5, 6, 7, 8, 9, or 10 days). In certain embodiments, administration of one or more Rgp inhibitors is conducted in a chronic fashion over periods ranging from several months to several years. Accordingly, some embodiments of the invention provide a method of treating a disease or condition associated with *P. gingivalis* infection as described above, wherein the compound is administered to the subject for at least one year. In some embodiments, the compound is administered to the subject for at least 10 years. In some embodiments, the compound is administered to the subject for at least 60 years.

Administration of Rgp inhibitors according to the methods of the invention typically results in the reduction of circulating levels of active Rgp in a subject and/or the reduction of active Rgp in the brain. In certain embodiments, administration of an Rgp inhibitor according to the methods of the invention results in at least a 20% reduction of circulating levels of active Rgp and/or at least a 20% reduction of active Rgp in the brain. For example, the circulating levels of Rgp and/or the levels of Rgp in the brain are preferably reduced by from about 25% to about 95%, or from about 35% to about 95%, or from about 40% to about 85%, or from about 40% to about 80% as compared to the corresponding levels of Rgp 24 hours prior to the first administration of the Rgp inhibitor.

Rgp inhibitors can be administered alone or in combination with one or more additional therapeutically active agents, as described above. The one or more additional therapeutically effective agents include, e.g.: (i) a pharmaceutically acceptable agent which inhibits RgpA, RgpB, and/or Kgp production, translocation of RgpA, RgpB, and/or Kgp into systemic circulation or brain, and/or pathological (e.g., neurotoxic effects) of RgpA, RgpB, and/or Kgp in a mammal; (ii) an antibacterial agent which is bacteriostatic or bacteriocidal with respect to *P. gingivalis*; (iii) one or more antibodies which bind to RgpA, RgpB and/or Kgp (e.g., 18E6, which binds to the first half of the immunoglobulin domain of RgpB; Kgp-specific monoclonal antibody, 7B9, which recognizes an epitope within the Kgp catalytic domain; the RgpA antibody 61Bg 1.3, humanized versions of any of the foregoing, etc.); (iv) epitopes of antibodies which bind to RgpA, RgpB and/or Kgp or other proteins expressed by *P. gingivalis*; and (v) combinations of any of the foregoing.

The additional therapeutically active agents also include Aβ peptides level reducers, pathogenic level tau reducers, microtubule stabilizers, agents capable or removing atherosclerotic plaques, agents that lower circulating levels of β-amyloid and tau, modulators of autophagy, neurotransmitter level regulators, GABA(A) α5 receptors inhibitors, and additional agents that help maintain and/or restore cognitive function and functional deficits of Alzheimer's disease, and/or slow down decline in cognitive functions and functional deficits in Alzheimer's disease.

Pharmaceutical compositions of the invention can contain one or more Rgp inhibitors as described herein in combination with ritonavir (RTV), which can increase bioavailability and increase blood brain barrier penetration. For example, ritonavir is commonly combined with oral peptidic HIV protease inhibitors to increase plasma levels by inhibiting the P450 3A4 enzyme and thus decreasing first-pass metabolism (see, Walmsley, et al., *N Engl J Med*, 2002. 346(26): 2039-46). In addition, RTV binds to P-glycoprotein, a transmembrane efflux pump that is found in many tissues, including the blood brain barrier, allowing co-administered compounds better access to the brain (see, Marzolini, et al., *Mol Pharm*, 2013. 10(6): 2340-9). Therefore, a combination of RTV and Rgp inhibitors can be used to increase plasma concentrations and brain levels of the gingipain inhibitors. As described in U.S. patent application Ser. No. 14/875,416, oral administration of RTV 15 minutes prior to the Kgp inhibitor, Kyt-36 increases the half-life therefore it is expected that RTV will also increase the half-life of Rgp inhibitors.

In some embodiments, compounds of the invention can be administered with natural gingipain inhibitors including melabaricone C, isolated from nutmeg or polyphenolic compounds derived from plants, such as cranberry, green tea, apple, and hops can be administered in conjunction for treatment or prevention of brain disorders. Naturally and unnaturally occurring antimicrobial peptides including: K-casein peptide (109-137) 34, histatin 5, and CL(14-25), CL(K$_{25}$A) and CL(R24A, K$_{25}$A), can also be administered in conjunction with the Rgp inhibitors of the invention. (see, e.g., Taniguchi et al., *Biopolymers*, 2014. 102(5): 379-89).

Rgp inhibitors as described herein can be administered with antibodies targeting gingipains or other *P. gingivalis* proteins. Antibodies may rely on damage to the blood brain barrier for access to the brain or peripheral interference with gingipains and *P. gingivalis* propagation. Antibodies can also help to stimulate the efficacy of the immune system in clearing the bacteria. New or existing antibodies to RgpA, RgpB, or Kgp can be utilized including 18E6 and 7B9. An RgpA antibody 61BG 1.3 has previously demonstrated efficacy topically in prevention of recolonization by *P. gingivalis* after periodontal treatment. See, Booth et al., *Infect Immun,* 1996. 64(2): 422-7. Antibodies would preferably be humanized for use in humans. Methods known to those in the field for delivery of biologics to improve half-life and brain penetration can be used including, but not limited to, intravenous delivery, subcutaneous delivery, intranasal delivery, intrathecal delivery, intra-articular delivery, vector transport, and direct brain delivery.

The methods of the invention also encompass administration of Rgp inhibitors as described herein with one or more of the following additional therapeutically active agents or pharmaceutically acceptable salts thereof: an arginine derivative; histatin 5; baculovirus p35; a single point mutant of cowpox viral cytokine-response modifier (CrmA (Asp>Lys)); phenylalanyl-ureido-citrullinyl-valyl-cycloarginal (FA-70C1); (acycloxy)methyl ketone (Cbz-Phe-Lys-CH$_2$OCO-2,4,6-Me3Ph); peptidyl chloro-methyl ketones (e.g., chloromethyl ketone derivatives of arginine, chloromethyl ketone derivatives of lysine, and the like); fluoro-methyl ketones; bromo-methyl ketones; ketopeptides; 1-(3-phenylpropionyl)piperidine-3(R,S)-carboxylic acid [4-amino-1 (S)-(benzothiazole-2-carbonyl)butyl]amide (A71561); azapeptide fumaramide; aza-peptide Michael acceptors; benzamidine compounds; acyclomethylketone; activated factor X inhibitors (e.g., DX-9065a); cranberry nondialyzable fraction; cranberry polyphenol fraction; pancreatic trypsin inhibitor; Cbz-Phe-Lys-CH$_2$O—CO-2,4,6-Me3-Ph; E-64; chlorhexidine; zinc (e.g., zinc acetate); or a combination of two, three or more of any of foregoing. In some of these embodiments, Zn can enhance potency and selectivity of the compounds (e.g., chlorhexidine, benzamidine, etc.) used in the methods of the invention.

An Rgp inhibitor of the invention can be administered in the same composition as an additional therapeutically active agent. Alternatively, the additional therapeutically active agent can be administered separately before, concurrently with, or after administration of the Rgp inhibitor.

Similar to humans, *P. gingivalis* infection and periodontal disease is one of the most common infectious diseases affecting adult dogs and cats. Studies have demonstrated the existence of Rgp in plaque samples taken from adult beagle dogs given a specific soft diet to increase plaque formation on tooth surfaces. (See, e.g.: Davis and Head, Front *Pharmacol,* 2014. 5: 47; Reichart, et al., *Journal of Periodontal Research,* 1984. 19(1): 67-75; Kataoka, S., et al., *FASEB J,* 2014 28(8): 3564-78.) Dogs and cats with *P. gingivalis* infection and gingipains in their brain and circulatory system may experience periodontal disease, mild cognitive impairment, age associated memory impairments, diabetes, damage or generalized accelerated aging due to gingipain induced cell death, which can be treated or prevented with the compounds of the invention.

VII. Methods of Detecting *P. gingivalis* and Diagnosing Conditions Associated with *P. gingivalis* Infection The present invention also provides for a diagnostic test for gingipains or *P. gingivalis* in the brain or patient samples in order to diagnose or predict brain disorders, or to determine who would be the best candidates for treatment with compounds described herein. Changes in serum profiles associated with *P. gingivalis* infection have been previously observed. According to the invention, the risk of development of brain disorders can be diagnosed or otherwise assessed by conducting an ELISA on saliva, cerebral spinal fluid or blood, for example, to detect one or both gingipains. Saliva, blood and CSF levels of gingipain or other *P. gingivalis* markers would be expected to be higher in at risk patients and patients who are good candidates for treatment. Development of an ELISA is a fairly simple process known to those skilled in the art utilizing one antibody against the target to capture the target and a second labeled antibody against a different epitope on the target to obtain a quantitative readout. Commercially available or newly generated antibodies could be used for this purpose. Immobilized or labeled compounds described herein (for example with biotin or HRP) could be utilized to substitute for one or both antibodies. Click chemistry compounds such as those depicted in FIG. 4 could be utilized for this purpose. The diagnostic could include detection of one or more gingipains. Biotinylation of the detection antibody can be used to increase sensitivity.

Alternatively, instead of detecting the presence or absence of the gingipains, an assay for their activity in saliva, CSF or blood could be used. This would provide the benefit of providing a readout on the most biologically relevant factor (e.g., activity) in the presence or absence of treatment, for example. Methods for developing enzyme assays are known to those skilled in the art. A salivary test known as the BANA Test is commercially available for dental applications to test for proteases from *P. gingivalis* and other oral bacteria. The BANA test is a small plastic card to which is attached two separate reagent matrices, seen as strips on the card. The lower white reagent matrix is impregnated with N-benzoyl-DL-arginine-B-naphthylamide (BANA). Subgingival plaque samples are applied to the lower matrix, and then distilled water is applied to the upper matrix. Then the lower matrix is folded back to make contact with the upper matrix. The upper buff reagent matrix contains a chromogenic diazo reagent which reacts with one of the hydrolytic products of the enzyme reaction forming a blue color. The reaction occurs when the plastic strip is inserted into an incubator set at 35 degrees C. for 5 minutes. The BANA substrate detects at least three different oral bacteria however and is not specific to *P. gingivalis*. The BANA test could be used to identify people at risk for brain disorders or eligible for treatment. Alternatively, the BANA substrate can be substituted in similar formats or in a liquid assay with an RgpA, RgpB and/or Kgp specific substrate.

Reagents that bind to active gingipains, including but not limited to those described in this application, can be used to precipitate only active gingipains followed by detection with a monoclonal for example. Alternatively, an antibody or other high affinity binding agent could be used to precipitate the gingipain from the CSF followed by a protease assay with a labeled substrate, which allows for increased fluorescence or colorimetric readout as the labeled substrate is digested.

Figure 4:
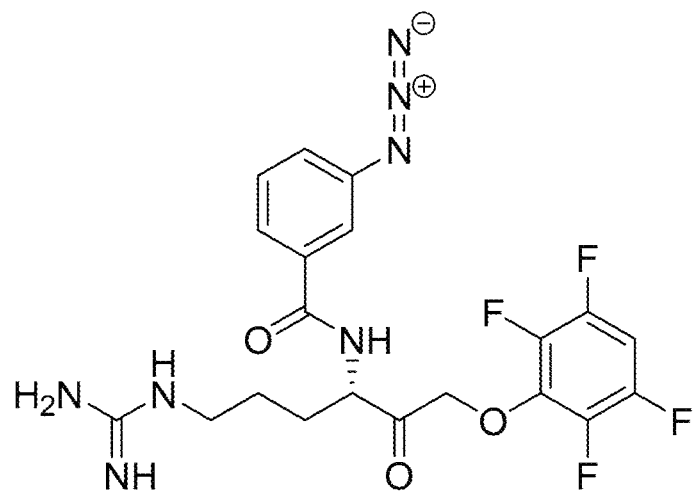
FIG. 4 shows an example of a "click chemistry" compound that can be used to create radiolabeled PET/SPECT imaging agents or capture agents for in vitro assays or diagnostics.
Figure 4:
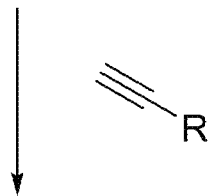
Figure 4:
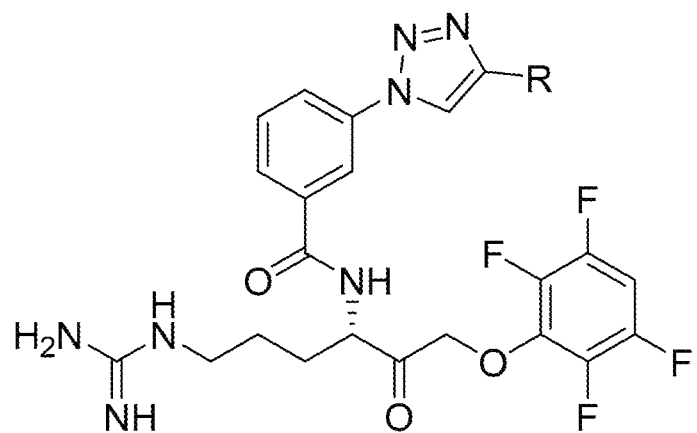

The present invention also provides for a diagnostic based on imaging *P. gingivalis* or its gingipains in the human brain. Any agent that binds to gingipains, including but not limited to compounds of the present invention and other compounds described elsewhere, can be labeled with F18 or other radiographic markers and visualized using PET or SPECT scanning. A positive signal would indicate treatment with compounds described herein. In a preferred and non-limiting embodiment, compound 45 as described herein is modified via "click chemistry" to install a radiolabel that can be imaged with PET or SPECT (FIG. 4).

Accordingly, another aspect of the invention provides a method of treating a disease or condition associated with *P. gingivalis* infection including: obtaining a biological sample from the patient; assaying the sample to determine the presence or absence of gingipains from *P. gingivalis* in the biological sample; and administering a therapeutic agent to the patient when the a gingipain is present in the biological sample. In some embodiments, the biological sample is a cerebrospinal fluid sample. In some embodiments, the assaying includes conducting an ELISA for gingipains on patient cerebral spinal fluid. In some embodiments, the active agent is a compound according to Formula II or Formula I as described herein.

VIII. Examples

Example 1. Animals Treated with Gingipains Exhibit Neurodegeneration

Adult male mice (CD-1, 25 g approximately) n=6 per group were anaesthetized and injected unilaterally intrahippocampally using standard stereotaxic techniques. Gingipains RgpB and Kgp, purified from *P. gingivalis* were diluted prior to injection to 10 μg/ml. Seven days post-surgery the animals were anaesthetized, perfused and humanely killed and brains removed and sectioned for histological analysis. Fluoro-Jade staining was then be performed on sections of hippocampus to assess for neurodegeneration (Schmued L C and Hopkins K J, 2000). Fluoro-Jade staining identifies cell bodies, dendrites, axons and axons terminals of degenerating neurons but does not stain healthy neurons, myelin, or vascular elements.

Brain sections were examined with an epifluorescence microscope (Nikon Microphot FXA) using a filter system suitable for visualizing fluorescein or fluorescein isothiocyanate (FITC). Images were acquired with a Leica DC Camera and an Image Analysis software (Leica IM50). Fluoro-Jade C-positive degenerating neurons appeared bright yellow-green against a dark background and were clearly identified in the animal groups treated with Gingipains. No Fluoro-Jade C-positive cells were observed in vehicle-treated group (FIG. 1).

Example 2. Animals Infected with *P. gingivalis* Exhibit Neurodegeneration

Figure 2:
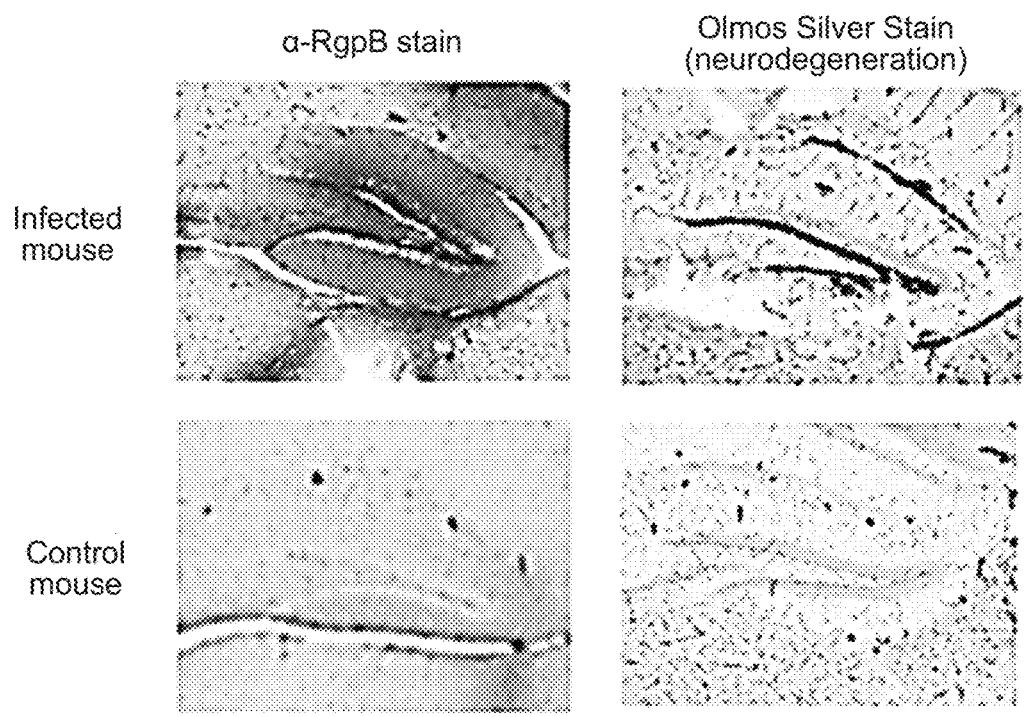
FIG. 2 shows that RgpB brain infiltration overlaps with neurodegeneration of the subgranular zone in the hippocampus of BalbC mice infected with *P. gingivalis* orally for 6 weeks.

Female Balb/c mice were obtained from Harlan Laboratories (USA) and allowed to acclimate. 8 week old mice were challenged orally with $10^9$ CFU W83 *P. gingivalis* in 2% Na-CMC, 2 times per week for 6 weeks. Control mice received mock challenge with 2% Na-CMC only. 6 weeks after initial infection, mice were sacrificed, perfused and brains dissected. Brains were embedded and sectioned. 18E6 immunohistochemistry for RgpB showed brain infiltration in 3/6 mice. De Olmos silver stain for neurodegeneration showed staining in 2 of the 3 mice with infiltration (FIG. 2).

Example 3. Animals Infected with *P. gingivalis* Exhibit Cognitive Dysfunction Female Balb/cJ mice were obtained from Taconic and allowed to acclimate. 8 week old mice were challenged orally with $10^9$ CFU W83 *P. gingivalis* every $3^{rd}$ day for 4 administrations.

Figure 3A:
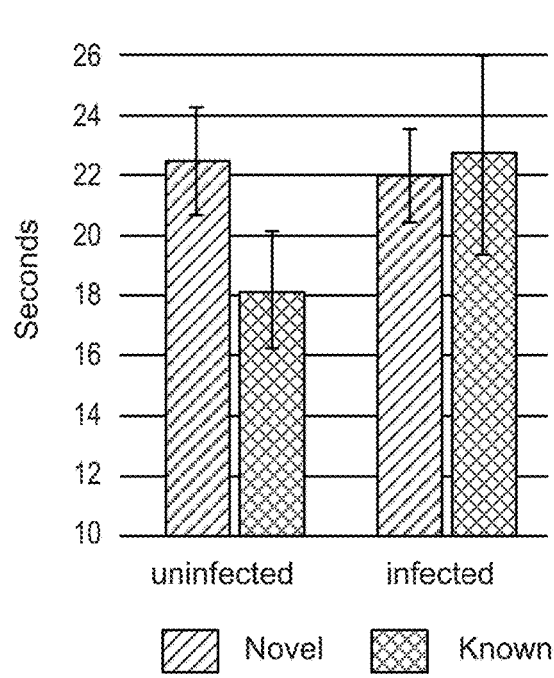
FIG. 3A shows that wild-type mice infected with *P. gingivalis* show cognitive impairment on the Novel Object Recognition task at the 6 week time point. Infected mice spend equal amounts of time exploring a novel and familiar object, while normal mice spend increased time on the novel object.
Figure 3B:
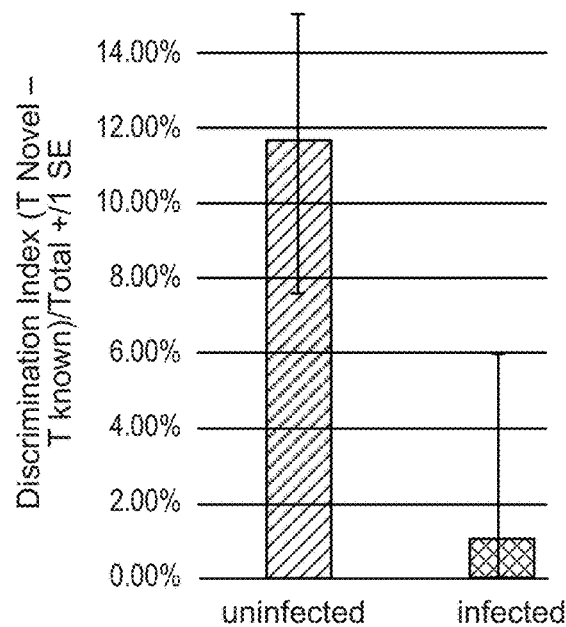
FIG. 3B shows the discrimination index $(T_{novel}-T_{familar})/T_{total}$ for the uninfected mice and the infected mice.

Novel object recognition test for cognitive function was initiated 6 weeks after the initial infection. Mice were familiarized with the test cage for 2 min the day prior to object familiarization. On the day of familiarization, mice were presented with two wooden blue rectangles for 5 minutes. 24 hours later mice were presented with one blue rectangle (right side) and one pink heart (left side, both objects made of wood) for the duration of 3 min. The time during which the mouse directed its nose within 2 cm of an object was recorded. Mock infected mice on average spent more time exploring the novel object compared to infected mice who on average spent equal time on both objects indicating cognitive dysfunction (FIG. 3).

Example 4. Preparation of 1-[(4S)-4-amino-5-(1,3-benzothiazol-2-yl)-5-oxo-pentyl]-3-[(2,2,4,6,7-pentamethyl-3H-benzofuran-5-yl)sulfonyl]guanidine (Core R)

Scheme 7

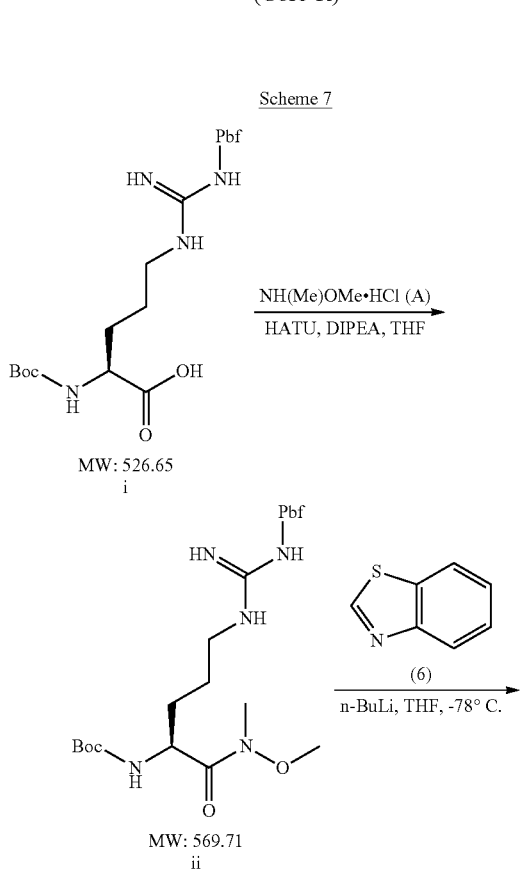

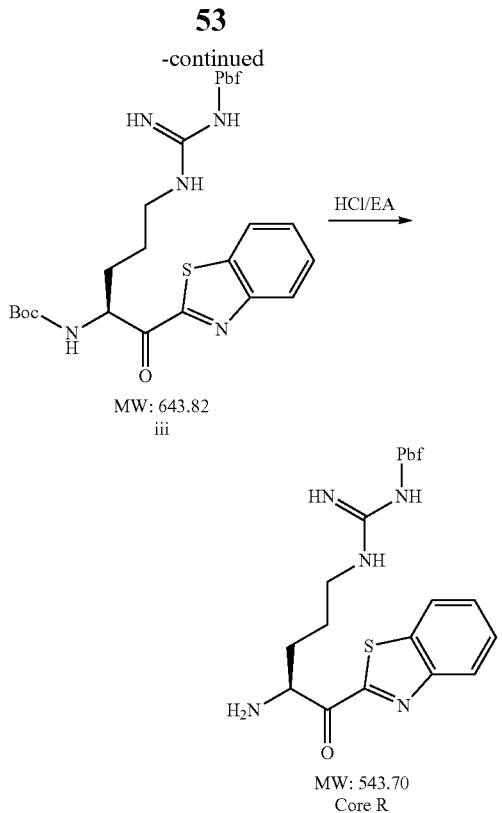

Tert-butyl-N-[(1S)-1-[methoxy(methyl)carbamoyl]-4-[[N-[(2,2,4,6,7-pentamethyl-3H-benzofuran-5-yl)sulfonyl]carbamimidoyl]amino]butyl]carbamate (ii)

To a mixture of (2S)-2-(tert-butoxycarbonylamino)-5-[[N-[(2,2,4,6,7-pentamethyl-3H-benzofuran-5-yl)sulfonyl]carbamimidoyl]amino]pentanoic acid (25.00 g, 47.47 mmol, 1.00 eq), N-methoxymethanamine (9.26 g, 94.94 mmol, 2.00 eq), DIPEA (18.41 g, 142.41 mmol, 3.00 eq) in THF (120 mL) was added HATU (21.66 g, 56.96 mmol, 1.20 eq). The mixture was stirred at 30° C. for 16 hr. TLC (PE:EA=1:1) indicated the starting material consumed completely. Then water (200 mL) was added and extracted with EA (300 mL×3), dried over $Na_2SO_4$, concentrated to give the crude product, which was purified by flash chromatography to give tert-butyl-N-[(1S)-1-[methoxy(methyl)carbamoyl]-4-[[N-[(2,2,4,6,7-pentamethyl-3H-benzofuran-5-yl)sulfonyl]carbamimidoyl]amino]butyl]carbamate (25.40 g, 44.58 mmol, 93.9% yield) as a white solid.

Tert-butyl-N-[(1S)-1-(1,3-benzothiazole-2-carbonyl)-4-[[N-[(2,2,4,6,7-pentamethyl-3H-benzofuran-5-yl)sulfonyl]carbamimidoyl]amino]butyl]carbamate (iii)

To a mixture of 1,3-benzothiazole (5.93 g, 43.90 mmol, 5.00 eq) in THF (50 mL) was added n-BuLi (2.5 M in THF, 7 mL) dropwise at −65° C. under $N_2$. The mixture was stirred at −65° C. under $N_2$ for 1 hr. Then a solution of tert-butyl-N-[(1S)-1-[methoxy(methyl)carbamoyl]-4-[[N-[(2,2,4,6,7-pentamethyl-3H-benzofuran-5-yl)sulfonyl]carbamimidoyl]amino]butyl]carbamate (5.00 g, 8.78 mmol, 1.00 eq) in THF (50 mL) was added dropwise at −65° C. under $N_2$ and the reaction mixture was stirred at −65° C. under $N_2$ for 3 hr. TLC (PE:EA=1:1) indicated the starting material was consumed completely. Sat. $NH_4Cl$ (aq, 80 mL) was added and the mixture was extracted with EA (100 mL×2), dried over $Na_2SO_4$, concentrated to give the crude product, which was purified by flash chromatography to give tert-butyl-N-[(1S)-1-(1,3-benzothiazole-2-carbonyl)-4-[[N-[(2,2,4,6,7-pentamethyl-3H-benzofuran-5-yl)sulfonyl]carbamimidoyl]amino]butyl]carbamate (16.20 g, 25.16 mmol, 71.6% yield; 65.9% ee) as a white solid.

1-[(4S)-4-amino-5-(1,3-benzothiazol-2-yl)-5-oxo-pentyl]-3-[(2,2,4,6,7-pentamethyl-3H-benzofuran-5-yl)sulfonyl]guanidine (Core R)

To a mixture of tert-butyl-N-[(1S)-1-(1,3-benzothiazole-2-carbonyl)-4-[[N-[(2,2,4,6,7-pentamethyl-3H-benzofuran-5-yl)sulfonyl]carbamimidoyl]amino]butyl]carbamate (16.20 g, 25.16 mmol, 1.00 eq) in EA (100 mL) was added HCl/EA (4 M, 10 mL). The mixture was stirred at 30° C. for 1 hr. TLC (PE:EA=1:1) indicated the starting material was consumed completely. The mixture was filtered to give 1-[(4S)-4-amino-5-(1,3-benzothiazol-2-yl)-5-oxo-pentyl]-3-[(2,2,4,6,7-pentamethyl-3H-benzofuran-5-yl)sulfonyl]guanidine hydrochloride (11.30 g, 19.48 mmol, 77.4% yield) as a yellow solid.

Example 5. Preparation of N-[(1S)-1-(1,3-benzothiazole-2-carbonyl)-4-guanidino-butyl]cyclopentanecarboxamide (1)

Scheme 8

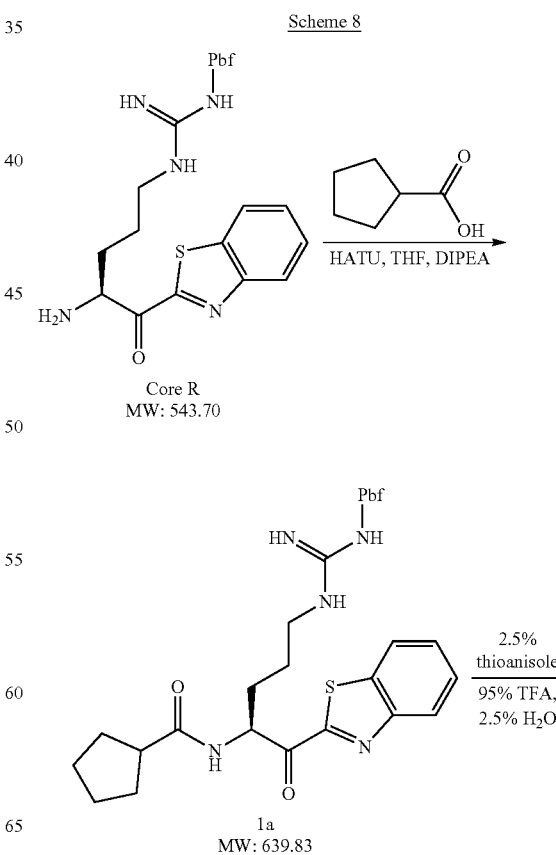

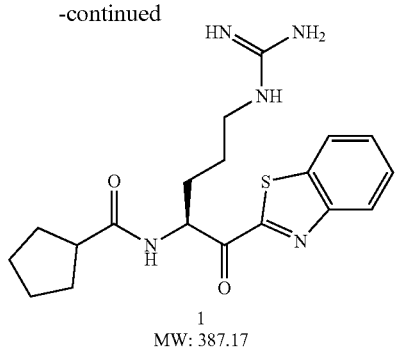

1
MW: 387.17

N-[(1S)-1-(1,3-benzothiazole-2-carbonyl)-4-[[N-[(2,2,4,6,7-pentamethyl-3H-benzofuran-5-yl)sulfonyl]carbamimidoyl]amino]butyl]cyclopentanecarboxamide (1a)

To a mixture of 1-[(4S)-4-amino-5-(1,3-benzothiazol-2-yl)-5-oxo-pentyl]-3-[(2,2,4,6,7-pentamethyl-3H-benzofuran-5-yl)sulfonyl]guanidine hydrochloride (500 mg, 861.83 μmol, 1.00 eq), cyclopentanecarboxylic acid (118 mg, 1.03 mmol, 1.20 eq), DIPEA (334.15 mg, 2.59 mmol, 3.00 eq) in THF (5 mL) was added HATU (393 mg, 1.03 mmol, 1.20 eq) at 0° C., and the reaction was stirred at 0° C. for 1 hr. TLC indicated the reaction completed, then EA (30 mL) was added and washed with water (20 mL×3), dried over $Na_2SO_4$, concentrated to give the crude, which was purified by flash chromatography to give N-[(1S)-1-(1,3-benzothiazole-2-carbonyl)-4-[[N-[(2,2,4,6,7-pentamethyl-3H-benzofuran-5-yl)sulfonyl]carbamimidoyl]amino]butyl]cyclopentanecarboxamide (270 mg, 421.99 μmol, 48.9% yield) as a yellow solid.

N-[(1S)-1-(1,3-benzothiazole-2-carbonyl)-4-guanidino-butyl]cyclopentane-carboxamide (1)

To a mixture of TFA (1.9 mL), $H_2O$ (0.05 mL) and thioanisole (0.05 mL) was added N-[(1S)-1-(1,3-benzothiazole-2-carbonyl)-4-[[N-[(2,2,4,6,7-pentamethyl-3H-benzofuran-5-yl)sulfonyl]carbamimidoyl]amino]butyl]cyclopentane-carboxamide (270 mg, 421.99 μmol, 1.00 eq) at 0° C. Then the reaction was stirred at 30° C. for 16 hr. LC-MS indicated the reaction completed. Water (30 mL) was added, then the mixture was lyophilized to give the crude product, which was purified by prep-HPLC ($CH_3CN/H_2O$/TFA) to give N-[(1S)-1-(1,3-benzothiazole-2-carbonyl)-4-guanidino-butyl]cyclopentanecarboxamide trifluoroacetate (22 mg, 43.87 μmol, 10.4% yield) as a white solid. MS m/z=388.1 (MH+).

Example 6. Preparation of N-[(1S)-1-(1,3-benzothiazole-2-carbonyl)-4-guanidino-butyl]butanamide (2)

Scheme 9

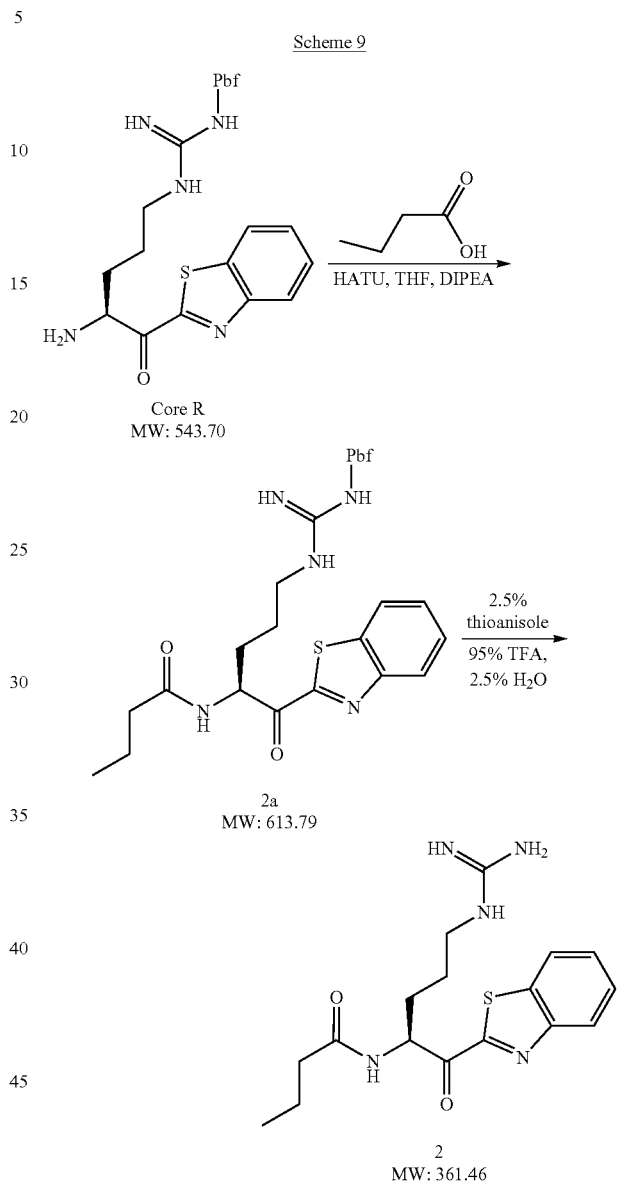

N-[(1S)-1-(1,3-benzothiazole-2-carbonyl)-4-[[N-[(2,2,4,6,7-pentamethyl-3H-benzofuran-5-yl)sulfonyl]carbamimidoyl]amino]butyl]butanamide (2a)

To a mixture of 1-[(4S)-4-amino-5-(1,3-benzothiazol-2-yl)-5-oxo-pentyl]-3-[(2,2,4,6,7-pentamethyl-3H-benzofuran-5-yl)sulfonyl]guanidine hydrochloride (400 mg, 689.46 μmol, 1.00 eq), butyric acid (73 mg, 827.36 μmol, 1.20 eq), DIPEA (267 mg, 2.07 mmol, 3.00 eq) in THF (5 mL) was added HATU (315 mg, 827.36 μmol, 1.20 eq) at 0° C. Then the mixture was stirred at 30° C. for 16 h. TLC (PE:EA=1:1) indicated the starting material was consumed completely. EA (30 mL) was added and the mixture was washed with water (10 mL×3), dried over $Na_2SO_4$, concentrated to give the crude product, which was purified by flash chromatography to give N-[(1S)-1-(1,3-benzothiazole-2- carbonyl)-4-[[N-[(2,2,4,6,7-pentamethyl-3H-benzofuran-5-yl)sulfonyl]carbamimidoyl]amino]butyl]butanamide (300 mg, 488.77 μmol, 70.9% yield) as a yellow solid. ¹H NMR (CD₃OD, 400 MHz) d 8.22 (d, J=7.6, 1H), 8.15 (d, J=7.6, 1H), 7.70-7.62 (m, 2H), 5.76-5.71 (m, 1H), 3.29-3.24 (m, 2H), 2.28 (t, J=7.3, 2H), 2.22-2.15 (m, 1H), 1.85-1.75 (m, 3H), 1.67 (hex, J=7.3, 2H), 0.95 (t, J=7.3, 3H).

N-[(1S)-1-(1,3-benzothiazole-2-carbonyl)-4-guanidino-butyl]butanamide (2)

To a mixture of TFA (1.9 mL), H₂O (0.05 mL), thioanisole (0.05 mL) was added N-[(1S)-1-(1,3-benzothiazole-2-carbonyl)-4-[[N-[(2,2,4,6,7-pentamethyl-3H-benzofuran-5-yl)sulfonyl]carbamimidoyl]amino]butyl]butanamide (250 mg, 407.31 μmol, 1.00 eq) at 0° C. Then the reaction was stirred at 30° C. for 16 h. LC-MS indicated the starting material was consumed completely. Water (50 mL) was added and the mixture was lyophilized to give the crude product, which was purified by prep-HPLC (CH₃CN/H₂O/TFA) to give N-[(1S)-1-(1,3-benzothiazole-2-carbonyl)-4-guanidino-butyl]butanamide trifluoroacetate (17.49 mg, 36.78 μmol, 9.03% yield) as a light yellow solid. MS m/z=362.1 (MH⁺).

Example 7. Preparation of N-[(1S)-1-(1,3-benzothiazole-2-carbonyl)-4-guanidino-butyl]cyclopentanecarboxamide (3)

Scheme 10

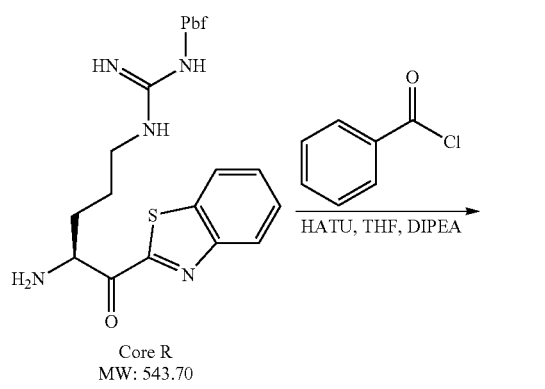

Core R
MW: 543.70

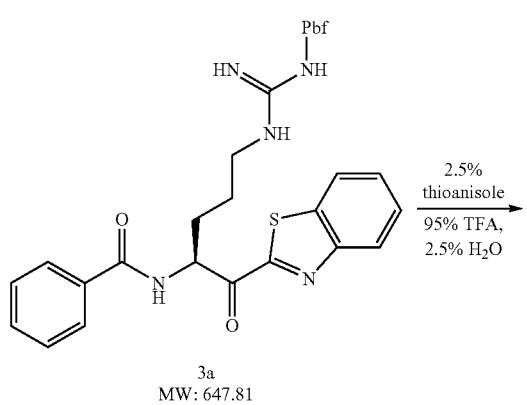

3a
MW: 647.81

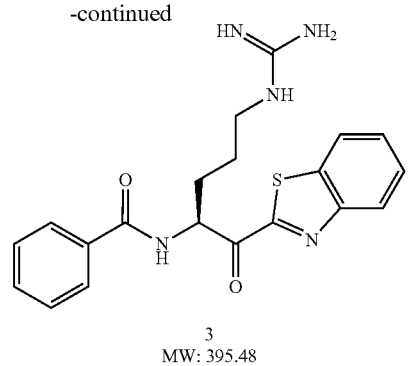

3
MW: 395.48

N-[(1S)-1-(1,3-benzothiazole-2-carbonyl)-4-[[N-[(2,2,4,6,7-pentamethyl-3H-benzofuran-5-yl)sulfonyl]carbamimidoyl]amino]butyl]benzamide (3a)

To a mixture of 1-[(4S)-4-amino-5-(1,3-benzothiazol-2-yl)-5-oxo-pentyl]-3-[(2,2,4,6,7-pentamethyl-3H-benzofuran-5-yl)sulfonyl]guanidine hydrochloride (500 mg, 861.83 μmol, 1.00 eq), TEA (262 mg, 2.59 mmol, 3.00 eq) in DCM (5 mL) was added a solution of benzoyl chloride (121 mg, 861.83 μmol, 1.00 eq) in DCM (1 mL) drop-wise at 0° C. under N₂. Then the mixture was stirred at 0° C. for 0.5 h. TLC indicated the reaction completed. DCM (20 mL) was added and washed with water (15 mL×3), dried over Na₂SO₄, concentrated to give the crude, which was purified by flash chromatography to give N-[(1S)-1-(1,3-benzothiazole-2-carbonyl)-4-[[N-[(2,2,4,6,7-pentamethyl-3H-benzofuran-5-yl)sulfonyl]carbamimidoyl]amino]butyl]benzamide (300 mg, 463.10 μmol, 53.7% yield) as a yellow solid. ¹H NMR (CD₃OD, 400 MHz) d 8.25 (d, J=7.6, 1H), 8.26 (d, J=7.6, 1H), 7.91 (d, J=6.8, 2H), 7.66-7.46 (m, 5H), 5.92 (dd, J=9.6, J=4.0, 1H), 3.37-3.33 (m, 2H), 2.37-2.27 (m, 1H), 2.06-1.83 (m, 3H).

N-[(1S)-1-(1,3-benzothiazole-2-carbonyl)-4-guanidino-butyl]cyclopentane carboxamide (3)

To a mixture of TFA (1.9 mL), H₂O (0.05 mL), thioanisole (0.05 mL) was added N-[(1S)-1-(1,3-benzothiazole-2-carbonyl)-4-[[N-[(2,2,4,6,7-pentamethyl-3H-benzofuran-5-yl)sulfonyl]carbamimidoyl]amino]butyl]benzamide (300 mg, 463.10 μmol, 1.00 eq) at 0° C. Then the reaction was stirred at 30° C. for 16 hr. LC-MS indicated the starting material was consumed completely. Water (30 mL) was added and the mixture was lyophilized to give the crude, which was purified by prep-HPLC (CH₃CN/H₂O/TFA) to give N-[(1S)-1-(1,3-benzothiazole-2-carbonyl)-4-guanidino-butyl]benzamide trifluoroacetate (36.40 mg, 71.44 μmol, 15.4% yield) as a light yellow solid. MS m/z=396.1 (MH⁺).

Example 8. Preparation of N-[(1S)-1-(1,3-benzothiazole-2-carbonyl)-4-guanidino-butyl]-2-(trifluoromethyl)benzamide (4)

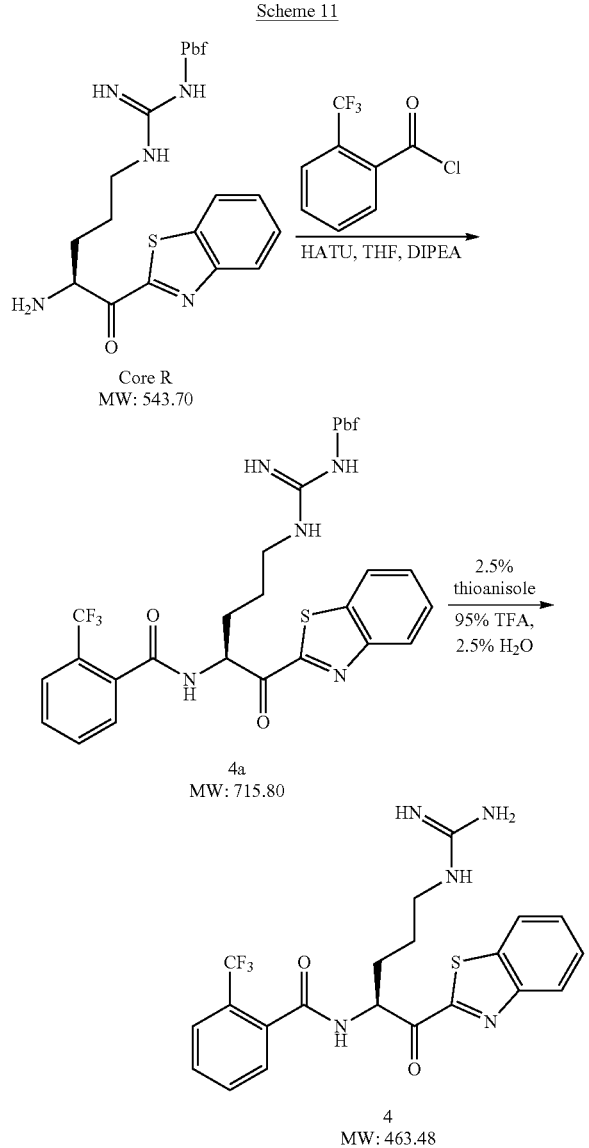

N-[(1S)-1-(1,3-benzothiazole-2-carbonyl)-4-[[N-[(2,2,4,6,7-pentamethyl-3H-benzofuran-5-yl)sulfonyl]carbamimidoyl]amino]butyl]-2-(trifluoromethyl)benzamide (4a)

To a mixture of 1-[(4S)-4-amino-5-(1,3-benzothiazol-2-yl)-5-oxo-pentyl]-3-[(2,2,4,6,7-pentamethyl-3H-benzofuran-5-yl)sulfonyl]guanidine hydrochloride (400 mg, 689.46 μmol, 1.00 eq), 2-(trifluoromethyl)benzoic acid (157 mg, 827.36 μmol, 1.20 eq), DIPEA (267 mg, 2.07 mmol, 3.00 eq) in THF (5 mL) was added HATU (316 mg, 827.36 μmol, 1.20 eq) at 0° C. Then the reaction was stirred at 30° C. for 16 h. TLC (PE:EA=1:1) indicated the reaction completed. EA (20 mL) was added and washed with water (10 mL×3), dried over Na$_2$SO$_4$, concentrated to give the crude product, which was purified by flash chromatography to give N-[(1S)-1-(1,3-benzothiazole-2-carbonyl)-4-[[N-[(2,2,4,6,7-pentamethyl-3H-benzofuran-5-yl)sulfonyl]carbamimidoyl]amino]butyl]-2-(trifluoromethyl)benzamide (300 mg, 419.11 μmol, 60.8% yield) as a yellow solid.

N-[(1S)-1-(1,3-benzothiazole-2-carbonyl)-4-guanidino-butyl]-2-(trifluoro-methyl)benzamide (4)

To a mixture of TFA (1.9 mL), H$_2$O (0.05 mL), thioanisole (0.05 mL) was added N-[(1S)-1-(1,3-benzothiazole-2-carbonyl)-4-[[N-[(2,2,4,6,7-pentamethyl-3H-benzofuran-5-yl)sulfonyl]carbamimidoyl]amino]butyl]-2-(trifluoromethyl)benzamide (300 mg, 419.11 μmol, 1.00 eq) at 0° C. Then the reaction was stirred at 30° C. for 16 hr. LC-MS indicated the starting material was consumed completely. Water (50 mL) was added and the mixture was lyophilized to give the crude product, which was purified by prep-HPLC (CH$_3$CN/H$_2$O/TFA) to give N-[(1S)-1-(1,3-benzothiazole-2-carbonyl)-4-guanidino-butyl]-2-(trifluoromethyl)benzamide trifluoroacetate (34.61 mg, 59.93 μmol, 14.3% yield) as a light yellow solid. MS m/z=464.1 (MH$^+$).

Example 9. Preparation of 4-amino-N-[(1S)-1-(1,3-benzothiazole-2-carbonyl)-4-guanidino-butyl]butanamide (5)

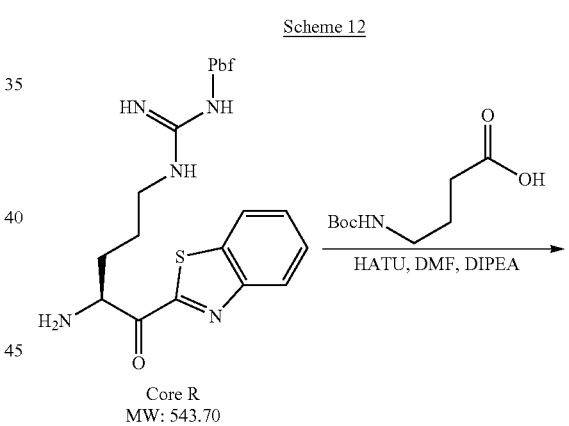

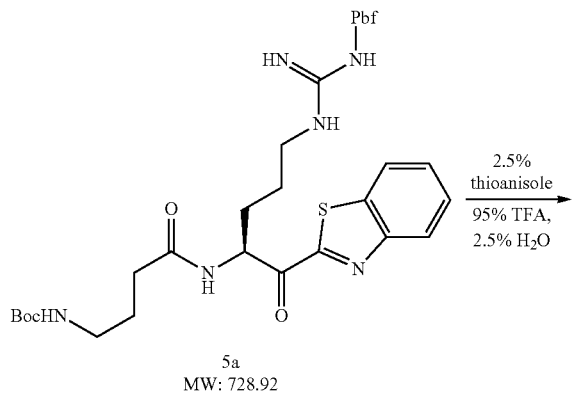

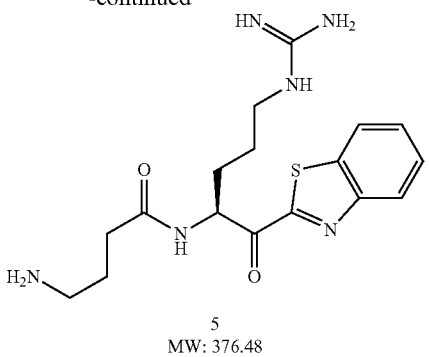

5
MW: 376.48

Tert-butyl-N-[4-[[(1S)-1-(1,3-benzothiazole-2-carbonyl)-4-[[N-[(2,2,4,6,7-pentamethyl-3H-benzofuran-5-yl)sulfonyl]carbamimidoyl]amino]butyl]amino]-4-oxo-butyl]carbamate (5a).

A mixture of 1-[(4S)-4-amino-5-(1,3-benzothiazol-2-yl)-5-oxo-pentyl]-3-[(2,2,4,6,7-pentamethyl-3H-benzofuran-5-yl)sulfonyl]guanidine hydrochloride (400 mg, 689.46 µmol, 1.00 eq), 4-(tert-butoxycarbonylamino)butanoic acid (154 mg, 758.41 µmol, 1.10 eq), DIPEA (267 mg, 2.07 mmol, 3.00 eq) in DMF (5 mL) was added HATU (315 mg, 827.36 µmol, 1.20 eq), then the reaction was stirred at 30° C. for 16 hr. TLC (PE: EA=1:1) indicated the reaction completed. EA (50 mL) was added and the mixture was washed with water (20 mL×2), dried over Na$_2$SO$_4$, concentrated to give a crude product, which was purified by column chromatography on silica gel (PE:EA=3:1 to PE:EA=1:1) to give tert-butyl-N-[4-[[(1S)-1-(1,3-benzothiazole-2-carbonyl)-4-[[N-[(2,2,4,6,7-pentamethyl-3H-benzofuran-5-yl)sulfonyl]carbamimidoyl]amino]butyl]amino]-4-oxo-butyl]carbamate (200 mg, 274.38 µmol, 39.8% yield) as a red solid.

4-amino-N-[(1S)-1-(1,3-benzothiazole-2-carbonyl)-4-guanidino-butyl]butanamide (5)

To a mixture of TFA (1.9 mL), H$_2$O (0.05 mL), thioanisole (0.05 mL) was added tert-butyl-N-[4-[[(1S)-1-(1,3-benzothiazole-2-carbonyl)-4-[[N-[(2,2,4,6,7-pentamethyl-3H-benzofuran-5-yl)sulfonyl]carbamimidoyl]amino]butyl]amino]-4-oxo-butyl]carbamate (200 mg, 274.38 µmol, 1.00 eq) at 0° C. Then the reaction was stirred at 30° C. for 16 hr. LC-MS indicated the starting material was consumed completely. Water (50 mL) was added and the mixture was lyophilized to give the crude product, which was purified by prep-HPLC (CH$_3$CN/H$_2$O/TFA) to give 4-amino-N-[(1S)-(1,3-benzothiazole-2-carbonyl)-4-guanidino-butyl]butanamide trifluoroacetate (20.55 mg, 41.90 µmol, 15.3% yield) as a white solid. MS m/z=377.1 (MH$^+$).

Example 10. Preparation of (3S)—N-[(1R/S)-1-(1,3-benzothiazole-2-carbonyl)-4-guanidino-butl]piperidine-3-carboxamide (6/7)

Scheme 13

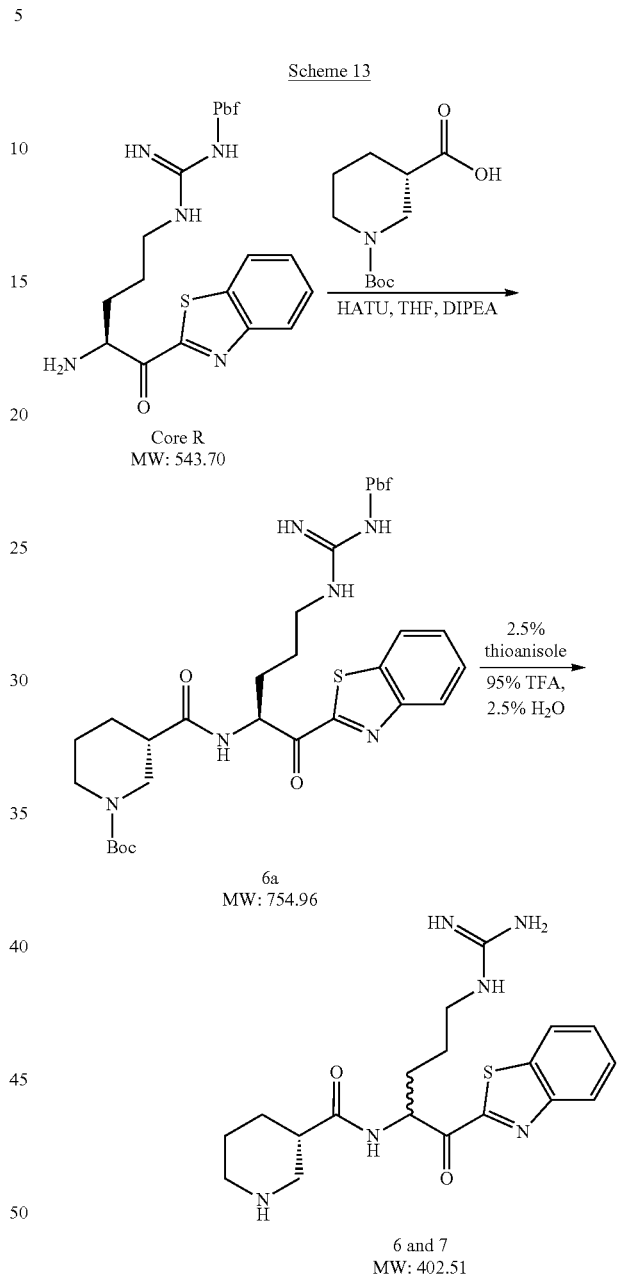

Tert-butyl-(3S)-3-[[(1S)-1-(1,3-benzothiazole-2-carbonyl)-4-[[N-[(2,2,4,6,7-pentamethyl-3H-benzofuran-5-yl)sulfonyl]carbamimidoyl]amino]butyl]carbamoyl]piperidine-1-carboxylate (6a).

To a mixture of (3S)-1-tert-butoxycarbonylpiperidine-3-carboxylic acid (190 mg, 827.35 µmol, 1.20 eq), DIPEA (267 mg, 2.07 mmol, 3.00 eq) in THF (10 mL) was added DIPEA (267 mg, 2.07 mmol, 3.00 eq) at 0° C. and the mixture was stirred at 0° C. for 0.5 hr. Then 1-[(4S)-4-amino-5-(1,3-benzothiazol-2-yl)-5-oxo-pentyl]-3-[(2,2,4,6,7-pentamethyl-3H-benzofuran-5-yl)sulfonyl]guanidine hydrochloride (400 mg, 689.46 µmol, 1.00 eq) was added and the reaction mixture was stirred at 30° C. for 16 h.

LC-MS indicated the starting material was consumed completely. EA (50 mL) was added and the mixture was washed with water (20 mL×2), dried over Na$_2$SO$_4$, concentrated to give tert-butyl-(3S)-3-[[(1S)-1-(1,3-benzothiazole-2-carbonyl)-4-[[N-[(2,2,4,6,7-pentamethyl-3H-benzofuran-5-yl)sulfonyl]carbamimidoyl]amino]butyl]carbamoyl]piperidine-1-carboxylate (300 mg, 397.37 μmol, 57.6% yield) as a yellow solid.

(3S)—N-[(1R/S)-1-(1,3-benzothiazole-2-carbonyl)-4-guanidino-butyl]piperidine-3-carboxamide (6/7)

To a mixture of TFA (1.9 mL), H$_2$O (0.05 mL), thioanisole (0.05 mL) was added tert-butyl-(3S)-3-[[(1S)-1-(1,3-benzothiazole-2-carbonyl)-4-[[N-[(2,2,4,6,7-pentamethyl-3H-benzofuran-5-yl)sulfonyl]carbamimidoyl]amino]butyl]carbamoyl]piperidine-1-carboxylate (300 mg, 397.37 μmol, 1.00 eq) at 0° C. Then the mixture was stirred at 30° C. for 16 hr. LC-MS indicated the starting material was consumed completely. Water (30 mL) was added and the mixture was lyophilized to give the crude product, which was purified by prep-HPLC (CH$_3$CN/H$_2$O/TFA) to give (3S)—N-[(1S)-1-(1,3-benzothiazole-2-carbonyl)-4-guanidino-butyl]piperidine-3-carboxamide trifluoroacetate (28.55 mg, 95.2% purity, Compound 6) and (3S)—N-[(1R)-1-(1,3-benzothiazole-2-carbonyl)-4-guanidino-butyl]piperidine-3-carboxamide trifluoroacetate (13.33 mg, 75.7% purity, Compound 7) as light yellow solids. MS m/z=403.1 (MH$^+$) for Compound 6 and Compound 7.

Example 11. Preparation of (3S)—N-[1-(1,3-benzothiazole-2-carbonyl)-4-guanidino-butyl]pyrrolidine-3-carboxamide (8)

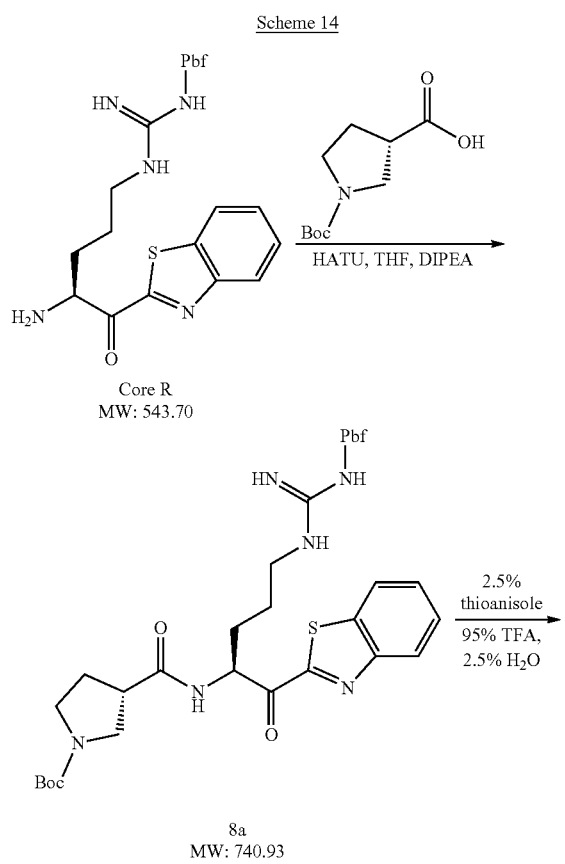

Scheme 14

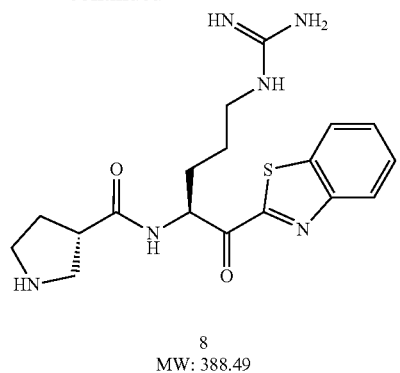

8
MW: 388.49

Tert-butyl-(3S)-3-[[(1S)-1-(1,3-benzothiazole-2-carbonyl)-4-[[N-[(2,2,4,6,7-pentamethyl-3H-benzofuran-5-yl)sulfonyl]carbamimidoyl]amino]butyl]carbamoyl]pyrrolidine-1-carboxylate (8a)

To a mixture of (3S)-1-tert-butoxycarbonylpyrrolidine-3-carboxylic acid (266 mg, 1.24 mmol, 1.20 eq), DIPEA (400 mg, 3.09 mmol, 3.00 eq) in THF (10 mL) was added HATU (470 mg, 1.24 mmol, 1.20 eq) at 0° C. and the mixture was stirred at 0° C. for 0.5 hr. Then 1-[(4S)-4-amino-5-(1,3-benzothiazol-2-yl)-5-oxo-pentyl]-3-[(2,2,4,6,7-pentamethyl-3H-benzofuran-5-yl)sulfonyl]guanidine hydrochloride (600 mg, 1.03 mmol, 1.00 eq) was added and the reaction mixture was stirred at 30° C. for another 2 hr. LC-MS indicated the starting material was consumed completely. EA (30 mL) was added and the mixture was washed with water (10 mL×3), dried over Na$_2$SO$_4$, concentrated to give tert-butyl-(3S)-3-[[(1S)-1-(1,3-benzothiazole-2-carbonyl)-4-[[N-[(2,2,4,6,7-pentamethyl-3H-benzofuran-5-yl)sulfonyl]carbamimidoyl]amino]butyl]carbamoyl]pyrrolidine-1-carboxylate (500 mg, crude) as a yellow solid.

(3S)—N-[1-(1,3-benzothiazole-2-carbonyl)-4-guanidino-butyl]pyrrolidine-3-carboxamide (8)

To a mixture of TFA (1.9 mL), H$_2$O (0.05 mL), thioanisole (0.05 mL) was added tert-butyl-(3S)-3-[[(1S)-1-(1,3-benzothiazole-2-carbonyl)-4-[[N-[(2,2,4,6,7-pentamethyl-3H-benzofuran-5-yl)sulfonyl]carbamimidoyl]amino]butyl]carbamoyl]pyrrolidine-1-carboxylate (500 mg, 674.83 μmol, 1.00 eq) at 0° C. Then the mixture was stirred at 30° C. for 4 hr. LC-MS indicated the starting material was consumed completely. Water (50 mL) was added and the mixture was lyophilized to give the crude product, which was purified by prep-HPLC (CH$_3$CN/H$_2$O/TFA) to give (3S)—N-[1-(1,3-benzothiazole-2-carbonyl)-4-guanidino-butyl]pyrrolidine-3-carboxamide trifluoroacetate (38.96 mg, 77.53 μmol, 11.5% yield) as a white solid. MS m/z=389.2 (MH$^+$).

Example 12. Preparation of (1S,3R)-3-amino-N-[1-(1,3-benzothiazole-2-carbonyl)-4-guanidino-butyl]cyclopentanecarboxamide (9/10)

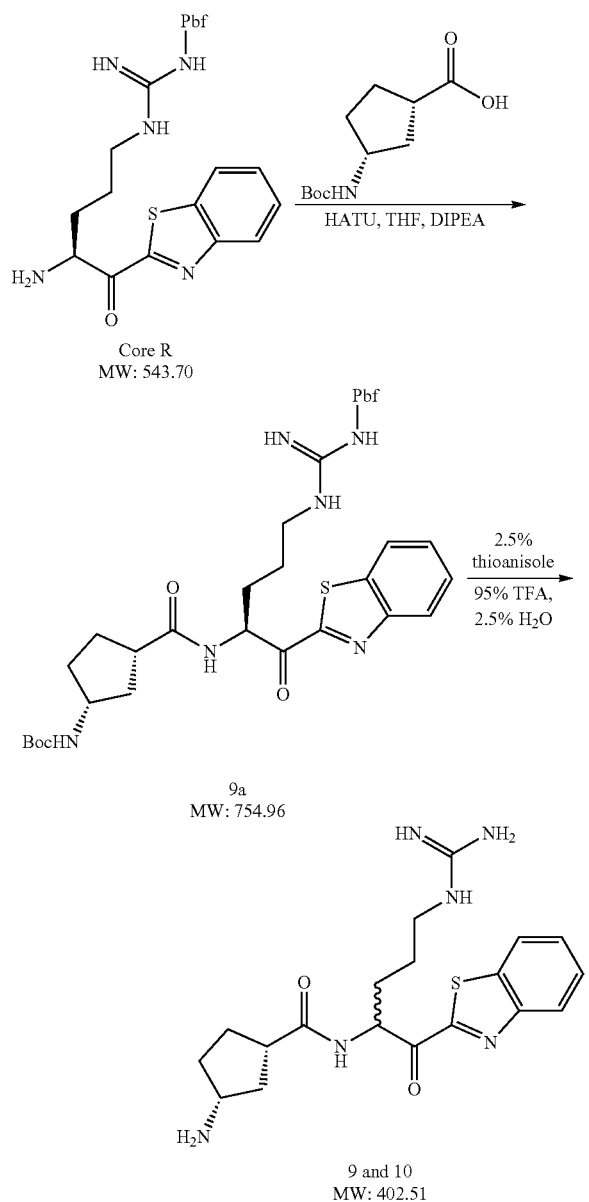

Tert-butyl-N-[(1R,3S)-3-[[(1S)-1-(1,3-benzothiazole-2-carbonyl)-4-[[N-[(2,2,4,6,7-pentamethyl-3H-benzofuran-5-yl)sulfonyl]carbamimidoyl]amino]butyl]carbamoyl]cyclopentyl]carbamate (9a)

To a mixture of 3-tert-butoxycarbonyl-aminocyclopentane carboxylic acid, DIPEA (401 mg, 3.10 mmol, 3.00 eq) in THF (10 mL) was added HATU (472 mg, 1.24 mmol, 1.20 eq) and the mixture was stirred at 0° C. for 0.5 hr. Then 1-[(4S)-4-amino-5-(1,3-benzothiazol-2-yl)-5-oxo-pentyl]-3-[(2,2,4,6,7-pentamethyl-3H-benzofuran-5-yl)sulfonyl]guanidine hydrochloride (600 mg, 1.03 mmol, 1.00 eq) was added and the mixture was stirred at 30° C. for 2 hr. LC-MS indicated the starting material was consumed completely. EA (50 mL) was added and the mixture was washed with water (10 mL×3), dried over $Na_2SO_4$, concentrated to give tert-butyl-N-[(1R,3S)-3-[[(1S)-1-(1,3-benzothiazole-2-carbonyl)-4-[[N-[(2,2,4,6,7-pentamethyl-3H-benzofuran-5-yl)sulfonyl]carbamimidoyl]amino]butyl]carbamoyl]cyclopentyl]carbamate (600 mg, crude) as a yellow solid.

(1S,3R)-3-amino-N-[1-(1,3-benzothiazole-2-carbonyl)-4-guanidino-butyl]cyclo-pentanecarboxamide (9/10)

To a mixture of TFA (1.9 mL), $H_2O$ (0.05 mL), thioanisole (0.05 mL) was added tert-butyl-N-[(1R,3S)-3-[[(1S)-1-(1,3-benzothiazole-2-carbonyl)-4-[[N-[(2,2,4,6,7-pentamethyl-3H-benzofuran-5-yl)sulfonyl]carbamimidoyl]amino]butyl]carbamoyl]cyclopentyl]carbamate (400 mg, 529.83 μmol, 1.00 eq) at 0° C. Then the mixture was stirred at 30° C. for 4 hr. LC-MS indicated the starting material was consumed completely. Water (50 mL) was added and the mixture was lyophilized to give the crude product. The crude product was purified by prep-HPLC ($CH_3CN/H_2O$/TFA) to give (1S,3R)-3-amino-N-[1-(1,3-benzothiazole-2-carbonyl)-4-guanidino-butyl]cyclopentanecarboxamide trifluoroacetate (165.53 mg, 320.46 μmol, 60.5% yield, Peak 1, Compound 9) and (1S,3R)-3-amino-N-[1-(1,3-benzothiazole-2-carbonyl)-4-guanidino-butyl]cyclopentanecarboxamide trifluoroacetate (38.96 mg, 75.42 μmol, 14.2% yield, Peak 2, Compound 10) as light yellow solids. MS m/z=403.1 ($MH^+$) for Compound 9 and Compound 10.

Example 13. Preparation of (2S)-2-acetamido-N-[1-(1,3-benzothiazole-2-carbonyl)-4-guanidino-butl]butanamide (11/12)

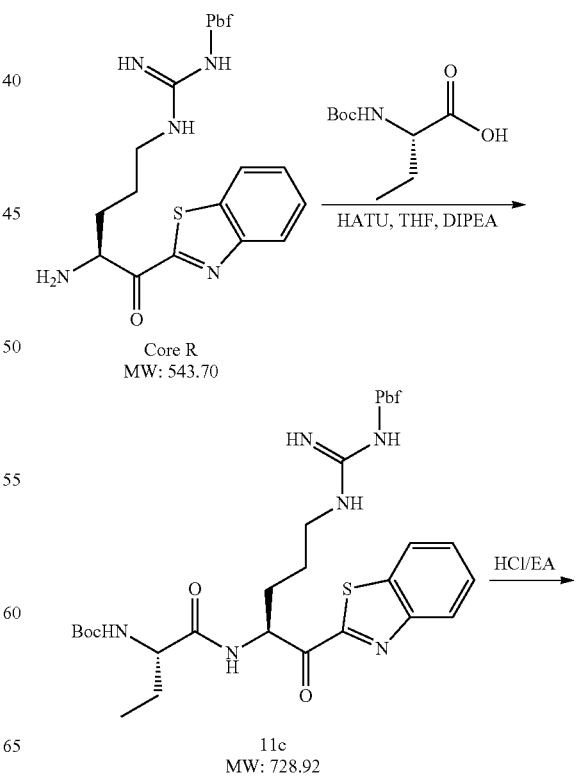

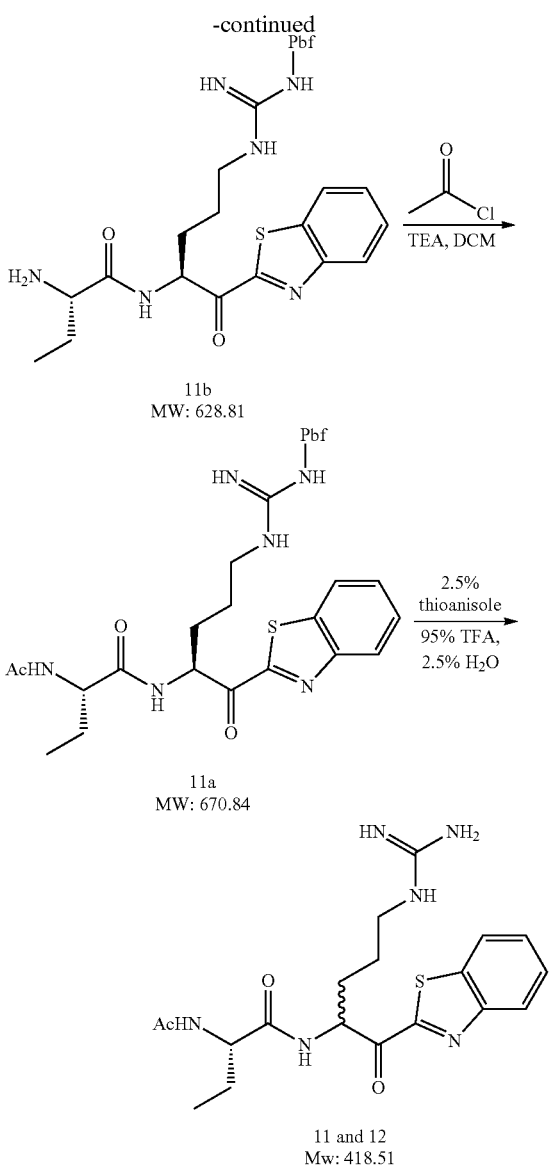

Tert-butyl-N-[(1S)-1-[[(1S)-1-(1,3-benzothiazole-2-carbonyl)-4-[[N-[(2,2,4,6,7-pentamethyl-3H-benzofuran-5-yl)sulfonyl]carbamimidoyl]amino]butyl]carbamoyl]propyl]carbamate (11c)

A mixture of (2S)-2-(tert-butoxycarbonylamino)butanoic acid (251 mg, 1.24 mmol, 1.20 eq), HATU (470 mg, 1.24 mmol, 1.20 eq), DIPEA (400 mg, 3.09 mmol, 3.00 eq) in THF (10 mL) was stirred at 0° C. for 0.5 hr. Then 1-[(4S)-4-amino-5-(1,3-benzothiazol-2-yl)-5-oxo-pentyl]-3-[(2,2,4,6,7-pentamethyl-3H-benzofuran-5-yl)sulfonyl]guanidine hydrochloride (600 mg, 1.03 mmol, 1.00 eq) was added and the mixture was stirred at 30° C. for 2 hr. LC-MS indicated the starting material was consumed completely. EA (50 mL) was added and the mixture was washed with water (20 mL×3), dried over Na$_2$SO$_4$, concentrated to give the crude product, which was purified by flash chromatography to give tert-butyl-N-[(1S)-1-[[(1S)-1-(1,3-benzothiazole-2-carbonyl)-4-[[N-[(2,2,4,6,7-pentamethyl-3H-benzofuran-5-yl) sulfonyl]carbamimidoyl]amino]butyl]carbamoyl]propyl] carbamate (500 mg, 685.95 μmol, 66.6% yield) as a yellow solid.

(2S)-2-amino-N-[(1S)-1-(1,3-benzothiazole-2-carbonyl)-4-[[N-[(2,2,4,6,7-pentamethyl-3H-benzofuran-5-yl)sulfonyl]carbamimidoyl]amino]butyl]butanamide (11b)

To a mixture of tert-butyl-N-[(1S)-1-[[(1S)-1-(1,3-benzothiazole-2-carbonyl)-4-[[N-[(2,2,4,6,7-pentamethyl-3H-benzofuran-5-yl)sulfonyl]carbamimidoyl] amino]butyl]carbamoyl]propyl]carbamate (500 mg, 685.95 μmol, 1.00 eq) in EA (10 mL) was added HCl/EA (4 M, 4 mL). The mixture was stirred at 30° C. for 3 hr. TLC (PE:EA=1:2) indicated the starting material was consumed completely. The mixture was filtered to give (2S)-2-amino-N-[(1S)-1-(1,3-benzothiazole-2-carbonyl)-4-[[N-[(2,2,4,6,7-pentamethyl-3H-benzofuran-5-yl)sulfonyl]carbamimidoyl]amino]butyl]butanamide hydrochloride (400 mg, crude) as a yellow solid.

(2S)-2-acetamido-N-[(1S)-1-(1,3-benzothiazole-2-carbonyl)-4-[[N-[(2,2,4,6,7-pentamethyl-3H-benzofuran-5-yl)sulfonyl]carbamimidoyl]amino]butyl] butanamide (11a)

To a mixture of (2S)-2-amino-N-[(1S)-1-(1,3-benzothiazole-2-carbonyl)-4-[[N-[(2,2,4,6,7-pentamethyl-3H-benzofuran-5-yl)sulfonyl]carbamimidoyl]amino]butyl]butanamide hydrochloride (400 mg, 601.26 μmol, 1.00 eq), TEA (183 mg, 1.80 mmol, 3.00 eq) in DCM (5 mL) was added acetyl chloride (95 mg, 1.20 mmol, 2.00 eq) drop-wise at 0° C. under N$_2$. The mixture was stirred at 0° C. under N$_2$ for 0.5 hr. LC-MS indicated the starting material was consumed completely. DCM (20 mL) was added and the mixture was washed with water (10 mL×3), dried over Na$_2$SO$_4$, concentrated to give (2S)-2-acetamido-N-[(1S)-1-(1,3-benzothiazole-2-carbonyl)-4-[[N-[(2,2,4,6,7-pentamethyl-3H-benzofuran-5-yl)sulfonyl]carbamimidoyl]amino]butyl] butanamide (300 mg, 447.20 μmol, 74.4% yield) as a yellow solid.

(2S)-2-acetamido-N-[1-(1,3-benzothiazole-2-carbonyl)-4-guanidino-butyl]butanamide (11/12)

To a mixture of TFA (1.9 mL), H$_2$O (0.05 mL), thioanisole (0.05 mL) was added (2S)-2-acetamido-N-[(1S)-1-(1,3-benzothiazole-2-carbonyl)-4-[[N-[(2,2,4,6,7-pentamethyl-3H-benzofuran-5-yl)sulfonyl]carbamimidoyl]amino]butyl]butanamide (300 mg, 447.20 μmol, 1.00 eq) at 0° C. Then the mixture was stirred at 30° C. for 4 hr. LC-MS indicated the starting material was consumed completely. Water (50 mL) was added and the mixture was lyophilized to give the crude product, which was purified by prep-HPLC (CH$_3$CN/H$_2$O/TFA) to give (2S)-2-acetamido-N-[1-(1,3-benzothiazole-2-carbonyl)-4-guanidino-butyl]butanamide trifluoroacetate (24.10 mg, 45.25 μmol, 10.1% yield, Peak 1, Compound 11) and (2S)-2-acetamido-N-[1-(1,3-benzothiazole-2-carbonyl)-4-guanidino-butyl]butanamide trifluoroacetate (21.29 mg, 39.98 μmol, 8.9% yield, Peak 2, Compound 12) as light yellow solids. MS m/z=419.1 (MH$^+$) for Compound 11 and Compound 12.

Example 14. Preparation of N-[(1S)-4-guanidino-1-[2-(2,3,5,6-tetrafluorophenoxy)acetyl]butyl]cyclopentanecarboxamide (13)

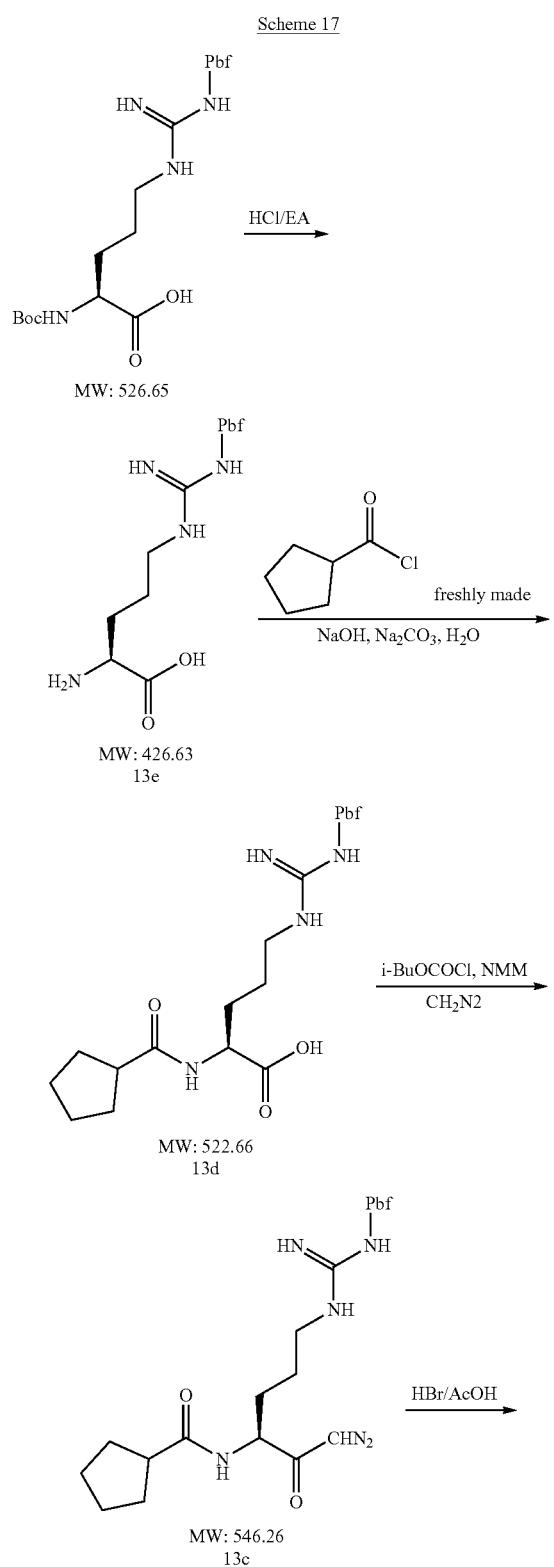

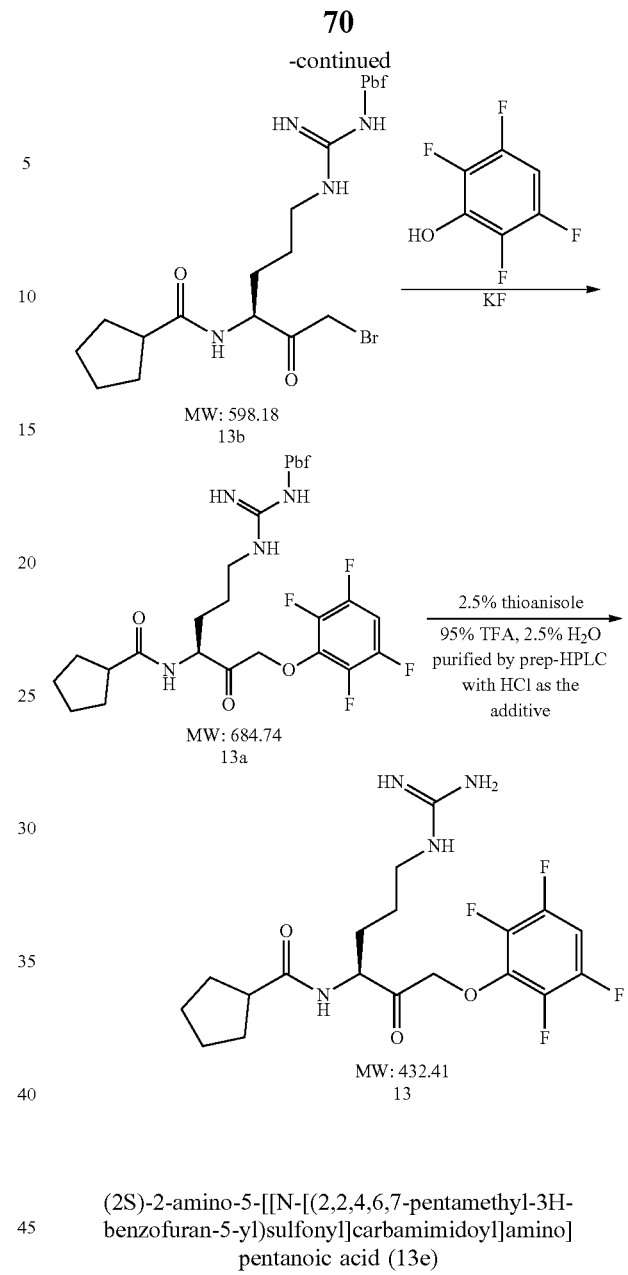

(2S)-2-amino-5-[[N-[(2,2,4,6,7-pentamethyl-3H-benzofuran-5-yl)sulfonyl]carbamimidoyl]amino] pentanoic acid (13e)

To a solution of (2S)-2-(tert-butoxycarbonylamino)-5-[[N-[(2,2,4,6,7-pentamethyl-3H-benzofuran-5-yl)sulfonyl]carbamimidoyl]amino]pentanoic acid (30.00 g, 56.96 mmol, 1.00 eq) in EA (50 mL) was added HCl/EA (4 M, 100 mL, 7.02 eq). The reaction mixture was stirred at 15° C. for 3 hr. LC-MS indicated the starting material was consumed completely and the desired product was detected. The mixture was concentrated to give a residue, which was washed with EA (200 mL). The solid was collected to give (2S)-2-amino-5-[[N-[(2,2,4,6,7-pentamethyl-3H-benzofuran-5-yl)sulfonyl]carbamimidoyl]amino]pentanoic acid hydrochloride (28.00 g) as a white solid. It was used directly without any further purification. $^1$H NMR ((CD$_3$)$_2$SO, 400 MHz) d 8.41 (d, J=7.2, 1H), 7.88 (t, J=5.6, 1H), 7.62-7.56 (m, 1H), 5.25 (d, J=17.6, 1H), 5.18 (d, J=17.6, 1H), 4.34-4.30 (m, 1H), 3.13-3.09 (m, 2H), 2.71-2.66 (m, 1H), 1.77-1.65 (m, 3H), 1.62-1.45 (m, 9H).

(2S)-2-(cyclopentanecarbonylamino)-5-[[N-[(2,2,4,6,7-pentamethyl-3H-benzofuran-5-yl)sulfonyl]carbamimidoyl]amino]pentanoic acid (13d)

To a solution of (2S)-2-amino-5-[[N-[(2,2,4,6,7-pentamethyl-3H-benzofuran-5-yl)-sulfonyl]carbamimidoyl]amino] pentanoic acid hydrochloride (25.00 g, 54.00 mmol, 1.00 eq) in H$_2$O (200 mL) were added NaOH (2.16 g, 54.00 mmol, 1.00 eq) and Na$_2$CO$_3$ (23.00 g, 217.08 mmol, 4.02 eq). Then the mixture was cooled to 0° C. and cyclopentanecarbonyl chloride (8.59 g, 64.80 mmol, 1.20 eq) in EA (80.00 mL) was added dropwise to the above solution. Then the mixture was stirred at 15° C. for 14 hr. LC-MS indicated the desired product was detected. The mixture was adjusted to pH=4-5 with solid KHSO$_4$ and the resulting solution was extracted with EA (500 mL×2). The organic layers were combined, washed with sat. brine (1000 mL) and concentrated to give (2S)-2-(cyclopentanecarbonylamino)-5-[[N-[(2,2,4,6,7-pentamethyl-3H-benzofuran-5-yl)sulfonyl]carbamimidoyl]amino]pentanoic acid (23.36 g, crude) as a yellow oil. It was used directly without further purification.

N-[(1S)-1-(2-diazoacetyl)-4-[[N-[(1,1,4,6,7-pentamethyl-3H-isobenzofuran-5-yl)sulfonyl]carbamimidoyl]amino]butyl]cyclopentanecarboxamide (13c)

To a solution of (2S)-2-(cyclopentanecarbonylamino)-5-[[N-[(1,1,4,6,7-pentamethyl-3H-isobenzofuran-5-yl)sulfonyl]carbamimidoyl]amino]pentanoic acid (2.00 g, 3.83 mmol, 1.00 eq) in THF (20 mL) was added NMM (387 mg, 3.83 mmol, 1.00 eq) and isobutyl carbonochloridate (523 mg, 3.83 mmol, 1.00 eq). The mixture was stirred at −20° C. for 1 h under N$_2$. Then diazomethane (242 mg, 5.75 mmol, 1.50 eq) was added. The mixture was stirred at 0° C. for 4 h. The mixture was diluted with H$_2$O (30 mL), extracted with EA (30 mL×2). The combined organic layers was dried over Na$_2$SO$_4$, filtered and concentrated under reduced pressure to give a residue, which was purified by silica gel chromatography (EA) to give N-[(1S)-1-(2-diazoacetyl)-4-[[N-[(1,1,4,6,7-pentamethyl-3H-isobenzofuran-5-yl)sulfonyl]carbamimidoyl]amino]butyl]cyclopentanecarboxamide (300 mg, 548.77 µmol, 14.33% yield) as a yellow solid.

N-[(1S)-1-(2-bromoacetyl)-4-[[N-[(1,1,4,6,7-pentamethyl-3H-isobenzofuran-5-yl)sulfonyl]carbamimidoyl]amino]butyl]cyclopentanecarboxamide (13b)

To a solution of N-[(1S)-1-(2-diazoacetyl)-4-[[N-[(1,1,4,6,7-pentamethyl-3H-isobenzofuran-5-yl)sulfonyl]carbamimidoyl]amino]butyl]cyclopentanecarboxamide (250 mg, 457.31 µmol, 1.00 eq) in EA (10 mL) was added HBr/AcOH (150 µL, Purity: 33%) was stirred at −20° C. for 10 min. The mixture was basified with sat. NaHCO$_3$ till pH=8, extracted with EA (20 mL×3). The combined organic layers were dried over Na$_2$SO$_4$, filtered and concentrated under reduced pressure to give N-[(1S)-1-(2-bromoacetyl)-4-[[N-[(1,1,4,6,7-pentamethyl-3H-isobenzofuran-5-yl)sulfonyl]carbamimidoyl]amino]butyl]cyclopentanecarboxamide (200 mg, crude) as a yellow solid.

N-[(1S)-4-[[N-[(1,1,4,6,7-pentamethyl-3H-isobenzofuran-5-yl)sulfonyl]carbamimidoyl]amino]-1-[2-(2,3,5,6-tetrafluorophenoxy)acetyl]butyl]cyclopentanecarboxamide (13a)

To a solution of N-[(1S)-1-(2-bromoacetyl)-4-[[N-[(1,1,4,6,7-pentamethyl-3H-isobenzofuran-5-yl) sulfonyl]carbamimidoyl]amino]butyl]cyclopentanecarboxamide (200 mg, 333.57 µmol, 1.00 eq) in DMF (10.00 mL) were added KF (58 mg, 1.00 mmol, 3.00 eq) and 2,3,5,6-tetrafluorophenol (66 mg, 400.28 µmol, 1.20 eq). The mixture was stirred at 20° C. for 12 h. The mixture was diluted with H$_2$O (20 mL), extracted with EA (20 mL×2). The combined organic layers were washed with brine (20 mL×5), dried over Na$_2$SO$_4$, filtered and concentrated under reduced pressure. The residue was purified by prep-TLC (PE/EA=1/2) to give N-[(1S)-4-[[N-[(1,1,4,6,7-pentamethyl-3H-isobenzofuran-5-yl)sulfonyl]carbamimidoyl]amino]-1-[2-(2,3,5,6-tetrafluorophenoxy)acetyl]butyl]cyclopentanecarboxamide (200 mg, 292.08 µmol, 87.56% yield) as a white solid.

N-[(1S)-4-guanidino-1-[2-(2,3,5,6-tetrafluorophenoxy)acetyl]butyl]cyclopentanecarboxamide (13)

A mixture of N-[(1S)-4-[[N-[(1,1,4,6,7-pentamethyl-3H-isobenzofuran-5-yl)sulfonyl]carbamimidoyl]amino]-1-[2-(2,3,5,6-tetrafluorophenoxy)acetyl]butyl]cyclopentanecarboxamide (200 mg, 292.08 µmol, 1.00 eq) in TFA (19.38 g, 169.98 mmol, 581.96 eq), thioanisole (350 mg, 2.82 mmol, 9.65 eq) and H$_2$O (5 mg, 292 µmol, 1.00 eq). The mixture was stirred at 0° C. for 1 h. The mixture was concentrated and the residue was purified by prep-HPLC (CH$_3$CN/H$_2$O/HCl) to give N-[(1S)-4-guanidino-1-[2-(2,3,5,6-tetrafluorophenoxy)acetyl]butyl]-cyclopentanecarboxamide hydrochloride (36.70 mg, 78.27 µmol, 26.8% yield) as a white solid. MS m/z=433.2 (MH$^+$).

Example 15. Preparation of 3-azido-N-[(1S)-4-guanidino-1-[2-(2,3,5,6-tetrafluorophenoxy) acetyl]butyl]benzamide (14)

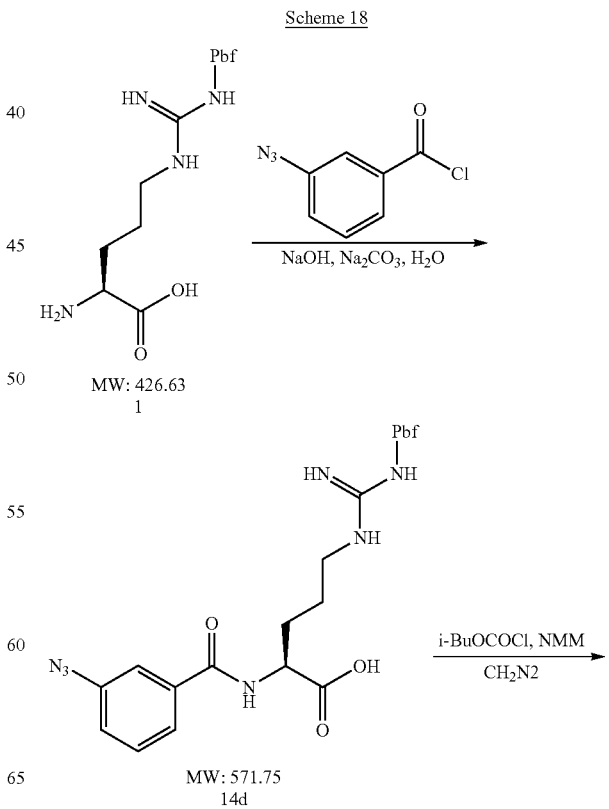

Scheme 18

-continued

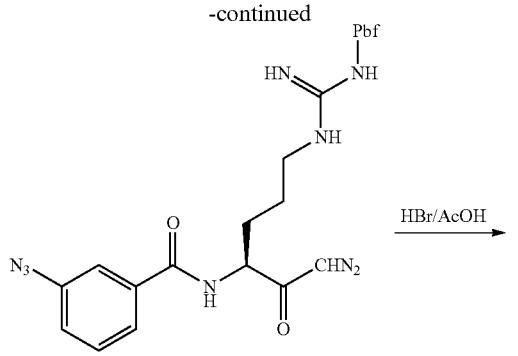

MW: 595.78
14c

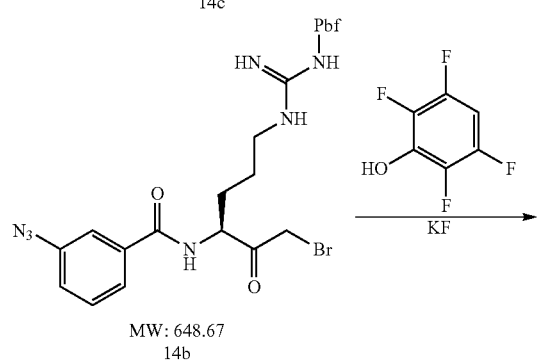

MW: 648.67
14b

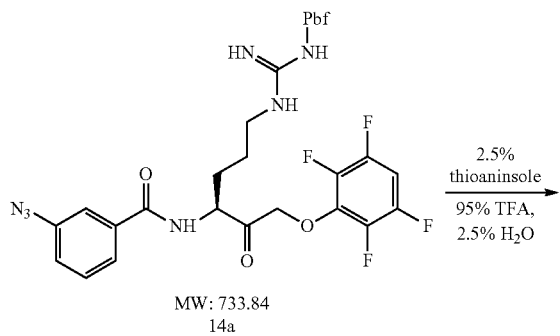

MW: 733.84
14a

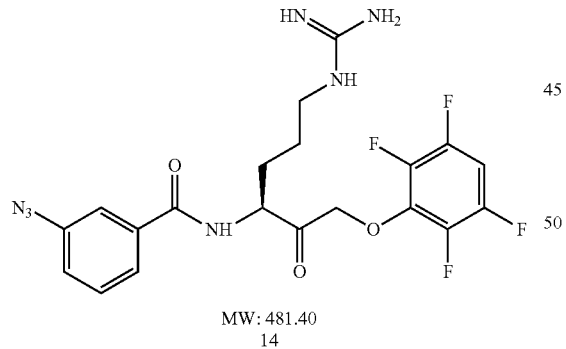

MW: 481.40
14

(2S)-2-[(3-azidobenzoyl)amino]-5-[[N-[(1,1,4,6,7-pentamethyl-3Hisobenzofuran-5-yl)sulfonyl]carbamimidoyl]amino]pentanoic acid (14d)

To a solution of (2S)-2-amino-5-[[N-[(1,1,4,6,7-pentamethyl-3H-isobenzofuran-5-yl)sulfonyl]carbamimidoyl]amino]pentanoic acid hydrochloride (5.00 g, 11.72 mmol, 1.00 eq) in H$_2$O/EA (1/1, 100 m) were added NaOH (469 mg, 11.72 mmol, 1.00 eq), Na$_2$CO$_3$ (1.24 g, 11.72 mmol, 1.00 eq) and 3-azidobenzoyl chloride (2.13 g, 11.72 mmol, 1.00 eq). The mixture was stirred at 20° C. for 5 h. The mixture was acidified with KHSO$_4$ till pH=4, concentrated under reduced pressure. The residue was purified by silica gel chromatography eluted with DCM/MeOH=10/1 to give (2S)-2-[(3-azidobenzoyl)amino]-5-[[N-[(1,1,4,6,7-pentamethyl-3Hisobenzofuran-5-yl)sulfonyl]carbamimidoyl]amino]pentanoic acid (3.50 g, crude) as a white solid. $^1$H NMR ((CD$_3$)$_2$SO, 400 MHz) d 9.11 (d, J=7.2, 1H), 7.86 (t, J=5.6, 1H), 7.76 (d, J=7.3, 1H), 7.64 (s, 1H), 7.56-7.52 (m, 2H), 7.33 (d, J=6.9, 1H), 5.35 (d, J=17.6, 1H), 5.28 (d, J=17.6, 1H), 4.61-4.57 (m, 1H), 3.23-3.06 (m, 2H), 1.94-1.85 (m, 1H), 1.77-1.71 (m, 1H), 1.60-1.44 (m, 2H).

3-azido-N-[(1S)-1-(2-diazoacetyl)-4-[[N-[(1,1,4,6,7-pentamethyl-3H-isobenzofuran-5-yl)sulfonyl]carbamimidoyl]amino]butyl]benzamide (14c)

To a solution of (2S)-2-[(3-azidobenzoyl)amino]-5-[[N-[(1,1,4,6,7-pentamethyl-3H-isobenzofuran-5-yl)sulfonyl]carbamimidoyl]amino]pentanoic acid (3.50 g, 6.12 mmol, 1.00 eq) in THF (50 mL) were added NMM (619 mg, 6.12 mmol, 1.00 eq) and isobutyl carbonochloridate (836 mg, 6.12 mmol, 1.00 eq). The mixture was stirred at −20° C. for 1 h. Then diazomethane (257 mg, 6.12 mmol, 1.00 eq) was added and the solution was stirred at −20° C. for 3 h. The solution was used directly in the next step without purification.

3-azido-N-[(1S)-1-(2-bromoacetyl)-4-[[N-[(1,1,4,6,7-pentamethyl-3H-isobenzofuran-5-yl)sulfonyl]carbamimidoyl]amino]butyl]benzamide (14b)

To a solution of 3-azido-N-[(1S)-1-(2-diazoacetyl)-4-[[N-[(1,1,4,6,7-pentamethyl-3H-isobenzofuran-5-yl)sulfonyl]carbamimidoyl]amino]butyl]benzamide (3.50 g, 5.88 mmol, 1.00 eq) was added HBr/AcOH (1.44 g, 5.88 mmol, 1.00 eq, Purity: 33%). The mixture was stirred at −20° C. for 20 min. The mixture was diluted with H$_2$O (50 mL), extracted with EA (50 mL×3). The organic layers were combined, washed with brine (50 mL×3), dried over Na$_2$SO$_4$, filtered and concentrated under reduced pressure to give 3-azido-N-[(1S)-1-(2-bromoacetyl)-4-[[N-[(1,1,4,6,7-pentamethyl-3H-isobenzofuran-5-yl)sulfonyl]carbamimidoyl]amino]butyl]benzamide (4.00 g, crude) as yellow oil.

3-azido-N-[(1S)-4-[[N-[(1,1,4,6,7-pentamethyl-3H-isobenzofuran-5-yl)sulfonyl]carbamimidoyl]amino]-1-[2-(2,3,5,6-tetrafluorophenoxy)acetyl]butyl]benzamide (14a)

To a solution of 3-azido-N-[(1S)-1-(2-bromoacetyl)-4-[[N-[(1,1,4,6,7-pentamethyl-3H-isobenzofuran-5-yl)sulfonyl]carbamimidoyl]amino]butyl]benzamide (4.00 g, 6.17 mmol, 1.00 eq) in DMF (50 mL) were added KF (1.07 g, 18.50 mmol, 3.00 eq) and 2,3,5,6-tetrafluorophenol (1.23 g, 7.40 mmol, 1.20 eq). The mixture was stirred at 20° C. for 12 h. The mixture was diluted with H$_2$O (100 mL) and extracted with EA (100 mL). The organic layer was washed with brine (100 mL×5), dried over Na$_2$SO$_4$, filtered and concentrated under reduced pressure. The residue was purified by silica gel chromatography eluted with PE:EA=1:1 to give 3-azido-N-[(1S)-4-[[N-[(1,1,4,6,7-pentamethyl-3H-isobenzofuran-5-yl)sulfonyl]carbamimidoyl]amino]-1-[2-(2,3,5,6-tetrafluorophenoxy)acetyl]butyl]benzamide (350 mg, 477.01 μmol, 7.7% yield) as a white solid.

3-azido-N-[(1S)-4-guanidino-1-[2-(2,3,5,6-tetrafluorophenoxy)acetyl]butyl]benzamide (14)

A solution of 3-azido-N-[(1S)-4-[[N-[(1,1,4,6,7-pentamethyl-3H-isobenzofuran-5-yl)sulfonyl]carbamimidoyl]amino]-1-[2-(2,3,5,6-tetrafluorophenoxy)acetyl]butyl]benzamide (340 mg, 463.39 µmol, 1.00 eq) in TFA (10 mL), $H_2O$ (0.25 mL) and thioanisole (0.25 mL) was stirred at 0° C. for 1 h. The mixture was concentrated and the residue was purified by prep-HPLC ($CH_3CN/H_2O$/HCl) to give 3-azido-N-[(1S)-4-guanidino-1-[2-(2,3,5,6-tetrafluorophenoxy)acetyl]butyl]benzamide hydrochloride (120 mg, 249.27 µmol, 53.8% yield) as a white solid. MS m/z=482.1 ($MH^+$).

Example 16. Inhibition of Arginine Gingipain by Compounds of the Invention

The capacities of compounds of the present invention to inhibit the activity of RgpB were measured in a fluorogenic assay similar to those described in Barret *Biochemical Journal.* 1980, 187(3), 909. The specific assay conditions were as follows. Buffer: pH=7.5, 100 mM Tris-HCl, 75 mM NaCl, 2.5 mM $CaCl_2$, 10 mM cysteine, 1% DMSO after all additions. Protein: 0.02 nM RgpB, isolated from culture of *Porphyromonas gingivalis*, as described in Pike et al. *J Biol. Chem.* 1994, 269(1), 406, and Potempa and Nguyen. *Current Protocols in Protein Scienc.* 2007, 21.20.1-21.20.27. Fluorogenic substrate: 10 uM Boc-Phe-Ser-Arg-MCA. Time=90 minutes. Temperature=37° C. Each compound: 10 concentrations, starting at either 100 uM or 100 nM, with lower concentrations generated by serial 3-fold dilutions. By testing a range of concentrations for each compound, the concentration required to inhibit the activity of RgpB by 50% (the "$IC_{50}$") was determined. Under the described assay conditions, signal-to-noise was excellent, and Z factor was greater than 0.7.

The inhibitory of activity of compounds described herein was tested against Kgp, RgpB, RgpA, and trypsin. Each of Compound Nos. 4-8, 10, 11, and 14 as described herein exhibited an RgpB $IC_{50}$ value below 10 nM. Each of Compound Nos. 2, 3, 9, and 12 exhibited an RgpB $IC_{50}$ value below 2 nM. Compound No. 1 and Compound No. 13 each exhibited an RgpB $IC_{50}$ value below 1 nM.

Each of Compound Nos. 1, 3, 11, and 12 as described herein exhibited an RgpA $IC_{50}$ value below 5 nM. Compound No. 13 and Compound No. 14 each exhibited an RgpA $IC_{50}$ value below 500 pM.

Each of Compound Nos. 1-12 exhibited a Kgp $IC_{50}$ value above 10 µM. Compound No. 14 exhibited a Kgp $IC_{50}$ value above 450 nM, and Compound No. 13 exhibited a Kgp $IC_{50}$ value above 150 nM. Each of Compound Nos. 1-3 and 5-10 exhibited a trypsin $IC_{50}$ value above 1 µM. Compound No. 4 exhibited a trypsin $IC_{50}$ value above 350 nM, and Compound Nos. 11 and 12 each exhibited a trypsin $IC_{50}$ value above 40 nM.

Figure 5:
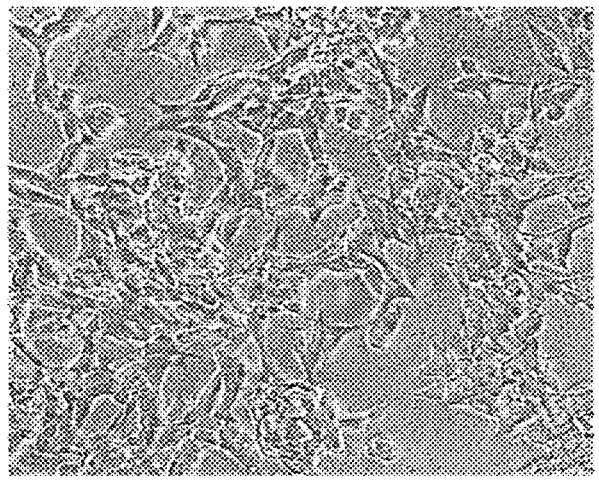
FIG. 5 shows that Compound 13 can rescue SHSY-5Y cells from *P. gingivalis* toxicity.
Figure 5:
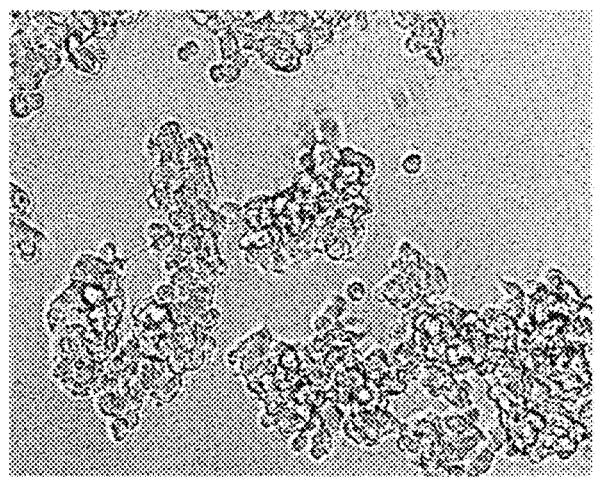
Figure 5:
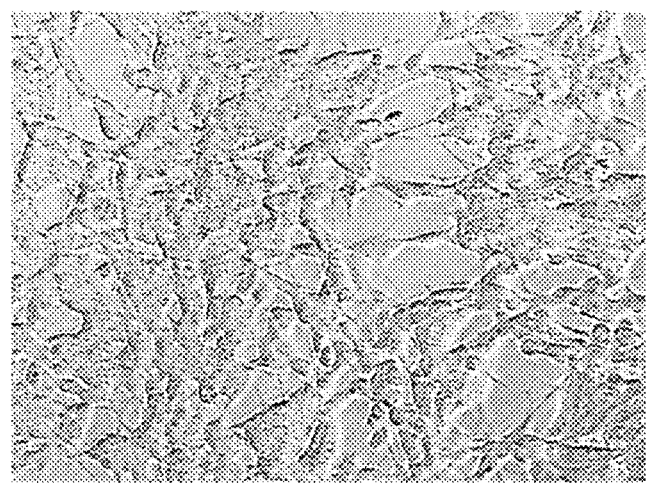

Example 17. Rescue of Neuroblastoma Cells from *P. gingivalis* Toxicity Using Compounds of the Invention SH-SY5Y neuroblastoma cells were cultured based on established methods [Saberi S., et al. *Cell Mol Neurobiol* 2013. 33: 5 747-751]. The strain *P. gingivalis* ATCC BAA-308 was streaked onto a brain heart infusion agar (BHA), and the plate was incubated for 72 h at 37° C. in an anaerobic workstation with an atmosphere of 80% $N_2$, 10% $CO_2$, and 10% $H_2$. The plates were removed from the anaerobic workstation for testing and processed under ambient atmosphere. The bacteria were harvested and suspended in complete medium-Pen/Strep (without Pen/Strep). The turbidity of the suspension was adjusted to 0.5, as measured using a MicroScan® Turbidity Meter (Siemens), which is equivalent to ~$6\times10^8$ cfu/mL (for MOI 1:1000) and incubated with the cells for 48 hours. 4 µg/mL of Compound 13 was added to the media at the time of introduction of the bacteria. Results were recorded using a digital microscope camera (FIG. 5). *P. gingivalis* is toxic to cells, while Compound 13 prevented the toxicity. Other compounds of the invention are tested as described for Compound 13.

Figure 6:
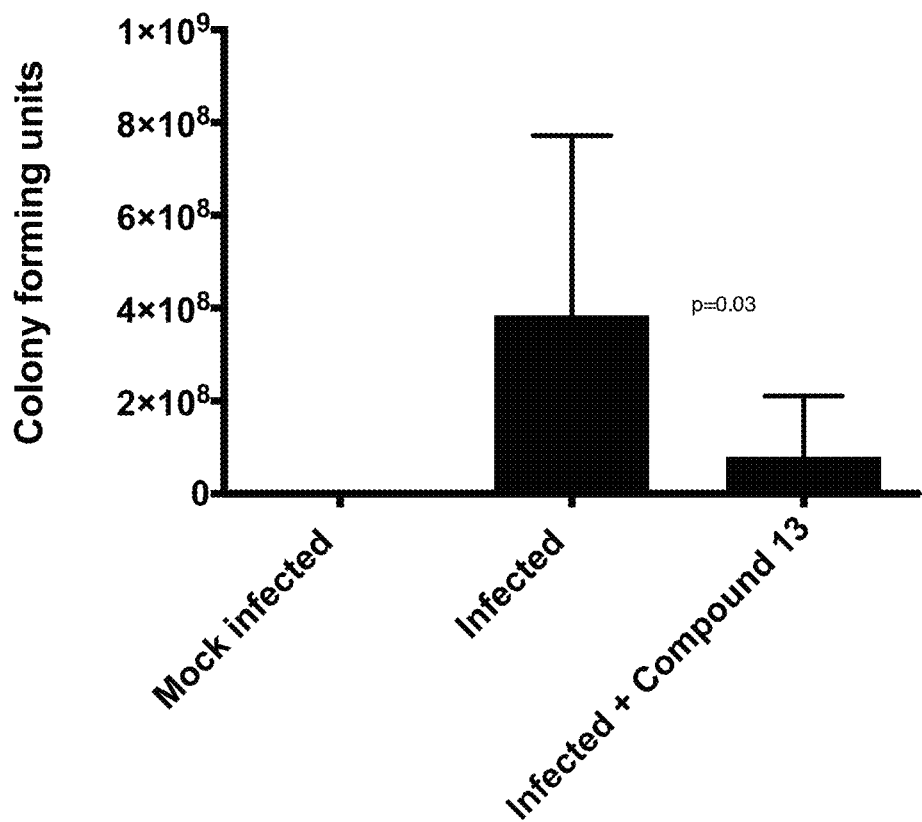
FIG. 6 shows the level of *P. gingivalis* in brain tissue as measured by quantitative PCR, with and without treatment with Rgp inhibitor after *P. gingivalis* infection.

Example 18. Rgp Inhibitors Prevent Infection of Brain Tissue by *P. gingivalis* In Vivo BalbC mice were given a tooth ligature and infected by oral lavage with *P gingivalis* W83 ($1\times10^9$ CFU in 2% carboxymethyl cellulose) or vehicle for 6 weeks. Compound 13 was delivered BID subcutaneously in 25% Pluronic F127 on day 35-70. On day 70, mice were sacrificed and perfused with PBS prior to dissection. DNA was isolated from one quarter of the brain using a DNEasy Blood & Tissue Kit (Qiagen). Forward and reverse primers for RgpB were used for qPCR to quantify *P. gingivalis* DNA in the brain tissue. The forward primer sequence was 5'-AGCAACCAGC-TACCGTTTAT-3' (SEQ ID NO: 1). The reverse primer sequence was 5'-GTACCTGTCGGTTTACCATCTT-3' (SEQ ID NO: 2). The probe sequence was 5'-6-FAM-TACCATGTTTCGCAGAAGCCCTGA-TAMRA-3' (SEQ ID NO: 3). As shown in FIG. 6, Compound 13 demonstrates efficacy against *P. gingivalis* infection in the brain.

Example 19. Gingipain Inhibitors Prevent Degradation of Human Collagen

Figure 7:
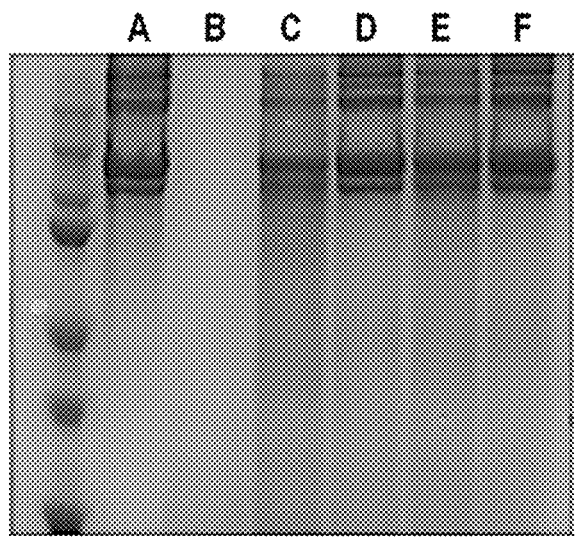
FIG. 7 shows that gingipain inhibitors prevent the degradation of human collagen by *P. gingivalis* (Pg). SDS polyacrylamide gel electrophoresis (SDS-PAGE) was used for analysis of human collagen (lane A); Pg supernatant (lane B); collagen exposed to Pg supernatant in the absence of gingipain inhibitors (lane C); collagen exposed to Pg supernatant in the presence of Rgp inhibitor (Compound 13, lane D); collagen exposed to Pg supernatant in the presence of Kgp inhibitor (lane E); and collagen exposed to Pg supernatant in the presence of Rgp inhibitor (Compound 13) and Kgp inhibitor.

*P. gingivalis* was grown to exponential phase (OD 600 nm=0.6) in a Coy's anaerobic chamber under 5% hydrogen, 10% carbon dioxide, and 95% nitrogen. The bacteria were centrifuged at 5000×g for 10 min at 4° C., and then the supernatant was collected. The supernatant was concentrated by centrifugation at 5000×g for 60 min at 4° C. min using Corning Spin-X UF-20 concentrator tubes and then at 17,000×g for 30 min using Corning Spin-X UF500 concentrator tubes. 10 µg of Collagen type I was incubated with 0.6 µg of *P. gingivalis* culture supernatant for 1h in the absence or presence of 50 µM Rgp inhibitor (Compound 13, Table 1), 50 µM Kgp inhibitor ((S)—N-(6-guanidino-2-oxo-1-(2,3,5,6-tetrafluorophenoxy)hexan-3-yl)cyclopentanecarboxamide; described in U.S. Pat. Appl. Pub. No. 2016/0096830), or both. Reaction mixtures contained 5 mM cysteine, 20 mM sodium phosphate buffer, pH 7.5. After incubation, the reaction was terminated by the addition of protease inhibitor cocktail (Sigma). The samples were then analyzed by SDS-polyacrylamide gel electrophoresis. Following separation, the gels were stained with Biosafe Coomassie (Bio-Rad). The gel data (e.g., FIG. 7) showed that the Rgp inhibitor and Kgp inhibitor prevent degradation of collagen by the gingipain-containing *P. gingivalis* supernatant.

Example 20. Subcutaneous Delivery of Rgp Inhibitors

Compound 13 was dissolved at a concentration of 1 mg/mL in in water containing carboxymethylcellulose (2% w/w) or Pluronic F127 (25% w/w). Solutions were kept on ice, and 10 mg/kg of each solution was administered to 3 male $CD_1$ mice. Plasma was collected at 7 time points. Concentrations in plasma were determined by HPLC with tandem mass (MS/MS) detection.

Plasma samples were precipitated with a mixture containing 80% acetonitrile. Samples were further diluted with water containing 0.1% formic acid. Chromatographic separation was performed on a reversed phase column (2.1×50 mm, particle size: 2.5 m, Xbridge C8, Waters, USA). Components were separated using a linear gradient of acetonitrile containing 0.1% formic acid in ultrapurified $H_2O$ containing 0.1% formic acid (flow rate 0.2 mL/min).

MS analyses were performed using an API 5500 QTRAP system having an API 5500 QTRAP detector and a Turbo Ion Spray interface (both from Applied Biosystems, USA). The acquisitions were performed in positive ionization mode, with optimized settings for the analytes. The instrument was operated in multiple-reaction-monitoring (MRM) mode, the following transition was used to quantify compound 13; 433.4->112.1. Data were calibrated and quantified using the Analyst™ data system (Applied Biosystems) using the response of the analyte versus the concentration. Plasma concentration data resulting from subcutaneous administration of Compound 13 in the carboxymethylcellulose or Pluronic F127 is shown in FIG. 8, demonstrating increased concentration of Compound 13 over an extended time period after administration in Pluronic.

Although the foregoing has been described in some detail by way of illustration and example for purposes of clarity and understanding, one of skill in the art will appreciate that certain changes and modifications can be practiced within the scope of the appended claims. In addition, each reference provided herein is incorporated by reference in its entirety to the same extent as if each reference was individually incorporated by reference.

What is claimed is:

1. A compound according to Formula I:

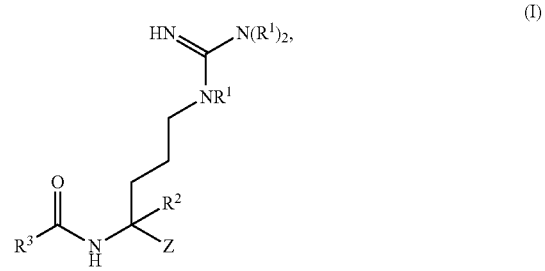

or a pharmaceutically acceptable salt thereof, wherein:

Z is halogen-substituted aryloxymethyl-carbonyl;

each $R^1$ is independently selected from the group consisting of hydrogen, $C_{1-4}$ alkyl, and an amine protecting group;

$R^2$ is selected from the group consisting of hydrogen and $C_{1-4}$ alkyl;

$R^3$ is selected from the group consisting of $C_{3-8}$ cycloalkyl, $C_{3-8}$ alkyl, $C_{6-10}$ aryl, 5-to-12 membered heteroaryl, and 5-to-12 membered heterocyclyl, wherein $R^3$ is optionally substituted with one or more $R^4$ substituents independently selected from the group consisting of halo, —CN, —NO$_2$, —N$_3$, —OH, $R^a$, —OR$^b$, —N(R$^d$)$_2$, —(CH$_2$)$_k$C(O)R$^c$, —NR$^d$(CH$_2$)$_u$C(O)R$^c$, —O(CH$_2$)$_u$C(O)R$^c$, —(CH$_2$)$_k$CON(R$^d$)$_2$,

---

SEQUENCE LISTING

<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: Synthetic Primer

<400> SEQUENCE: 1
agcaaccagc taccgtttat                                         20

<210> SEQ ID NO 2
<211> LENGTH: 22
<212> TYPE: DNA
<213> ORGANISM: Artificial Sequence
<220> FEATURE:
<223> OTHER INFORMATION: Synthetic Primer

<400> SEQUENCE: 2
gtacctgtcg gtttaccatc tt                                      22

<210> SEQ ID NO 3
<211> LENGTH: 24
<212> TYPE: DNA
<213> ORGANISM: Artificial Sequence
<220> FEATURE:
<223> OTHER INFORMATION: Synthetic Probe

<400> SEQUENCE: 3
taccatgttt cgcagaagcc ctga                                    24

—(CH$_2$)$_k$NR$^d$C(O)R$^c$, —NR$^d$(CH$_2$)$_u$CON(R$^d$)$_2$, —NR$^d$(CH$_2$)$_u$NR$^d$C(O)R$^c$, —O(CH$_2$)$_u$CON(R$^d$)$_2$, and —O(CH$_2$)$_u$NR$^d$C(O)R$^c$;

each R$^a$, R$^b$, and R$^c$ is independently selected from the group consisting of C$_{1-4}$ alkyl and C$_{1-4}$ haloalkyl, each R$^d$ is independently selected from the group consisting of hydrogen and C$_{1-8}$ alkyl, each subscript k is independently selected from 0, 1, 2, 3, 4, 5, and 6, and each subscript u is independently selected from 1, 2, 3, 4, 5, and 6;

provided that R$^3$ and the carbonyl to which it is bonded form a moiety other than prolinyl, substituted prolinyl, argininyl, substituted argininyl, phenylalaninyl, substituted phenylalaninyl, tert-butylaminocarbonyl, or tert-butyloxycarbonyl.

2. The compound of claim 1, or a pharmaceutically acceptable salt thereof, wherein Z is fluorine-substituted phenoxymethyl-carbonyl.

3. The compound of claim 2, or a pharmaceutically acceptable salt thereof, wherein R$^2$ is hydrogen.

4. The compound of claim 1, having a structure according to Formula Ia:

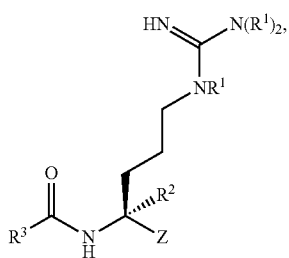

(Ia)

or a pharmaceutically acceptable salt thereof.

5. The compound of claim 4, or a pharmaceutically acceptable salt thereof, wherein Z is fluorine-substituted phenoxymethyl-carbonyl.

6. The compound of claim 5, or a pharmaceutically acceptable salt thereof, wherein R$^2$ is hydrogen.

7. The compound of claim 1, or a pharmaceutically acceptable salt thereof, wherein Z is (2,3,5,6-tetrafluorophenoxymethyl)carbonyl.

8. The compound of claim 1, having a structure according to Formula Ib:

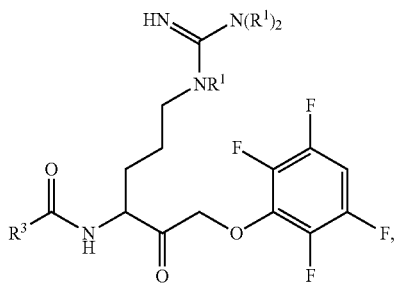

(Ib)

or a pharmaceutically acceptable salt thereof.

9. The compound of claim 8, or a pharmaceutically acceptable salt thereof, wherein R$^3$ is selected from the group consisting of C$_{3-8}$ cycloalkyl, C$_{6-10}$ aryl, 5-to-12 membered heteroaryl, and 5-to-12 membered heterocyclyl, each of which is optionally substituted with one or more R$^4$ substituents.

10. The compound of claim 9, wherein R$^3$ is selected from the group consisting of cyclopentyl, phenyl, and azidophenyl.

11. The compound of claim 8, which is selected from the group consisting of:

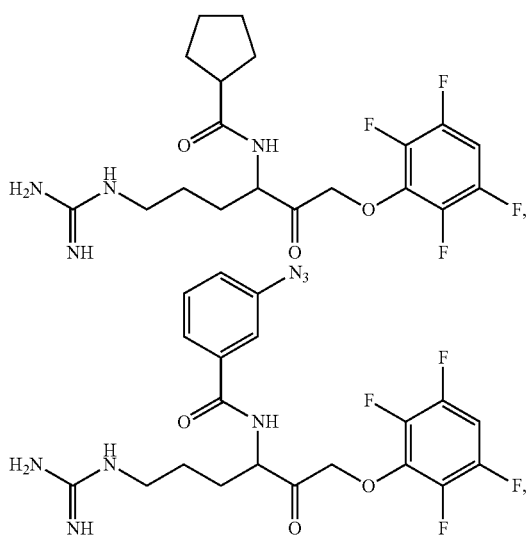

and pharmaceutically acceptable salts thereof.

12. The compound of claim 8, which is selected from the group consisting of:

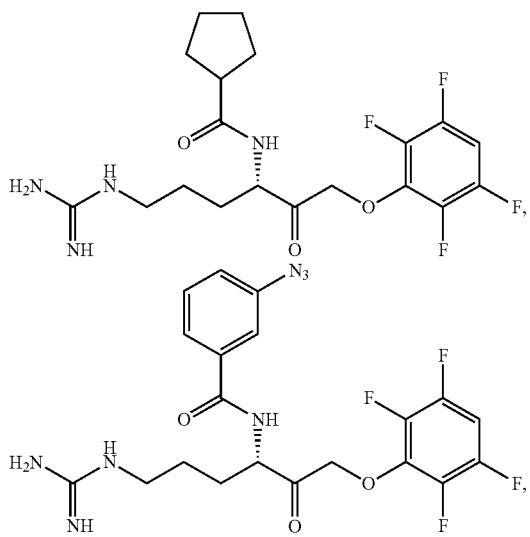

and pharmaceutically acceptable salts thereof.

13. A pharmaceutical composition comprising a compound of claim 1 and a pharmaceutically acceptable excipient.

14. A method of treating a disease or condition associated with *P. gingivalis* infection, the method comprising administering to the subject an effective amount of a compound according to claim 1, or a pharmaceutically acceptable salt thereof.

15. The method of any one of claim 14, wherein the disease or condition is selected from a brain disorder, periodontal disease, diabetes, a cardiovascular disease, arthritis, rheumatoid arthritis, osteoarthritis, infectious arthritis, psoriatic arthritis, elevated risk of preterm birth, pneumonia, cancer, a kidney disease, a liver disease, a retinal disorder, and glaucoma.

16. The method of claim 15, wherein the disease or condition is a brain disorder.

17. The method of claim 16, wherein the brain disorder is selected from Alzheimer's disease, Down's syndrome, epilepsy, autism, Parkinson's disease, essential tremor, frontotemporal dementia, progressive supranuclear palsy, amyotrophic lateral sclerosis, Huntington's disease, multiple sclerosis, mild cognitive impairment, age associated memory impairment, chronic traumatic encephalopathy, stroke, cerebrovascular disease, Lewy Body disease, multiple system atrophy, schizophrenia, and depression.

\* \* \* \* \*